(12) United States Patent
Hoeprich, Jr. et al.

(10) Patent No.: US 11,279,749 B2
(45) Date of Patent: Mar. 22, 2022

(54) SYNTHETIC APOLIPOPROTEINS, AND RELATED COMPOSITIONS METHODS AND SYSTEMS FOR NANOLIPOPROTEIN PARTICLES FORMATION

(71) Applicant: LAWRENCE LIVERMORE NATIONAL SECURITY, LLC, Livermore, CA (US)

(72) Inventors: Paul D. Hoeprich, Jr., Pleasanton, CA (US); Julio A. Camarero, San Gabriel, CA (US)

(73) Assignee: LAWRENCE LIVERMORE NATIONAL SECURITY, LLC, Livermore, CA (US)

(*) Notice: Subject to any disclaimer, the term of this patent is extended or adjusted under 35 U.S.C. 154(b) by 0 days.

(21) Appl. No.: 15/744,754

(22) PCT Filed: Sep. 9, 2016

(86) PCT No.: PCT/US2016/051172
§ 371 (c)(1),
(2) Date: Jan. 12, 2018

(87) PCT Pub. No.: WO2017/044899
PCT Pub. Date: Mar. 16, 2017

(65) Prior Publication Data
US 2018/0186860 A1 Jul. 5, 2018

Related U.S. Application Data

(60) Provisional application No. 62/217,316, filed on Sep. 11, 2015.

(51) Int. Cl.
| | | |
|---|---|---|
| C07K 14/775 | (2006.01) | |
| C07K 1/00 | (2006.01) | |
| C07K 1/107 | (2006.01) | |
| C07K 1/113 | (2006.01) | |
| G16C 10/00 | (2019.01) | |
| G01Q 60/24 | (2010.01) | |
| B82Y 5/00 | (2011.01) | |

(52) U.S. Cl.
CPC ............ *C07K 14/775* (2013.01); *C07K 1/006* (2013.01); *C07K 1/1077* (2013.01); *C07K 1/113* (2013.01); *B82Y 5/00* (2013.01); *G01Q 60/24* (2013.01); *G16C 10/00* (2019.02)

(58) Field of Classification Search
None
See application file for complete search history.

(56) References Cited

U.S. PATENT DOCUMENTS

| | | |
|---|---|---|
| 4,317,771 A | 3/1982 | Shiba et al. |
| 5,374,715 A | 12/1994 | Kanno et al. |
| 5,393,530 A | 2/1995 | Schneider et al. |
| 6,270,649 B1 | 8/2001 | Zeikus et al. |
| 6,365,191 B1 | 4/2002 | Burman et al. |
| 6,599,527 B1 | 7/2003 | Leigh et al. |
| 7,015,471 B2 | 3/2006 | Franzen et al. |
| 7,048,949 B2 | 5/2006 | Sligar et al. |
| 7,083,958 B2 | 8/2006 | Sligar et al. |
| 7,375,234 B2 | 5/2008 | Sharpless et al. |
| 7,575,763 B2 | 8/2009 | Sligar et al. |
| 7,592,008 B2 | 9/2009 | Sligar et al. |
| 7,622,437 B2 | 11/2009 | Morrissey et al. |
| 7,662,410 B2 | 2/2010 | Sligar et al. |
| 7,691,414 B2 | 4/2010 | Sligar et al. |
| 7,824,709 B2 | 11/2010 | Ryan et al. |
| 8,183,010 B2 | 5/2012 | Swartz et al. |
| 8,268,796 B2 | 9/2012 | Ryan |
| 8,883,729 B2 | 11/2014 | Hoeprich et al. |
| 8,889,623 B2 | 11/2014 | Hoeprich et al. |
| 8,895,055 B2 | 11/2014 | Lam et al. |
| 8,907,061 B2 | 12/2014 | Chromy et al. |
| 9,303,273 B2 | 4/2016 | Hoeprich et al. |
| 9,388,232 B2 | 7/2016 | Dasseux et al. |
| 9,458,191 B2 | 10/2016 | Chromy et al. |
| 9,644,038 B2 | 5/2017 | Luo et al. |

(Continued)

FOREIGN PATENT DOCUMENTS

| | | |
|---|---|---|
| EP | 3426304 A1 | 1/2019 |
| JP | 2008516605 A | 5/2008 |

(Continued)

OTHER PUBLICATIONS

Toniolo et al. (CMLS, Cell. Mol. Life Sci. 58 (2001) 1179-1188).*
Filippis et al. (Enhanced Protein Thermostability by Ala → Aib Replacement, Biochemistry 1998, 37, 1686-1696).*
Ruchela et al. (Oxpholipin 11D: An Anti-Inflammatory Peptide That Binds Cholesterol and Oxidized Phospholipids, PLoS One, Apr. 2010, vol. 5, Issue 4, e10181).*
PDB database search for oxysterol binding protein, retrieved from the Internet: <http://www.rcsb.org/pdb/results/results.do?tabtoshow=Current&qrid=37B93383>, retrieved on Feb. 20, 2020.*

(Continued)

*Primary Examiner* — Suzanne M Noakes
*Assistant Examiner* — Jae W Lee
(74) *Attorney, Agent, or Firm* — Steinfl + Bruno LLP

(57) ABSTRACT

Synthetic apolipoproteins based on native/naturally occurring homolog proteins can be prepared using solid-phase peptide synthesis approaches combined with native chemical ligation methods to create analogs of full length apolipoproteins. The chemical synthesis is expected to allow introduction of non-natural amino acids, e.g., $\alpha,\alpha'$-dialkyl amino acids, with a periodicity that encourages both helix formation and amphipathicity. Such apolipoprotein analogs are expected to encourage, in some embodiments, facile and more complete NLP formation, enabling consideration of full spectrum of nanoparticle-based biotechnology applications ranging from therapeutic sequestration and delivery to energy/biofuel production to biopolymer production.

16 Claims, 11 Drawing Sheets

Specification includes a Sequence Listing.

(56) References Cited

U.S. PATENT DOCUMENTS

| | | | |
|---|---|---|---|
| 9,688,718 | B2 | 6/2017 | Baker et al. |
| 10,151,037 | B2 | 12/2018 | Hoeprich, Jr. et al. |
| 2001/0051131 | A1 | 12/2001 | Unger |
| 2002/0041898 | A1 | 4/2002 | Unger et al. |
| 2003/0008014 | A1 | 1/2003 | Shelness |
| 2004/0101741 | A1 | 5/2004 | Minteer et al. |
| 2004/0180369 | A1 | 9/2004 | Franzen et al. |
| 2005/0182243 | A1 | 8/2005 | Sligar et al. |
| 2005/0244414 | A1 | 11/2005 | Mundy et al. |
| 2006/0013885 | A1 | 1/2006 | Nah et al. |
| 2006/0088524 | A1 | 4/2006 | Morrissey et al. |
| 2006/0127310 | A1 | 6/2006 | Russell-Jones et al. |
| 2006/0127467 | A1 | 6/2006 | Watkin |
| 2006/0189554 | A1 | 8/2006 | Mumper et al. |
| 2006/0211092 | A1 | 9/2006 | Sligar et al. |
| 2007/0101448 | A1 | 5/2007 | Anantharamiah et al. |
| 2007/0117179 | A1 | 5/2007 | Kudlicki et al. |
| 2007/0287034 | A1 | 12/2007 | Minteer et al. |
| 2008/0124350 | A1 | 5/2008 | Mumper et al. |
| 2008/0188399 | A1 | 8/2008 | Sinko et al. |
| 2008/0248565 | A1 | 10/2008 | Katzen et al. |
| 2009/0136937 | A1 | 5/2009 | Coleman et al. |
| 2009/0186393 | A1 | 7/2009 | Baker et al. |
| 2009/0192299 | A1 | 7/2009 | Chromy et al. |
| 2009/0203549 | A1 | 8/2009 | Hoeprich, Jr. et al. |
| 2009/0203706 | A1 | 8/2009 | Zhao et al. |
| 2009/0270331 | A1 | 10/2009 | Remaley et al. |
| 2009/0311276 | A1 | 12/2009 | Hoeprich et al. |
| 2009/0324706 | A1 | 12/2009 | Mirkin et al. |
| 2010/0092567 | A1 | 4/2010 | Hoeprich et al. |
| 2010/0158994 | A1 | 6/2010 | Watkin |
| 2010/0203609 | A1 | 8/2010 | Yacoby et al. |
| 2011/0059549 | A1 | 3/2011 | Coleman et al. |
| 2011/0178029 | A1 | 7/2011 | Knudsen et al. |
| 2011/0178164 | A1 | 7/2011 | Cunha et al. |
| 2011/0195450 | A1 | 8/2011 | Kudlicki et al. |
| 2011/0286915 | A1 | 11/2011 | Lam et al. |
| 2012/0148642 | A1 | 6/2012 | Remaley et al. |
| 2012/0245101 | A1 | 9/2012 | Anantharamiah et al. |
| 2013/0164369 | A1 | 6/2013 | Lam et al. |
| 2013/0165636 | A1 | 6/2013 | Luo et al. |
| 2014/0273142 | A1 | 9/2014 | Hoeprich |
| 2014/0308341 | A1 | 10/2014 | Fujii et al. |
| 2015/0140108 | A1 | 5/2015 | Peer et al. |
| 2016/0083858 | A1 | 3/2016 | Hoeprich, Jr. et al. |
| 2016/0235671 | A1 | 8/2016 | Li et al. |
| 2016/0324923 | A1 | 11/2016 | Dasseux et al. |
| 2018/0079829 | A1 | 3/2018 | Luo et al. |
| 2018/0186860 | A1 | 7/2018 | Hoeprich, Jr. |
| 2018/0318218 | A1 | 11/2018 | Kamrud et al. |
| 2019/0055658 | A1 | 2/2019 | Hoeprich, Jr. et al. |
| 2019/0094230 | A1 | 3/2019 | Coleman et al. |
| 2019/0142752 | A1 | 5/2019 | Blanchette et al. |
| 2019/0307692 | A1 | 10/2019 | Blanchette et al. |
| 2020/0046848 | A1 | 2/2020 | Coleman et al. |

FOREIGN PATENT DOCUMENTS

| | | |
|---|---|---|
| JP | 2015110677 A | 6/2015 |
| WO | 99/59550 A1 | 11/1999 |
| WO | 00/65099 A1 | 11/2000 |
| WO | 02/40501 A2 | 5/2002 |
| WO | 2004/094651 A2 | 11/2004 |
| WO | 2004/112214 A2 | 12/2004 |
| WO | 2005/070400 A1 | 8/2005 |
| WO | 2006/073419 A2 | 7/2006 |
| WO | 2007/038755 A1 | 4/2007 |
| WO | 2007/050501 A2 | 5/2007 |
| WO | 2007/053655 A2 | 5/2007 |
| WO | 2008/028206 A2 | 3/2008 |
| WO | 2008/106660 A2 | 9/2008 |
| WO | 2009/100201 A2 | 8/2009 |
| WO | 2010/039496 A2 | 4/2010 |
| WO | 2010/040897 A1 | 4/2010 |
| WO | 2014/063097 A1 | 4/2014 |
| WO | 2017/035326 A1 | 3/2017 |
| WO | 2017/044899 A1 | 3/2017 |
| WO | 2017/155837 A1 | 9/2017 |
| WO | 2018/204421 A2 | 11/2018 |

OTHER PUBLICATIONS

Bacher G., et al., "Charge-reduced Nano Electrospray Ionization Combined with Differential Mobility Analysis of Peptides, Proteins, Glycoproteins, Noncovalent Protein Complexes and Viruses," Journal of Mass Spectrometry, Sep. 2001, vol. 36 (9), 1038-1052. 15 pages.

Baker S.E., et al., "Hydrogen Production by a Hyperthermophilic Membrane-Bound Hydrogenase in Water Soluble Nanolipoprotein Particles," Journal of the American Chemical Society, Nov. 18, 2008, vol. 131 (22), 15 pages.

Barros F., et al., "Modulation of Human erg K+ Channel Gating by Activation of a G Protein-Coupled Receptor and Protein Kinase C," The Journal of Physiology, Sep. 1998, vol. 511 (Pt 2), 333-346. 14 pages.

Bayburt T.H., et al., "Self-Assembly of Discoidal Phospholipid Bilayer Nanoparticles with Membrane Scaffold Proteins," Nano Letters, 2002, vol. 2 (8), 853-856. 11 pages (Additional Pages of Accompanying Online Supplementary Information).

Behrens S., et al., "Linking Microbial Phylogeny to Metabolic Activity at the Single-cell Level by Using Enhanced Element Labeling-Catalyzed Reporter Deposition Fluorescence in Situ Hybridization (EL-FISH) and Nanosims," Applied and Environmental Microbiology, May 2008, vol. 74 (10), 3143-3150. 8 pages.

Berthelot K., et al., "Rubber Elongation Factor (REF), a Major Allergen Component in Hevea Brasiliensis Latex Has Amyloid Properties," PLoS One, 2012, vol. 7 (10), e48065. 12 pages.

Bijsterbosch M.K., et al., "Specific Targeting of a Lipophilic Prodrug of Iododeoxyuridine to Parenchymal Liver Cells Using Lactosylated Reconstituted High Density Lipoprotein Particles," Biochemical Pharmacology, Jul. 1996, vol. 52 (1), 113-121. 10 pages.

Bischler N., et al., "Specific Interaction and Two-Dimensional Crystallization of Histidine Tagged Yeast RNA Polymerase I on Nickel-Chelating Lipids," Biophysical Journal, Mar. 1998, vol. 74 (3), 1522-1532. 11 pages.

Blanchette C.D., et al., "Quantifying Size Distributions of Nanolipoprotein Particles With Single-particle Analysis and Molecular Dynamic Simulations," Journal of Lipid Research, Jul. 2008, vol. 49 (7), 11 pages.

Borch J., et al., "Nanodiscs for Immobilization of Lipid Bilayers and Membrane Receptors: Kinetic Analysis of Cholera Toxin Binding to a Glycolipid Receptor," Analytical Chemistry, Aug. 2008, vol. 80 (16), 8 pages.

Boroske E., et al., "Osmotic Shrinkage of Giant Egg-Lecithin Vesicles," Biophysical Journal, Apr. 1981, vol. 34 (1), 95-109, 15 pages.

Boschker H.T.S., et al., "Direct Linking of Microbial Populations to Specific Biogeochemical Processes by 13C-Labelling of Biomarkers," Nature, Apr. 1998, vol. 392, 801-805. 5 pages.

Branden et al., "Introduction to Protein Structure," 2nd edition, Garland Science Publisher, 1999, pp. 3-12. 11 pages.

Brewer S.H., et al., "Formation of Thioate and Phosphonate Adlayers on Indium-Tin Oxide: Optical and Electronic Characterization," Langmuir, 2002, vol. 18 (18), 6857-6865. 9 pages.

Brodie E.L., et al., "Application of a High-Density Oligonucleotide Microarray Approach To Study Bacterial Population Dynamics during Uranium Reduction and Reoxidation," Applied and Environmental Microbiology, Sep. 2006, vol. 72 (9), 6288-6298. 11 pages.

Brodie E.L., et al., "Profiling Microbial Identity and Activity: Novel Applications of NanoSIMS and High Density Microarrays," Systems Biology Research Strategy & Technology Development, Genomics: GTL Awardee Workshop VI, Department of Energy, 2008, 2 pages.

Brodie E.L., et al., "Urban Aerosols Harbor Diverse and Dynamic Bacterial Populations," Proceedings of the National Academy of Sciences of the United States of America, Jan. 2007, vol. 104 (1), 299-304. 6 pages.

(56) References Cited

OTHER PUBLICATIONS

Brodie et al., Systems Biology Research Strategy and Technology Development: Genomic and Proteomic Strategies. Publicly disclosed on Feb. 13, 2008, http://genomicscience.energy.gov/pubs/2008abstracts/2008GTLabstractstech.pdf, 48 pages.
Brown P.O., et al., "Exploring the New World of the Genome with DNA Microarrays," Nature Genetics, Jan. 1999, vol. 21 (1 Suppl), 33-37. 5 pages.
"Catalytic oxygen removal from coal mine methane," http://www.digitalrefining.com/article/1000623,Catalytic_oxygen_removal_from_coal_mine_methane.html# . . . , accessedNov. 27, 2017, 4 pages.
Chaung H.C., et al., "CpG Oligodeoxynucleotides as DNA Adjuvants in Vertebrates and their Applications in Immunotherapy," International Immunopharmacology, Oct. 2006, vol. 6 (10), 1586-1596. 11 pages.
Chikh G.G., et al., "Attaching Histidine-Tagged Peptides and Proteins to Lipid-Based Carriers Through Use of Metal-Ion-Chelating Lipids," Biochimica et Biophysica Acta, Dec. 2002, vol. 1567 (1-2), 204-212. 9 pages.
Cline M.S., et al., "Integration of Biological Networks and Gene Expression Data Using Cytoscape," Nature Protocols, 2007, vol. 2 (10), 2366-2382. 17 pages.
Cornish K., "Biochemistry of Natural Rubber, a Vital Raw Material, Emphasizing Biosynthetic Rate, Molecular Weight and Compartmentalization, in Evolutionarily Divergent Plant Species," Natural Product Reports, Apr. 2001, vol. 18 (2), 182-189. 8 pages.
Co-Translation of Iintegral Membrane Proteins (MP) with Membrane Scaffoldproteins (MSP), also known as Nanodiscs[online], Jul. 2015 [ retrieved on Jul. 1, 2015], Retrieved from the internet: URL: http://technology.sbkb.org/portal/page/329/, 3 pages.
Cracknell J.A., et al., "Enzymatic Oxidation of H2 in Atmospheric O2: The Electrochemistry of Energy Generation from Trace H2 by Aerobic Microorganisms," Journal of the American Chemical Society, Jan. 2008, vol. 130 (2), 424-425. 2 pages.
Cravatt B.R., et al., "Large-Scale Profiling of Protein Palmitoylation in Mammalian Cells," Nature Methods, Feb. 2009, vol. 6 (2), 135-138. 4 pages.
Cube Biotech, "Assembly of Nanodiscs for use in Cell-Free Expression using MSP1D1 Protein and POPC Phospholipids," 2014, 3 pages.
Cube Biotech, "Nanodisc Assembly Kit MSP1E3D1_POPC," Dec. 2014, 3 pages.
Dalpke A.H., et al., "Phosphodiester CpG Oligonucleotides as Adjuvants:Polyguanosine Runs Enhance Cellular Uptake and improve Immunostimulative Activity of Phosphodiester CpG Oligonucleotides in Vitro and in Vivo," Immunology, May 2002, vol. 106 (1), 102-112. 11 pages.
Das D., et al., "Hydrogen Production by Biologicai Processes: A Survey of Literature," International Journal of Hydrogen Energy, Jan. 2001, vol. 26 (1), 13-28. 16 pages.
Desantis T.Z., et al., "Greengenes, a Chimera-checked 16S rRna Gene Database and Workbench Compatible with ARB," Applied and Environmental Microbiology, Jul. 2006, vol. 72 (7), 5069-5072. 5 pages.
Desantis T.Z., et al., "High-Density Universal 16S rRNA Microarray Analysis Reveals Broader Diversity than Typical Clone Library When Sampling the Environment," Microbial Ecology, Apr. 2007, vol. 53 (3), 371-383. 13 pages.
DiSalvo E.A., et al., "Surface Changes induced by Osmotic Shrinkage on Large Unilamellar Vesicles," Chemistry and Physics of Lipids, Nov. 1996, vol. 84 (1), 35-45. 11 pages.
Duan H., et al., "Co-Incorporationof Heterologously Expressed *Arabidopsis* Cytochrome P450 and P450 Reductase into Soluble Nanoscale Lipid Bilayers," Archives of Biochemistry and Biophysics, Apr. 2004, vol. 424 (2), 141-153. 13 pages.
Dumartin B., et al., "Dopamine Tone Regulates D1 Receptor Trafficking and Delivery in Striatal Neurons in Dopamine Transporter-Deficient Mice," Proceedings of the National Academy of Sciences of the United States of America, Feb. 2000, vol. 97 (4), 1879-1884. 6 pages.
Eberly J.O., et al., "Thermotolerant Hydrogenases: Biological Diversity, Properties and Biotechnical Applications," Critical Reviews in Microbiology, Dec. 2003, vol. 34 (3-4), 117-130. 14 pages.
Final Office Action for U.S. Appl. No. 14/861,750, dated Feb. 23, 2018, 21 pages.
Fischer N.O., et al., "Conjugation to Nickel-Chelating Nanolipoprotein Particles Increases the Potency and Efficacy of Subunit Vaccines to Prevent West Nile Encephalitis," Bioconjugate Chemistry, Jun. 2010, vol. 21 (6), 1018-1022. 5 pages.
Fischer N.O., et al., "Evaluation of Nanoliooprotein Particles (NLPs) as an In Vivo Delivery Platform," PLoS One, Mar. 2014, vol. 9 (3), e93342, 1-17. 17 pages.
Fischer N.O., et al., "Immobilization of His-Tagged Proteins on Nickel-Chelating Nanolipoprotein Particles," Bioconjugate Chemistry, Mar. 2009, vol. 20 (3), 460-465. 6 pages.
Fitzgerald K.A., et al., "The Shape of Things to Come," Science, Jun. 2007, vol. 316 (5831), 1574-1576, 4 pages.
Gantz I., et al., "Molecular Cloning of a Gene Encoding the Histamine H2 Receptor," Proceedings of the National Academy of Sciences of the United States of America, Jan. 1991, vol. 88 (2), 429-433. 6 pages.
Gardner T.J., et al., "Systems for Orthogonal Self-assembly of Electroactive Monolayers on Au and ITO: an Approach to Molecular Electronics," Journal of American Chemical Society, Jul. 1995, vol. 117 (26), 6927-6933. 7 pages.
Giannini S.L., et al., "Enhanced Humoral and Memory B Cellular Immunity Using HPV16/18 L1 VLP Vaccine Formulated With the MPL/aluminium Salt Combination (AS04) Compared to Aluminium Salt Only," Vaccine Aug. 2006, vol. 24 (33-34), 13 pages.
Goldet G., et al., "Hydrogen Production under Aerobic Conditions by Membrane-Bound Hydrogenases from *Ralstonia* Species," Journal of American Chemical Society, Jul. 2008, vol. 130 (33), 9 pages.
Guo H.H., et al., "Protein Tolerance to Random Amino Acid Change," *Proceedings of the National Academy of Sciences of the United States of America*, Jun. 2004, vol. 101 (25), 6 pages.
Gupta R.K ., et al., "Adjuvants for Human Vaccines—current Status, Problems and Future Prospects," Vaccine,Oct. 1995, vol. 13 (14), 14 pages.
Hamdy S., et al., "Pharmaceutical Analysis of Synthetic Lipid a-based Vaccine Adjuvants in Poly (D, L-lactic-co-glycolic Acid) Nanoparticle Formulations," Journal of Pharmaceutical and Biomedical Analysis,Aug. 2007, vol. 44 (4), 10 pages.
Abdulreda M.H., et al., "Atomic Force Microscope Spectroscopy Reveals a Hemifusion Intermediate during Soluble N-Ethylmaleimide-Sensitive Factor-Attachment Protein Receptors-Mediated Membrane Fusion," Biophysical Journal, Jan. 2008, vol. 94 (2), 648-655, 8 pages.
Abdulreda M.H., et al., "Atomic Force Microscope Studies of the Fusion of Floating Lipid Bilayers," *Biophysical Journal*,Jun. 2007, vol. 92 (12), 10 pages.
Advisory Action for U.S. Appl. No. 12/118,396, filed May 9, 2008, dated Jul. 7, 2015, 8 pages.
Advisory Action for U.S. Appl. No. 12/118,396, dated Jun. 7, 2012, 5 pages.
Advisory Action for U.S. Appl. No. 12/118,530, dated Jul. 23, 2015, 13 pages.
Advisory Action for U.S. Appl. No. 12/118,530, dated Jun. 6, 2012, 5 pages.
Aranyi T., et al., "Predictable Difficulty or Difficulty to Predict," *Protein Science*,Jan. 2011, vol. 20 (1), 3 pages.
Bacher G., et al., "Negative and Positive Ion Matrix-Assisted Laser Desorption/Ionization Time-of-Flight Mass Spectrometry and Positive Ion Nano-Eiectrospray Ionization Quadrupole Ion Trap Mass Spectrometry of Peptidoglycan Fragments Isolated from Various *Bacillus* Species," *Journal of Mass Spectrometry*,Feb. 2001, vol. 36 (2), 16 pages.
Bao P., et al., "High-Sensitivity Detection of DNA Hybridization on Microarrays Using Resonance Light Scattering," *Analytical Chemistry*,Apr. 2002, vol. 74 (8), 6 pages.

(56) References Cited

OTHER PUBLICATIONS

Bay et al., "Small multidrug resistance proteins: A multidrug transporter family that continues to grow," Biochimica et Biophysica Acta 1778 (2008) 1814-1838.

BEJA O., et al., "Bacterial Rhodopsin: Evidence for a New Type of Phototrophy in the Sea," Science,Sep. 2000, vol. 289 (5486), 6 pages.

Blanchette C.D., et al., "Characterization and Purification of Polydisperse Reconstituted Lipoproteins and Nanolipoprotein Particles," International Journal of Molecular Sciences,Jul. 2009, vol. 10 (7), 14 pages.

Bockaert J., et al., "Do Recombinant Receptor Assays Provide Affinity and Potency Estimates?," In Receptor Classification: The Integration of Operational, Structural, and Transductional Information,1997, vol. 812, New York, New York Academy of Sciences, 16 pages.

Boschker H.T.S., et al., "The Contribution of Macrophyte-derived Organic Matter to Microbial Biomass in Salt-marsh Sediments: Stable Carbon Isotope Analysis of Microbial Biomarkers," Limnology and Oceanography, 1999, vol. 44(2), 309-319. 11 pages.

Chen J.S., et al., "Amino Acids in SRS1 and SRS6 Are Critical for Furanocoumarin Metabolism by CYP6B1V1 , a Cytochrome P450 Monooxygenase," Insect Molecular Biology,Apr. 2002, vol. 11 (2), 12 pages.

Claypool et al., An ethanol/ethersoluble apoprotein from rat lung surfactant augments liposome uptake by isolated granular pneumocytes. J Clin Invest. Sep. 1984; 74(3): 677-84. (Year: 1984). 8 pages.

Cleveland, T.E. IV, et al., "Small-angle X-ray and neutron scattering demonstrates that cell-free expression produces properly formed disc-shaped nanolipoprotein particles," Protein Science , Dec. 2017, vol. 27, pp. 780-789.

Coleman M., et al., "Asp 46 Can Substitute for Asp 96 as the Schiff Base Proton Donor in Bacteriorhodopsin," Biochemistry,Nov. 1995, vol. 34 (47), 8 pages.

Crankshaw C., Nanodisc Technology: A Revolutionary System for Study of Membrane Proteins, Biofiles,retrieved on Mar. 4, 2015, Retrieved from the Internet: URL: http://www.sigmaaldrich.com/tecimical-documents/articleslbiofiles/nanodisc-technology.html, vol. 8, No. 20, 3 pages.

Cullis P.R., et al., "Physical Properties and Functional Roles of Lipids in Membranes," New Comprehensive Biochemistry, 1991, vol. 20, 41 pages.

Definition of "homogeneous", Oxford Dictionaries, retrieved from https://en.oxforddictionaries.com/definition/homogeneous on Apr. 4, 2018, four pages.

Definition of Hydrogenase[online], Nov. 6, 2012[retrieved on Nov. 6, 2012], Retrieved from Internet: URL: en.wikipedia.org/wiki/Hydrogenase, 4 pages.

Denisov I.G., et al., "Nanodiscs in Membrane Biochemistry and Biophysics", Chemical Reviews, Mar. 2017, vol. 117(6), 4669-4713. 92 pages.

Dong, C., et al., "Regulation of G protein-coupled receptor export trafficking," Biochimica et Biophysics Acta 1768 (2006) 853-870.

Dong F., et al., "Endothelin-1 Enhances Oxidative Stress, Cell Proliferation and Reduces Apoptosis in Human Umbilical Vein Endothelial Cells: Role of ETB Receptor, NADPH oxidase and caveolin-1" British Journal of Pharmacology, Jun. 2005, vol. 145 (3), 323-333. 11 pages.

Dunn R.J., et al., "Structure-functions Studies on Bacteriorhodopsin," The Journal of Biological Chemistry,1987, vol. 262 (19), 9 pages.

Final Office Action for U.S. Appl. No. 12/118,396, dated Feb. 4, 2015, 29 pages.

Final Office Action for U.S. Appl. No. 12/118,396, dated Jan. 18, 2012, 17 pages.

Final Office Action for U.S. Appl. No. 12/118,396, dated Oct. 11, 2016, 29 pages.

Final Office Action for U.S. Appl. No. 12/118,396, dated Apr. 12, 2018. 25 pages.

Final Office Action for U.S. Appl. No. 12/118,530, dated Jan. 25, 2012, 37 pages.

Final Office Action for U.S. Appl. No. 12/118,530, dated Mar. 6, 2015, 51 pages.

Forte T.M., et al., "Electron Microscope Study on Reassembly of Plasma High Density Apoprotein with Various Lipids," Biochimica et Biophysica Acta,Nov. 1971, vol. 248 (2), 6 pages.

G Protein-coupled Receptor[online], Retrieved from the Internet: URL: Wikipedia 2008, https://web.archive.org/web/20080224232212/:///en.wikipedia.org/wiki/G.protein-coupled.receptor, 2008, 7 pages.

Gao, T., et al., (2011) "Characterizing diffusion dynamics of a membrane protein associated with nanolipoproteins using fluorescence correlation spectroscopy," Protein Science. 20:437-447.

Gao, T., et al., "Characterization of de novo synthesized GPCRs supported in nanolipoprotein discs," (2012) E.Pub, PloS One. 7(9):44911. 8 pages.

He, W., "Controlling the Diameter, Monodispersity and Solubility of ApoA1 Nanolipoprotein Particles using Telodendrimer Chemistry," (2013) Protein Science 22, 1078-1086.

Howland M.C. et al., "Model Studies of Membrane Disruption by Photogenerated Oxidative Assault." The Journal of Physical Chemistry, 2010. 114(19); p. 6377-6385.

International Preliminary Report on Patentability (Chapter 1) for International Application No. PCT/US2017/020827 filed on Mar. 3, 2017 on behalf of Lawrence Livermore National Laboratory dated Sep. 11, 2018 9 pages.

International Preliminary Reporton Patentability for Application No. PCT/US2008/063307, dated Nov. 10, 2009, 7 pages.

International Search Report for Application No. PCT/US2008/063307, dated Oct. 29, 2008, 5 pages.

International Search Report for International Application No. PCT/US2017/020827 filed on Mar. 3, 2017 on behalf of Lawrence Livermore National Laboratory dated Jun. 20, 2017 4 pages.

"Ion channel", Wikipedia, accessed Dec. 22, 2014, pp. 1-8, 8 pages.

Kalmbach R., et al., "Functional Cell-free Synthesis of a Seven Helix Membrane Protein: In Situ insertion of Bacteriorhodopsin in Liposomes," Journal of Molecular Biology,Aug. 2007, vol. 371 (3), 10 pages.

Kim, J-M., et al. "Immobilized Polydiacetylene Vesicles on Solid Substrates for Use as Chemosensors." Advanced Materials15(13), 1118-1121, (Jul. 2003), 4 pages.

Kim Y.P., et al., "Gold Nanoparticle-enhanced Secondary Ion Mass Spectrometry Imaging of Peptides on Self-assembled Monolayers," Analytical Chemistry,Mar. 2006, vol. 78(6), 8 pages.

Klammt C., et al., "Cell-free Expression as an Emerging Technique for the Large Scale Production of Integral Membrane Protein," The FEBS Journal,Sep. 2006, vol. 273 (18), 13 pages.

Kreshech G.C. "Surfactants in Water—A Comprehensive Treatise." 1975: Plenum, New York.

Lee J., et al., "Ab Initio Protein Structure Prediction: in From Protein Structure to Function with Bioinformatics," Springer Science + Business Media B. V.,2009, 23 pages.

Loll, PJ, "Membrane protein structural biology: the high throughput challenge", J. of Structural Biology, 142:144-153; 2003.

Lu B., et al., "Conformational Reorganization of the Four-helix Bundle of Human Apolipoprotein E in Binding to Phospholipid," The Journal of Biological Chemistry, Jul. 2000, vol. 275 (27), 7 pages.

Ly, S., et al., (Jan. 2014) "Quantifying interactions of a membrane protein embedded in lipid nanodisc using fluorescence correlation spectroscopy," Biophysical Journal. 106: L05-L08.

Ly, S., et al., "Quantifying membrane protein interactions in solution using fluorescence correlation spectroscopy," Biophysical Journal, (Aug. 15, 2013), LLNL-JRNL-642412. Lawrence Livermore National Laboratory. 11 pages.

Non-Final Office Action for U.S. Appl. No. 12/118,396, dated Aug. 30, 2011, 18 pages.

Non-Final Office Action for U.S. Appl. No. 12/118,396, dated Jan. 8, 2016, 32 pages.

Non-Final Office Action for U.S. Appl. No. 12/118,396, dated Jul. 22, 2014, 28 pages.

Non-Final Office Action for U.S. Appl. No. 12/118,396, dated Sep. 6, 2017, 14 pages.

Non-Final Office Action for U.S. Appl. No. 12/118,530, dated Aug. 30, 2011, 28 pages.

(56) References Cited

OTHER PUBLICATIONS

Non-Final Office Action for U.S. Appl. No. 12/118,530, dated Jul. 24, 2014, 33 pages.
North P., et al., "Alteration of Synaptic Membrane Cholesterol/Phospholipid Ratio Using a Lipid Transfer Protein, Effect on Gamma-aminobutyric Acid Uptake," *The Journal of Biological Chemistry*,Jan. 1983, vol. 258 (2), 12 pages.
Pasini E.M., et al., "In-Depth Analysis of the Membranes and Cytosolic Proteome of Red Blood Cells," Blood, Aug. 2006, vol. 180 (3), 12 pages.
Restriction Requirement for U.S. Appl. No. 12/118,396, dated Mar. 4, 2011, 14 pages.
Restriction Requirement for U.S. Appl. No. 12/118,530, filed May 9, 2008, dated Sep. 24, 2010, 14 pages.
Restriction Requirement for U.S. Appl. No. 12/118,530, dated Mar. 30, 2011, 28 pages.
Restriction Requirement for U.S. Appl. No. 16/082,924 filed on Sep. 2018 on behalf of Lawrence Livermore National Laboratory dated Oct. 24, 2019 9 pages.
Rusiñol A.E., et al., "In Vitro Reconstitution of Assembly of Apolipoprotein B48-Containing Lipoproteins," *The Journal of Biological Chemistry*,Mar. 21, 1997, vol. 272(12), 7 pages.
Segelke B.W., et al., "Laboratory Scale Structural Genomics," *Journal of Structural and Functional Genomics*,2004, vol. 5(1-2), 11 pages.
Shih A.Y., et al., "Disassembly of Nanodiscs with Cholate",*Nano Letters*,Jun. 2007, vol. 7 (6), 5 pages.
Shih A.Y., et al., "Molecular Dynamics Simulations of Discoidal Bilayers Assembled from Truncated Human Lipoproteins," *Biophysical Journal*, Jan. 2005, vol. 88 (1), 9 pages.
Sonar S., et al., "A Redirected Proton Pathway in the Bacteriorhodopsin Mutan Tyr-57—Asp. Evidence for Proton Translocation Without Schiff Base Deprotonation," *The Journal of Biological Chemistry*,Nov. 1994, vol. 269 (46), 8 pages.
Sonar S., et al., "Cell-Free Synthesis, Functional Refolding and Spectroscopic Characterization of Bacteriorhodopsin, an Integral Membrane Protein," *Biochemistry*,Dec. 1993, vol. 32 (50), 5 pages.
Sun P.D., et al., "Overview of Protein Structural and Functional Folds," *Current Protocols in Protein Science*,May 2004, vol. 35, 3 pages.
Swaney J.B., "Properties of Lipid-apolipoprotein Association Products. Complexes of Human Apo AI and Binary Phospholipid Mixtures," *Journal of Biological Chemistry*,Sep. 1980 vol. 255, vol. 18, pp. 8798-8803.
Walter P., et al., "Preparation of Microsomal Membranes for Cotranslational Protein Translocation," *Methods in Enzymology*,vol. 96, 10 pages.
Wang J., et al., "Comparison of the Dynamics of the Primary Events of Bacteriorhodopsin in its Trimeric and Monomeric States," *Biophysical Journal*,Sep. 2002, vol. 83 (3), 10 pages.
Wetterau J.R., et al., "Effect of Dipalmitoylphosphatidylcholine Vesicle Curvature on the Reaction With Human Apolipoprotein A-I," *The Journal of Biological Chemistry*,Sep. 1982, vol. 257 (18), 7 pages.
Wientzek M., et al., "Binding of Insect Apolipophorin III to Dimyristoylphosphatidylcholine Vesicles. Evidence for a Conformational Change," *Journal of Biological Chemistry*, Feb. 1994, vol. 269 (6), 8 pages.
Written Opinion for Application No. PCT/US2008/063307, dated Oct. 29, 2808, 6 pages.
Written Opinion for International Application No. PCT/US2017/020827 filed on Mar. 3, 2017 on behalf of Lawrence Livermore National Laboratory dated Jun. 20, 2017 8 pages.
Wuu J.J., et al., "High Yield Cell-Free Production of Integral Membrane Proteins without Refolding or Detergents," *Biochimica et Biophysics Acta*,May 2008, vol. 1778 (5), 14 pages.
Badamchi-Zadeh A, et al., "A multi-component prime-boost vaccination regimen with a consensus MOMP antigen enhances chlamydia trachomatis clearance." Frontiers In Immunology, vol. 7, Article 162, pp. 1-11 (Apr. 2016).
Baehr W, et al., "Mapping antigenic domains expressed by Chlamydia trachomatis major outer membrane protein genes." Proceeding of the National Academy of Sciences, vol. 85, pp. 4000-4004 (1988).
Baughman, R.H. "Solid-state polymerization of diacetylenes." *Journal of Applied Physics*43(11), 4362-4370,(Nov. 1972). 10 pages.
Carmichael J.R. et al., "Induction of protection against vaginal shedding and infertility by recombinant Chlamydia vaccine" *Vaccine*, 29,pp. 5276-5283 (2011).
Coleman M.A, et al., "Expression and Association of the Yersinia pestis Translocon Proteins, YopB and YopD, Are Facilitated by Nanolipoprotein Particles." *PLoS One*p.e0150166 (2016). 16 pages.
Conlan J, et al., "Isolation of recombinant fragments of the major outer-membrane protein of Chlamydia trachomatis: their potential as subunit vaccines" Microbiology, 136, pp. 2013-2020(1992).
Das A. et al., "Screening of Type I and II Drug Binding to Human Cytochrome P450-3A4 in Nanodiscs by Localized Surface Plasmon Resonance Spectroscopy." Analytical Chemistry, 2009. 81(10): p. 3754-3759.
Davidson E, et al., "A high-throughput shotgun mutagenesis approach to mapping B-cell antibody epitopes" Immunology, 143, pp. 13-20 (2014).
Dengue Fever Climbs the Social Ladder, Special Report, *Nature*, Aug. 2007, vol. 448, 2 pages.
Farris C.M. et al., "CD4+ T cells and antibody are reguired for optimal major outer membrane protein vaccine-induced immunity to Chlamydia muridarum genital infection" Infection and Immunity, vol. 78, No. 10, pp. 4374-4383 (2010).
Feher V.A. et al., "A 3-dimensional trimeric B-barrel model for Chlamydia MOMP contains conserved and novel elements of Gram-negative bacterial porins." PloS One p. e68934, vol. 8, Issue 7 (2013). 11 pages.
Ferrara L.G.M. et al., "MOMP from Campylobacter jejuni Is a Trimerof 18-Stranded beta-Barrel Monomers with a Ca(2+) Ion Bound at the Constriction Zone." J Mol Biol(2016), 428(22), pp. 4528-4543. 16 pages.
Final Office Action for U.S. Appl. No. 12/469,533, dated Dec. 4, 2012, 7 pages.
Final Office Action for U.S. Appl. No. 12/469,533, dated Oct. 24, 2011, 11 pages.
Findlay H.E, et al., "Surface expression, single-channel analysis and membrane topology of recombinant Chlamydia trachomatis Major Outer Membrane Protein" *BMC Microbiol*, 5:5 (2005). 15 pages.
Fischer, N.O., et al. "Colocalized Delivery of Adjuvant and Antigen Using Nanolipoprotein Particles Enhances the Immune Response to Recombinant Antigens." *Journal of the American Chemical Society*135(6), 2044-2047, (Jan. 2013). 4 pages.
Fischer N.O. et al., "Isolation, characterization, and stability of discretely-sized nanolipoprotein particles assembled with Apolipophorin-III" PLoS One, 2010, vol. 5, No. 7, e11643.
Frias, J.C., et al. "Properties of a Versatile Nanoparticle Platform Contrast Agent To Image and Characterize Atherosclerotic Plagues by Magnetic Resonance Imaging." *Nano Letters*6(10), 2220-2224, (Jul. 2006). 5 pages.
Georger, J.H., et al. "Helical and Tubular Microstructures Formed by Polymerizable Phosphatidylcholines." *Journal of American Chemical Society*109(20), 6169-6175, (Sep. 1987). 7 pages.
Haque F, et al., "Incorporation of a viral DNA-packaging motor channel in lipid bilayers for real-time, single-molecule sensing of chemicals and double-stranded DNA." Nat Protoc, vol. 8, No. 2, pp. 373-392 (2013).
Hayward, J.A., et al. "Biomembrane surfaces as models for polymer design: the potential for haemocompatibility." *Biomaterials*5(3), 135-142, (May 1984). 8 pages.
He W, et al., "Cell-free expression of functional receptor tyrosine kinases" *Sci Rep*, 5:12896 (2015). 8 pages.
He W, et al., "Producing Membrane Bound Proteins as Countermeasures to infectious Diseases" Synthetic Genomics Vaccines (2016).
Inic-Kanada A, et al., "A Probiotic Adjuvant Lactobacillus rhamnosus Enhances Specific Immune Responses after Ocular Mucosal Immunization with Chlamydial Polymorphic Membrane Protein C." PLoS One p. e015785 (2016) 14 pages.

(56) References Cited

OTHER PUBLICATIONS

International Preliminary Report on Patentability (Chapter 1) for International Application No. PCT/US2016/048632 filed on Aug. 25, 2016 on behalf of Lawrence Livermore National Laboratory dated Feb. 27, 2018 11 pages.
International Preliminary Report on Patentability for International Application No. PCT/US2018/030537 filed on May 1, 2018 on behalf of Lawrence Livermore National Security, dated Nov. 14, 2019. 11 pages.
International Search Report for International Application No. PCT/US2016/048632 filed on Aug. 25, 2016 on behalf of Lawrence Livermore National Laboratory dated Feb. 6, 2017 5 pages.
International Search Report for International Application No. PCT/US2018/030537 filed on May 1, 2018 on behalf of Lawrence Livermore National Security dated Jan. 17, 2019 5 pages.
Jia, J., et al. "Preparation, Characterizations, and In Vitro Metabolic Processes of Paclitaxel-Loaded Discoidal Recombinant High-Density Lipoproteins." *Journal of Pharmaceutical Sciences* 101(8), 2900-2908, (Aug. 2012). 9 pages.
Johnson R.M. et al., "PmpG 303-311, a protective vaccine epitope that elicits persistent cellular immune responses in Chlamydia muridarum-immune mice." Infect Immun, vol. 80, No. 6, p. 2204-2211 (2012).
Johnston, D.S., et al. "Phospholipid Polymers—Synthesis and Spectral Characteristics." *Biochimica et Biophysica Acta* 602(1), 57-69, (Oct. 1980). 13 pages.
Jonsson, M.P., et al. "Supported Lipid Bilayer Formation and Lipid-Membrane-Mediated Biorecognition Reactions Studied with a New Nanoplasmonic Sensor Template." *Nano Letters* 7(11), 3462-3468, (Sep. 2007). 7 pages.
Karunakaran K.P. et al., "Immunoproteomic discovery of novel T cell antigens from the obligate intracellular pathogen Chlamydia" J Immunol p. 2459-65 (2008).
Karunakaran K.P. et al., "Outer membrane proteins preferentially load MHC class II peptides: implications for a Chlamydia trachomatis T cell vaccine." Vaccine, 33, p. 2159-2166 (2015).
Koren E, et al., "Clinical validation of the "in silico" prediction of immunogenicity of a human recombinant therapeutic protein" Clinical Immunology, 124, pp. 26-32 (2007).
Lamparski, H., et al. "Two-Dimensional Polymerization of Lipid Bilayers Degree of Polymerization of Sorbyl Lipids." *Macromolecules* 28(6), 1786-1794, (Mar. 1995). 9 pages.
Lei, J., et al. "Two-Dimensional Polymerization of Lipid Bilayers: Rate of Polymerization of Acryloyl and Methacryloyl Lipids." *Macromolecules* 27(6), 1381-1388, (Mar. 1994). 8 pages.
Lieser, G., et al. "Structure, Phase Transitions and Polymerizability of Multilayers of some Diacetylene Monocarboxylic Acids." Thin Solid Films 68(1), 77-90, (May 1980). 14 pages.
Manning D.S et al., "Expression of the major outer membrane protein of Chlamydia trachomatis in *Escherichia coli*." Infection and Immunity, vol. 61, No. 10, pp. 4093-4098 (1993).
Mao H.B. et al., "Design and characterization of immobilized enzymes in microfluidic systems." Analytical Chemistry, 2002. 74(2): p. 379-385.
Morigaki, K., et al. "Surface Functionalization of a Polymeric Lipid Bilayer for Coupling a Model Biological Membrane with Molecules, Cells, and Microstructures." *Langmuir* 29(8), 2722-2730, (Jan. 2013). 9 pages.
Non-Final Office Action for U.S. Appl. No. 12/469,533, dated May 23, 2012, 15 pages.
Notice of Allowance for U.S. Appl. No. 12/469,533, dated Jul. 3, 2014, 13 pages.
Ohno, H., et al. "Polymerization of Liposomes Composed of Diene-Containing Lipids by UV and Radical Initiators: Evidence for the Different Chemical Environment of Diene Groups on 1- and 2-Acyl Chains." *Macromolecules* 20(5), 929-933, (May 1987). 5 pages.
Okahata Y. et al., "Polymerizable lipid-corked capsule membranes. Polymerization at different positions of corking lipid bilayers on the capsule and effect of polymerization on permeation behavior." *Journal of the American Chemical Society*, 1988, vol. 110, No. 8, pp. 2495-2500.
Okazaki, T., et al. "Phase Separation of Lipid Microdomains Controlled by Polymerized Lipid Bilayer Matrices." *Langmuir* 26(6), 4126-4129, (Dec. 2009). 4 pages.
Okazaki T. et al., "Polymerized lipid bilayers on a solid substrate: Morphologies and obstruction of lateral diffusion." Langmuir, 2009. 25(1): p. 345-351.
Pal S, et al., "Comparison of the nine polymorphic membrane proteins of Chlamydia trachomatis for their ability to induce protective immune responses in mice against a C. muridarum challenge." Vaccine, 35, p. 2543-2549 (2017).
Pal S, et al., "Immunization with an acellular vaccine consisting of the outer membrane complex of Chlamydia trachomatis induces protection against a genital challenge" Infection and Immunity, vol. 65, No. 8, pp. 3361-3369 (1997).
Pal S, et al., "Immunization with the Chlamydia trachomatis mouse pneumonitis major outer membrane protein can elicit a protective immune response against a genital challenge" Infection and immunity, vol. 65, No. 10, pp. 6240-6247 (2001).
Pal S, et al., "Vaccination with the Chlamydia trachomatis major outer membrane protein can elicit an immune response as protective as that resulting from inoculation with live bacteria" Infection and Immunity, vol. 73, No. 12, pp. 8153-8160 (2005).
Patel J.D., et al., "Preparation and Characterization of Nickel Nanoparticles for Binding to His-Tag Proteins and Antigens," *Pharmaceutical Research*, Feb. 2007, vol. 24 (2), 10 pages.
Pavlidou M. et al., "Nanodiscs Allow Phage Display Selection for Ligands to Non-Linear Epitopes on Membrane Proteins." PLoS One, 2013. 8(9).
Portet T. et al., "A new method for measuring edge tensions and stability of lipid bilayers: effect of membrane composition." Biophysical Journal, 2010. 99(10): p. 3264-3273.
Rabinovich, A.L., et al. "On the conformational, physical properties and functions of polyunsaturated acyl chains." *Biochimica et Biophysica Acta* 1085(1), 53-62, (Aug. 1991). 10 pages.
Ralli-Jain P, et al., "Enhancement of the protective efficacy of a Chlamydia trachomatis recombinant vaccine by combining systemic and mucosal routes for immunization." Vaccine, 28, pp. 7659-7666 (2010).
Rawicz W et al., "Effect of Chain Length and Unsaturation on Elasticity of Lipid Bilayers." Biophysical Journal. 2000, 79(1): p. 328-339.
Regen, S.L., et al. "Polymerized Phophatidyl Choline Vesicles. Stabilized and Controllable Time-Release Carriers." *Biochemical and Biophysical Research Communications* 101 (1), 131-136, (Jul. 1981). 6 pages.
Restriction Reguirement for U.S. Appl. No. 15/755,018, filed Feb. 23, 2018 on behalf of Lawrence Livermore National Laboratory, dated Oct. 2, 2019. 10 Pages.
Restriction Reguirement for U.S. Appl. No. 12/469,533, dated Jun. 7, 2011, 8 pages.
Rüger R., et al., "In Vitro Characterization of Binding and Stability of Single-Chain Fv Ni-NTA-Liposomes," *Journal of Drug Targeting*, Sep. 2006, vol. 14(8), 7 pages.
Rodriguez-Maranon M.J. et al., "Prediction of the membrane-spanning Beta-strands of the major outer membrane protein of Chlamydia" Protein Science, 11, pp. 1854-1861 (2006).
Sadownik, A., et al. "Polymerized Liposomes Formed under Extremely Mild Conditions." *Journal of American Chemical Society* 108(24), 7789-7791, (Nov. 1986). 3 pages.
Saito H. et al., "Contributions of domain structure and lipid interaction to the functionality of exchangeable human apolipoproteins" Elsevier, 2004. pp. 350-380.
Schmitt L., et al., "Synthesis and Characterization of Chelator-Lipids for Reversible Immobilization of Engineered Proteins at Self-Assembled Lipid Interfaces," *Journal of the American Chemical Society*, 1994, vol. 116 (19), 7 pages.
Sells, T.D., et al. "Two-Dimensional Polymerization of Lipid Bilayers: Degree of Polymerization of Acryloyl Lipids." *Macromolecules* 27(1), 226-233, (Jan. 1994). 8 pages.

(56) References Cited

OTHER PUBLICATIONS

Serrano, J., et al. "Polymerized Surfactant Vesicles. Determinations of Rates and Degrees of Polymerization in Vesicles Prepared from Styrene-Containing Surfactants." *Macromolecules*18(10), 1999-2005, (Oct. 1985). 7 pages.

Sparks D.L. et al., "Effect of cholesterol on the charge and structure of apolipoprotein A-I in recombinant high density lipoprotein particles." Journal of Biological Chemistry, 1993. 268(31): p. 23250-7.

Su H, et al., "Immunogenicity of a chimeric peptide corresponding to T helper and B cell epitopes of the Chlamydia trachomatis major outer membrane protein" Journal of Experimental Medicine, vol. 175, pp. 227-235 (1992).

Sun G, et al., "Protection against an intranasal challenge by vaccines formulated with native and recombinant preparations of the Chlamydia trachomatis major outer membrane protein" Vaccine, 27, pp. 5020-5025 (2009).

Sun G, et al., "Structural and functional analyses of the major outer membrane protein of Chlamydia trachomatis" J Bacteriol, vol. 189, No. 17, pp. 6222-6235 (2007).

Tang G, et al., "EMAN2: an extensible image processing suite for electron microscopy" J Struct Biol, 157, pp. 38-46 (2007).

Tark S.H et al., "Nanomechanical detection of cholera toxin using microcantilevers functionalized with ganglioside nanodiscs." Nanotechnology, 2010. 21(43).

Tifrea D.F. et al., "Amphipols stabilize the Chlamydia major outer membrane protein and enhance its protective ability as a vaccine" Vaccine, 29, pp. 4623-4631 (2011).

Tifrea D.F. et al., "Increased immunoaccessibility of MOMP epitopes in a vaccine formulated with amphipols may account for the very robust protection elicited against a vaginal challenge with Chlamydia muridarum" The Journal of Immunology, 192, pp. 5201-5213 (2014).

Tsuchida, E., et al. "Polymerization of Unsaturated Phospholipids as Large Unilamellar Liposomes at Low Temperature." *Macromolecules*25(1) 207-212, (Jan. 1992). 6 pages.

Tu J, et al., "A multi-epitope vaccine based on Chlamydia trachomatis major outer membrane protein induces specific immunity in mice." Acta biochimica et biophysica Sinica, vol. 46, Issue 5, pp. 401-408 (2014).

Wang Y, et al., "Identification of surface-exposed components of MOMP of *Chlamydia trachomatis* serovar F." Protein Science, 15, pp. 122-134 (2006).

Written Opinion for International Application No. PCT/US2016/048632 filed on Aug. 25, 2016 on behalf of Lawrence Livermore National Laboratory dated Feb. 6, 2017 10 pages.

Written Opinion for International Application No. PCT/US2018/030537 filed on May 1, 2018 on behalf of Lawrence Livermore National Security dated Jan. 17, 2019 9 pages.

Xiao K, et al., "Telodendrimer-based nanocarriers for the treatment of ovarian cancer." Ther Deliv, 4(10), pp. 1279-1292 (2013) 24 pages.

Yang T. et al., "Identification and cellular localization of human PFTAIRE1" Gene, 2001. 267(2): p. 165-172.

Yang T.L et al., "Investigations of bivalent antibody binding on fluid-support phospholipid membranes: The effect of hapten density." Journal of the American Chemical Society, 2003. 125(16): p. 4779-4784.

Bayburt, T. H., et al., "Assembly of Single Bacteriorhodopsin Trimers in Bilayer Nanodiscs.", *Arch Biochem Biophys*, 450, pp. 215-222, (2006).

Bayburt, T. H., et al., "Reconstitution and Imaging of a Membrane Protein in a Nanometer-Size Phospholipid Bilayer.", *J Struct Biol.*, 123, pp. 37-44, (1998).

Camarero, J. A., et al., "Chemoselective Attachment of Biologically Active Proteins to Surfaces by Expressed Protein Ligation and its Application for "Protein Chip" Fabrication,", *J Am Chem Soc.*, vol. 126, No. 45, p. 14730-14731, (2004).

Chromy, B. A., et al., "Different Apolipoproteins Impact Nanolipoprotein Particle Formation.", *J Am Chem Soc.*, vol. 129, No. 46, p. 14348-14354, (2007).

Cruz, F., et al., "Kinetic Properties of Recombinant MAO-A on Incorporation into Phospholipid Nanodisks.", *J Neural Transm.*, 114, pp. 699-702, (2007).

Forstner, M., et al., "Carboxyl-Terminal Domain of Human Apolipoprotein E: Expression, Purification, and Crystallization.", *Protein Expr Purif.*, 17, pp. 267-272, (1999).

Frydman, J., et al., "Principles of Chaperone-Assisted Protein Folding: Differences Between in vitro and in vivo Mechanisms.", *Science*, 272, pp. 1497-1502, (1996).

Gursky, O., et al., Complex of Human Apolipoprotein C-1 with Phospholipid: Thermodynamic or Kinetic Stability? *Biochemistry*, vol. 41, No. 23, pp. 7373-7384, (2002).

Ishihara, G., et al., "Expression of G Protein Coupled Receptors in a Cell-Free Translational System Using Detergents and Thioredoxin-Fusion Vectors.", *Protein Expr Purif*, 41, pp. 27-37, (2005).

Jonas, A., "Reconstitution of High-Density Lipoproteins.", *Methods in Enzymology*, vol. 128, pp. 553-582, (1986).

Morrow, J. A., et al., "Functional Characterization of Apolipoprotein E Isoforms Overexpressed in *Escherichia coli.*", *Protein Expr Purif.*, 16, pp. 224-230, (1999).

Rao, R. S., et al., "Comparison of Multiplexed Techniques for Detection of Bacterial and Viral Proteins.", *J. Proteome Res.*, vol. 3, No. 4, pp. 736-742, (2004).

Hedderich R., "Energy-converting [NiFe] Hydrogenases From Archaea and Extremophiles: Ancestors of Complex I," *Journal of Bioenergetics and Biomembranes*,Feb. 2004, vol. 36 (1), 11 pages.

Hernandez-Caselles T., et al., "Influence of Liposome Charge and Composition on Their Interaction With Human Blood Serum Proteins," *Molecular and Cellular Biochemistry*,Mar. 1993, vol. 120 (2), 8 pages.

Hill M.A., et al., "Functional Analysis of Conserved Histidines in ADP-glucose Pyrophosphorylase From *Escherichia coli,"Biochemical and Biophysical Research Communications*,Mar. 1998, vol. 244 (2), 5 pages.

Hong Y., et al., "G-protein-coupled Receptor Microarrays for Multiplexed Compound Screening," *Journal of Biomolecular Screening*,Jun. 2006, vol. 11 (4), 4 pages.

Huleatt J.W., et al., "Potent Immunogenicity and Efficacy of a Universal Influenza Vaccine Candidate Comprising a Recombinant Fusion Protein Linking Influenza M2e to the TLR5 Ligand Flagellin," *Vaccine*, Jan. 2008, vol. 26 (2), 14 pages.

International Preliminary Report on Patentability for Application No. PCT/US2009/044722, dated Nov. 23, 2010, 7 pages.

International Preliminary Resort on Patentability for Application No. PCT/US2015/051516 filed Sep. 22, 2015 on behalf of Lawrence Livermore National Security, LLC, dated Mar. 28, 2017, 10 pages. (English Only).

International Search Report and Written Opinion for Application No. PCT/US2015/051516 filed on Sep. 22, 2015, dated Jan. 25, 2016, 12 pages.

International Search Report for Application No. PCT/US2009/044722, dated Oct. 28, 2010, 4 pages.

Jasanada F., et al., "Indium-111 Labeling of Low Density Lipoproteins With the DTPA-bis(Stearylamide): Evaluation as a Potential Radiopharmaceutical for Tumor Localization," *Bioconjugate Chemistry*, Jan.-Feb. 1996, vol. 7 (1), 10 pages.

Kapdan I.K., et al., "Bio-hydrogen Production from Waste Materials," *Enzyme and Microbial Technology*,Mar. 2006, vol. 38 (5), 14 pages.

Kolb H.C., et al., "The Growing Impact of Click Chemistry on Drug Discovery," *Drug Discovery Today*,Dec. 2003, vol. 8 (24), 10 pages.

Konishi E., et al., "Proper Maturation of the Japanese Encephalitis Virus Envelope Glycoprotein Requires Cosynthesis with the Premembrane Protein," *Journal of Virology*,Mar. 1993, vol. 67 (3), 4 pages.

Kostarelos K., et al., "Steric Stabilization of Phospholipid Vesicles by Block Copolymers Vesicle Flocculation and Osmotic Swelling Caused by Monovalent and Divalent Cations," *Journal of the Chemical Society*, Faraday Transactions,Aug. 1998, vol. 94, 10 pages.

(56) References Cited

OTHER PUBLICATIONS

Kovacs K., et al., "A Novel Approach for Biohydrogen Production," *International Journal of Hydrogen Energy*,Sep. 2006, vol. 31 (11), 9 pages.

Kubalek E.W., et al., "Two-dimensional Crystallization of Histidine-tagged, HIV-1 Reverse Transcriptase Promoted by a Novel Nickel-chelating Lipid," *Journal of Structural Biology*,Sep.-Oct. 1994, vol. 113 (2), 7 pages.

Langworthy, T.A., "Lipids of Thermoplasma," 1982, Methods in Enzymology, vol. 88, 396-406.

Lasic D.D., "Novel Applications of Liposomes," *Trends in Biotechnology*,Jul. 1998, vol. 16 (7), 15 pages.

Lazar E., et al., "Transforming Growth Factor Alpha: Mutation of Aspartic Acid 47 and Leucine 48 Results in Different Biological Activities," *Molecular and Cellular Biology*,Mar. 1988, vol. 8 (3), 6 pages.

Liang X., et al., "Mechanical Properties and Stability Measurement of Cholesterol-containing Liposome on Mica by Atomic Force Microscopy," *Journal of Colloid and Interface Science*,Oct. 2004, vol. 278 (1), 10 pages.

Lluis M.W., et al., "Protein Engineering Methods Applied to Membrane Protein Targets," *Protein Engineering, Design & Selection*,Feb. 2013, vol. 26 (2), 10 pages.

Lodish H., et al., "Section 17.5 Insertion of Membrane Proteins into the ER Membrane," *Molecular Cell Biology*, 4th edition, New York, NY.,2000, 9 pages.

Ludwig W., et al., "ARB: A Software Environment for Sequence Data," *Nucleic Acids Research*,Feb. 2004, vol. 32 (4), 9 pages.

Ma, K., et al., "Characterization of Hydrogenase II from the Hyperthermophilic Archaeon Pyrococcus furiosus and Assessment of Its Role in Sulfur Reduction," Apr. 2000, Journal of Bacteriology, vol. 182, No. 7, 1864-1871.

Manefield M., et al., "RNA Stable Isotope Probing, a Novel Means of Linking Microbial Community Function to Phylogeny," *Applied and Environmental Microbiology*,Nov. 2002, vol. 68 (11), 7 pages.

Marshall, G.R., et al., "Conformational effects of chiral a,a-dialkyl amino acids," 1988, Int. J. Peptide Protein Res., 32, 544-555.

Masquelier M., et al., "Low-density Lipoprotein as a Carrier of Antitumoral Drugs: In Vivo Fate of Drug-human Low-density Lipoprotein Complexes in Mice," *Cancer Research*,Aug. 1986, vol. 46 (8), 6 pages.

Mata-Haro V., et al., "The Vaccine Adjuvant Monophosphory Lipid A as a TRIF-Biased Agonist of TLR4," *Science*, Jun. 2007, vol. 316 (5831), 7 pages.

McGall G.H., et al., "The Efficiency of Light-Directed Synthesis of DNA Arrays on Glass Substrates," *Journal of the American Chemical Society*,Jun. 1997, vol. 119 (22), 10 pages.

Metz J., et al., "ACTH, α-MSH, and Control of Cortisol Release: Cloning, Sequencing, and Functional Expression of the Melanocortin-2 and Melanocortin-5 Receptor in Cyprinus Carpio," *American Journal of Physiology Regulatory Integrative and Comparative Physiology*,May 2005, vol. 289, 13 pages.

Moses S., et al., "Detection of DNA Hybridization on Indium Tin Oxide Surfaces," *Sensors and Actuators B*,Aug. 2007, vol. 125 (2), 7 pages.

Muscarinic Acetylcholine Receptor, Retrieved from the Internet: URL://web.archive.org/web/20071020193657//https://en.wikipedia.org/wiki/Muscarinic_acetylcholine_receptor, Wikipedia 2007, 6 pages.

Nanodisc Formation. LIAO Lab, Department of Cellbiology, Harvard Medical School, retrieved on Aug. 3, 2015, from the Internet: URL:https://liao.hms.harvard.edu/node/34, 2 pages.

Nanodisc. Kobo eBook Library, Retrieved from the Internet: URL: http://www.kobolibrary.com/articles/nanodisc, retrieved on Aug. 4, 2015, 4 pages.

Newpoint Gas "O2 Removal Services", https://www.newpointgas.com/services/oxygen-o2-removal/, 2017, 4 pages.

Non-Final Office Action for U.S. Appl. No. 14/199,973, dated May 6, 2015, 34 pages.

Non-Final Office Action for U.S. Appl. No. 14/861,750, dated Aug. 25, 2017, 23 pages.

Notice of Allowance for U.S. Appl. No. 14/199,973, dated Dec. 10, 2015, 11 pages.

Notice of Allowance for U.S. Appl. No. 14/861,750, filed Sep. 22, 2015 on behalf of Lawrence Livermore National Security, LLC, dated Jul. 24, 2018. 15 pages.

Okemoto K., et al., "A Potent Adjuvant Monophosphoryl Lipid a Triggers Various Immune Responses, but Not Secretion of IL-1beta or Activation of Caspase-1," *The Journal of Immunology*,Jan. 2006, vol. 176 (2), 6 pages.

Osada Y., et al., "Polymorphonuclear Leukocyte Activation by a Synthetic Muramyl Dipeptide Analog," *Infection and Immunity*,Dec. 1982, vol. 38 (3), 7 pages.

Ouverney C.C., et al., "Combined Microautoradiography-16S RNA Probe Technique for Determination of Radioisotope Uptake by Specific Microbial Cell Types in Situ," *Applied and Environmental Microbiology*,Apr. 1999, vol. 65 (4), 8 pages.

Parkin A., et al., "The Difference a Se Makes? Oxygen-tolerant hydrogen production by the [NiFeSe]-hydrogenase from Desulfomicrobium baculatum," Journal of the American Chemical Society, Sep. 2008, vol. 130 (40), 13410-13416. 8 pages.

Persing D.H., et al., "Taking Toll: Lipid a Mimetics as Adjuvants and Immunomodulators," *Trends in Microbiology*,Oct. 2002, vol. 10 (10 Suppl), 6 pages.

Petrakova O., et al., "Noncytopathic Replication of Venezuelan Equine Encephalitis Virus and Eastern Equine Encephalitis Virus Replicons in Mammalian Cells," *Journal of Virology*,Jun. 2005, vol. 79 (12), 12 pages.

Pettibone D.J., et al., "The Effects of Deleting the Mouse Neurotensin Receptor NTR1 on Central and Peripheral Responses to Neurotensin," *The Journal of Pharmacology and Experimental Therapeutics*,Jan. 2002, vol. 300 (1), 9 pages.

Plumere, et al., "Enzyme-catalyzed O2 removal system for electro-chemical analysis under ambient air: application in an amperometric nitrate biosensor (Abstract only)", Anal Chem. Mar. 6, 2012;84(5):2141-2146, Epub Feb. 10, 2012. 2 pages.

Protocols for Preparation of Nanodiscs, Mar. 2008, 7 pages.

Radajewski S., et al., "Identification of Active Methylotroph Populations in an Acidic Forest Soil by Stable Isotope Probing," Microbiology, Aug. 2002, vol. 148 (Pt 8), 12 pages.

Radajewski S., et al., "Stable-Isotope Probing as a Tool in Microbial Ecology," *Nature*, Feb. 2000, vol. 403 (6770), 4 pages.

Ratanabanangkoon P., et al., "Two-Dimensional Streptavidin Crystals on Giant Lipid Bilayer Vesicles," *Langmuir*,2002, vol. 18 (11), 7 pages.

Ren X.R., et al., "Different G Protein-Coupled Receptor Kinases Govern G Protein and Beta-Arrestin-Mediated Signaling of V2 Vasopressin Receptor," *Proceedings of the National Academy of Sciences of the United States of America*,Feb. 1, 2005, vol. 102(5), 6 pages.

Rensen P.C., et al., "Recombinant Lipoproteins: Lipoprotein-like Lipid Particles for Drug Targeting," *Advanced Drug Delivery Reviews*,Apr. 25, 2001, vol. 47(2-3), 26 pages.

Restriction Requirement for U.S. Appl. No. 14/199,973, dated Dec. 8, 2014, 7 pages.

Restriction Requirement for U.S. Appl. No. 14/861,750, dated May 19, 2017, 7 pages.

Rüger R., et al., "Generation of Immunoliposomes using Recombinant Single-Chain Fv Fragments Bound to Ni-NTA-Liposomes," *Journal of Drug Targeting*, Aug. 2005, vol. 13(7), 8 pages.

Schena M., et al., "Quantitative Monitoring of Gene Expression Patterns With a Complementary DNA Microarray," *Science*,Oct. 1995, vol. 270 (5235), 4 pages.

Schnell D.J. et al., "Protein Translocons: Multifunctional Mediators of Protein Translocation across Membranes," *Cell*,Feb. 21, 2003, vol. 112(4), 15 pages.

Simon S.R., et al., "Chemical Modification of Hemoglobins: A Study of Conformation Restraint by Internal Bridging," *Proceedings of the National Academy of Sciences of the United States of America*,Aug. 1966, vol. 56 (2), 8 pages.

Aina O.H., et al., "From combinatorial chemistry to cancer-targeting peptides" Mol Pharm, vol. 4, No. 5, pp. 631-651 (2007).

(56) References Cited

OTHER PUBLICATIONS

Akkaladevi, N., et al., "Assembly of anthrax toxin pore: Lethal-factor complexes into lipid nanodiscs." *Protein Science*,2013. 22(4): p. 492-501.

Allen, T.M. et al., "Drug delivery systems: entering the mainstream." *Science*,2004. 303(5665): p. 1818-22.

Anantharamaiah, G.M., et al., "Studies of Synthetic Peptide Analogs of the Amphipathic Helix / Structures of Complexes with Dimyristoyl Phosphatidycholine ," 1985, The Journal of Biological Chemistry, vol. 260, No. 18, 10248-10255.

Bayburt T.H., et al., "Membrane Protein Assembly into Nanodiscs," *FEBS Letters*, May 2010, vol. 584 (9), 7 pages.

Baylon, J.L., et al., "Characterizing the membrane-bound state of cytochrome P450 3A4: structure, depth of insertion, and orientation." *Journal of the American Chemical Society*,2013. 135(23):p. 8542-8551.

Bhattacharya, P., et al., "Nanodisc-Incorporated Hemagglutinin Provides Protective Immunity against Influenza Virus Infection." *Journal of Virology*,2010. 84(1): p. 361-371.

Blanchette C.D., et al., "Kinetic analysis of his-tagged protein binding to nickel-chelating nanolipoprotein particles." Bioconjug Chem, 21, pp. 1321-1330 (Jul. 2010).

Bolikal, D. et al., "Degree of Polymerization of a Vesicle Membrane." *Macromolecules*,1984. 17(6): p. 1287-1289.

Cappuccio, J.A., et al., "Cell-free expression for nanolipoprotein particles: building a high-throughput membrane protein solubility platform, in *Methods in Molecular Biology: High Throughput Protein Expression and Purification*." 2009, vol. 498, *Springer*, p. 273-295.

Chen et al., "Fluorescence Study of Inclusion Complexes between Star-Shaped Cholic Acid Derivatives and Polycyclic Aromatic Fluorescent Probes and the Size Effects of Host and Guest Molecules" Journal of Physical Chemistry B, vol. 112, No. 11, p. 3402-3409 (2008).

Cho, K., et al., "Therapeutic nanoparticles for drug delivery in cancer." *Clinical cancer research*,2008. 14(5): p. 1310-1316.

Chung, B.H., et al., "Studies of Synthetic Peptide Analogs of the Amphipathic Helix / Correlation of Structure with Function," 1985, The Journal of Biological Chemistry, vol. 260, No. 18, 10256-10262.

Corrected Notice of Allowance for U.S. Appl. No. 13/719,785, filed Dec. 19, 2012 on behalf of Lawrence Livermore National Laboratory dated May 23, 2016 5 pages.

Cuenca, AG et al., "Emerging implications of nanotechnology on cancer diagnostics and therapeutics." *Cancer*,2006. 107: pp. 459-466. pp. 8.

Dalkara et al., "Intracytoplasmic Delivery of Anionic Proteins" Molecular Therapy, Jun. 2004, vol. 9, No. 6, pp. 964-969.

Dawson P.E., et al., "Synthesis of Native Proteins by Chemical Ligation," *Annual Review of Biochemistry*,2000, vol. 69, 923-960. 39 pages.

Ding, Y., et al., "A biomimetic nanovector-mediated targeted cholesterol-conjugated siRNA delivery for tumor gene therapy." *Biomaterials*,2012. 33(34): p. 8893-8905.

Duncan R., "Dawning Era of Polymer Therapeutics" Nature Review Drug Discovery vol. 2, No. 5 p. 347-360 (2003).

Final Office Action for U.S. Appl. No. 15/499,855, filed Apr. 27, 2017 on behalf of Lawrence Livermore National Laboratory dated Aug. 8, 2019 11 pages.

Ghosh M, et al., "Cationic lipid Nanodisks as an siRNA delivery vehicle" Biochem Cell Biol (2014), 92(3): 200-205. 14 pages.

Gref et al., "Biodegradable Long-Circulating Polymeric Nanospheres" Science American Association for the Advancement of Science vol. 263 No. 5153, p. 1600-1603 (1994).

Imura, T., et al., "Minimum Amino Acid Residues of an a-Helical Peptide Leading to Lipid Nanodisc Formation," 2014, J. Oleo Sci. 63, (11) 1203-1208.

Imura, T., et al., "Surfactant-like Properties of an Amphilic a-Helical Peptide Leading to Lipid Nanodisc Formation," 2014, Langmuir, 30, 4752-4759.

"Individual" from Merriam-Webster, Jan. 13, 2015, accessed via WayBackMachine.com (2 pages).

International Preliminary Reporton Patentability for Application No. PCT/US2015/051172 filed Sep. 9, 2016 on behalf of Lawrence Livermore National Security, LLC, dated Mar. 13, 2018. 8 pages. (English Only).

International Search Report and Written Opinion for PCT/US2009/057852, 19 pages, dated May 6, 2010.

International Search Report and Written Opinion for PCT/US2012/070508, 9 pages, dated Feb. 27, 2013.

International Search Report for International Application No. PCT/US2018/030648 filed on May 2, 2018 on behalf of Synthetic Genomics dated Aug. 30, 2018 4 pages.

Jones M.K., et al., "Computer Programs to Identify and Classify Amphipathic alpha Helical Domains," *Journal of Lipid Research*, Feb. 1992, vol. 33 (2), 287-296. 10 pages.

Justesen, B.H., et al., "Isolation of monodisperse nanodisc-reconstituted membrane proteins using free flow electrophoresis." *Analytical chemistry*,2013. 85(7): p. 3497-3500.

Keppetipola S, et al., From gene to HSQC in under five hours: high-throughput NMR proteomics: J Am Chem Soc, 128, pp. 4508-4509 (Apr. 2006).

Kigawa T, et al., "Cell-free production and stable-isotope labeling of milligram quantities of proteins" FEBS Lett, 442, pp. 15-19 (Jan. 1999).

Klussman S, et al., "The Aptamer Handbook: Functional Oligonucleotides and Their Applications" *Wiley-VCH* (2006) 509 pages.

Lam K, et al., "A new type of synthetic peptide library for identifying ligand-binding activity" Nature, vol. 354, pp. 82-84 (1991).

Lam K.S., et al., "Application of Combinatorial Library Methods in Cancer Research and Drug Discovery," *Anti-cancer Drug Design*, Apr. 1997, vol. 12 (3), 145-167. 24 pages.

Levy-Nissenbaum E. et al., "Nanotechnology and aptamers: applications in drug delivery" *Trends in Biotechnology* 26(8):442-449 (2008).

Li et al., "Antimicrobial Activities of Amine- and Guanidine-Functionalized Cholic Acid Derivatives" Antimicrobial Agents and Chemotherapy vol. 43 (6) p. 1347-1349 (Jun. 1999).

Luo et al., "Asymmetric Poly(ethylene glycol) Star Polymers with a Cholic Acid Core and Their Aggregation Properties" Biomacromolecules vol. 10 No. 4 p. 900-906 (2009).

Luo J, et al., "Well-defined, size-tunable, multifunctional micelles for efficient paclitaxel delivery for cancer treatment." Bioconjug Chem, 21, pp. 1216-1224 (Jul. 2010).

Madani SY, et al., "A concise review of carbon nanotube's toxicology." Nano Rev., 2013. vol. 4, Issue 1.

"Microsome" from Wikipedia, Mar. 3, 2008, accessed via WayBackMachine.com (1 page).

Midtgaard, S.R., et al., "Self-assembling peptides form nanodiscs that stabilize membrane proteins," 2014, Soft Matter, 10, 738-752.

Miyazaki, M., et al., "Effect of phospholipid composition on discoidal HDL formation." *Biochimica et Biophysica Acta (BBA)-Biomembranes*,2013. 1828(5): p. 1340-1346.

Mori M, et al., "Cell-free synthesis and processing of a putative precursor for mitochondrial carbamyl phosphate synthetase I of rat liver" Proc Natl Acad Sci USA, vol. 76, No. 10, pp. 5071-5075 (Oct. 1979).

Nanodisc Trademark #78166119, Owner: Sligar, Stephen G., Retrieved from the Internet:[URL:https://inventively.com/search/trademarks/78166119], retrieved on Aug. 4, 2015, 2 pages.

Non-Final Office Action for U.S. Appl. No. 13/719,785, filed Dec. 19, 2012 on behalf of Lawrence Livermore National Laboratory dated Jun. 4, 2015 8 pages.

Non-Final Office Action for U.S. Appl. No. 15/499,855, filed Apr. 27, 2017, on behalf of Lawrence Livermore National Security LLC, dated Jan. 11, 2019. 7 pages.

Notice of Allowance for U.S. Appl. No. 13/719,785, filed Dec. 19, 2012 on behalf of Lawrence Livermore National Laboratory dated Feb. 17, 2016 7 pages.

(56) References Cited

OTHER PUBLICATIONS

Rensen PC, et al., "Human recombinant apolipoprotein E-enriched liposomes can mimic low-density lipoproteins as carriers for the site-specific delivery of antitumor agents." Mol Pharmacol, 52, pp. 445-455 (Sep. 1997).

Ryan RO, "Nanobiotechnology applications of reconstituted high density lipoprotein" J Nanobiotechnology, 8:28 (Dec. 2010) 10 pages.

Ryan RO, "Nanodisks: hydrophobic drug delivery vehicles" Expert Opin Drug Deliv., 5(3), pp. 343-351 (Mar. 2008).

Segota S., et al., "Spontaneous Formation of Vesicles," *Advances in Colloid and Interface Science*,Sep. 2006, vol. 121, pp. 51-75, 25 pages.

Semple et al., "Rational design of cationic lipids for siRNA delivery" Nature Biotechnology Feb. 2010, vol. 28, No. 2, pp. 172-176 + 2 additional pages.

Sligar, S., "Overview of Nanodisc Technology" from Sligar Lab, accessed Nov. 21, 2014(1 page).

Sligar webpage http://sligarlab.life.uiuc.edu/nanodisc.html, accessed Feb. 28, 2018. "Nanodisc Technology: Soluble Lipid Bilayer Systems for Structural and Functional Studies of Membrane Proteins" (3 pages).

Sparreboom, A., et al., "Comparative preclinical and clinical pharmacokinetics of a cremophor-free, nanoparticle albumin-bound paclitaxel (ABI-007) and paclitaxel formulated in Cremophor (Taxol)." *Clin Cancer Res*,2005. 11(11): p. 4136-43.

Sperling R.A., et al., "Surface Modification, Functionalization and Bioconjugation of Colloidal Inorganic Nanoparticles," Philosophical Transactions of the Royal Society A, Mar. 2010, vol. 368, 1333-1383, 51 pages.

Sunahara H, et al., "Design and synthesis of a library of BODIPY-based environmental polarity sensors utilizing photoinduced electron-transfer-controlled fluorescence ON/OFF switching" J Am Chem Soc., 129, pp. 5597-5604 (May 2007).

Svetina S., et al., "Shape Behavior of Lipid Vesicles as the Basis of Some Cellular Processes," *The Anatomical Record*, Nov. 2002, vol. 268 (3), 215-225. 11 pages.

Tieke, B. et al., "Polymerization of diacetylenes in multilayers." *Journal of Polymer Science: Polymer Chemistry Edition*,1979. 17(6): p. 1631-1644.

Tufteland, M. et al., "Nanodisks derived from amphotericin B lipid complex." *Journal of Pharmaceutical Sciences*,2008. 97(10): p. 4425-4432. 14 pages.

"Vesicle" from Wikipedia, Dec. 16, 2008, accessed via WayBackMachine.com (5 pages).

Vickers, K.C., et al., "MicroRNAs are transported in plasma and delivered to recipient cells by high-density lipoproteins." *Nat Cell Biol*,2011. 13(4): p. 423-33. 20 pages.

Vijayalakshmi et al., "A Simple Construction of a Bile Acid Based Dendritic Light Harvesting System" Organic Letters vol. 7 No. 13 p. 2727-2730 (2005).

Wadsater, M., et al., "Monitoring shifts in the conformation equilibrium of the membrane protein cytochrome P450 reductase (POR) in nanodiscs." *Journal of Biological Chemistry*,2012. 287(41): p. 34596-34603.

Wang, J., et al., "Tumor targeting effects of a novel modified paclitaxel-loaded discoidal mimic high-density lipoproteins." *Drug delivery*,2013. 20(8): p. 356-363.

Wang, S. et al., "The unsolved mystery of apoA-1 recycling in adipocyte." *Lipids Health Dis*,2016. 15: p. 35, 8 pages.

Weilhammer, D.R., et al., "The use of nanolipoprotein particles to enhance the immunostimulatory properties of innate immune agonists against lethal influenza challenge." *Biomaterials*,2013. 34(38): p. 10305-18.

Whorton M.R., et al., "A Monomeric G Protein-Coupled Receptor Isolated in a High-Density Lipoprotein Particle Efficiently Activates its G Protein," Proceedings of the National Academy of Sciences, May 2007, vol. 104 (18), 7682-7687. 6 pages.

Written Opinion for International Application No. PCT/US2018/030648 filed on May 2, 2018 on behalf of Synthetic Genomics dated Aug. 30, 2018 6 pages.

Xiao et al., "PEG oligocholic acid Telodendrimer micelles for the targeted delivery of doxorubicin to B cell lymphoma" Journal of Controlled Release vol. 155 p. 272-281 (2011).

Xiao K, et al., "A self-assembling nanoparticle for paclitaxel delivery in ovarian cancer." Biomaterials, 30 (30), pp. 6006-6016 (2009) 24 pages.

Yang JP, et al., "Cell-free synthesis of a functional G protein-coupled receptor complexed with nanometer scale bilayer discs." BMC Biotechnol, 11:57, (May 2011) 8 pages.

Yavlovich, A., et al., "A novel class of photo-triggerable liposomes containing DPPC:DC8,9PC as vehicles for delivery of doxorubcin to cells." *Biochimica Biophysica Acta-Biomembranes*,2011. 1808(1): p. 117-126. 22 pages.

Yuan, Y., et al., "Delivery of hydrophilic drug doxorubicin hydrochloride-targeted liver using apoAI as carrier." *J Drug Target*,2013. 21(4): p. 367-374.

Zidovska A. et al., "Block Liposome and Nanotube Formation is a General Phenomenon of Two-Component Membranes Containing Multivalent Lipids", Jan. 1, 2011, Soft Matter, vol. 7, No. 18, pp. 8363-8369.

Zuris J, et al., "Cationic lipid-mediated delivery of proteins enables efficient protein-based genome editing in vitro and in vivo" Nature Biotechnology, vol. 33, No. 1, p. 73-80 (2015) 8 pages.

Baas, B.J., et al., "Homotropic Cooperativity of Monomeric Cytochrome P450 3A4 in a Nanoscale Native Bilayer Environment.", *Arch Biochem Biophys* 430, pp. 218-228, (2004).

Bayburt, T.H., et al., "Self-Assembly of Single Integral Membrane Proteins into Soluble Nanoscale Phospholipid Bilayers.", *Protein Science*, vol. 12, pp. 2476-2481, (2003).

Bayburt, T.H., et al., "Single-Molecule Height Measurements on Microsomal Cytochrome P450 in Nanometer-Scale Phospholipid Bilayer Disks.", *Proc Natl Acad Sci U S A*, vol. 99, No. 10, pp. 6725-6730, (2002).

Bayburt, T.H., et al., "Transducin Activation by Nanoscale Lipid Bilayers Containing One and Two Rhodopsins.", *J Biol Chem*, vol. 282, No. 20, p. 14875-14881, (2007), 8 pages.

Boldog, T., et al., "Nanodiscs Separate Chemoreceptor Oligomeric States and Reveal their Signaling Properties.", *Proc Natl Acad Sci U S A*, vol. 103, No. 31, p. 11509-11514, (2006).

Civjan, N.R., et al., "Direct Solubilization of Heterologously Expressed Membrane Proteins by Incorporation into Nanoscale Lipid Bilayers.", *Biotechniques*, vol. 35, No. 3, pp. 556-560, (2003), 6 pages.

Jayaraman, S., et al., "Structural Basis for Thermal Stability of Human Low-Density Lipoprotein.", *Biochemistry*, vol. 44, pp. 3965-3971, (2005).

Jonas, A., et al., "Defined Apolipoprotein A-I Conformations in Reconstituted High Density Lipoprotein Discs.", *J Biol Chem*, vol. 264, No. 9, pp. 4818-4824, (1989).

Klammt, C., et al., "Evaluation of Detergents for the Soluble Expression of Alpha-Helical and Beta-Barrel-Type Integral Membrane Proteins by a Preparative Scale Individual Cell-Free Expression System.", *Febs Journal*, vol. 272, pp. 6024-6038, (2005).

Klammt, C., et al., "High Level Cell-Free Expression and Specific Labeling of Integral Membrane Proteins.", *Eur. J. Biochem.*, vol. 271, pp. 568-580, (2004), 14 pages.

Klammt, C., et al., "Cell-Free Production of G Protein-Coupled Receptors for Functional and Structural Studies.", *J Struct Biol.*, 12 pages, (2007).

Leitz, A., et al., "Functional Reconstitution of Beta2-Adrenergic Receptors Utilizing Self-Assembling Nanodisc Technology.", *Biotechniques*, vol. 40, No. 5, pp. 601, 602, 604, 606, 608, 610, (2006).

Nath, A., et al., "Applications of Phospholipid Bilayer Nanodiscs in the Study of Membranes and Membrane Proteins.", *Biochemistry*, vol. 46, No. 8, pp. 2059-2069, (2007).

Peters-Libeu, C., et al., "Model of Biologically Active Apolipoprotein E Bound to Dipalmitoylphosphatidylcholine.", *J Biol Chem*, vol. 281, No. 2, pp. 1073-1079, (2006), 8 pages.

(56) References Cited

OTHER PUBLICATIONS

Sawasaki, T., et al., "A Bilayer Cell-Free Protein Synthesis System for High-Throughput Screening of Gene Products.", *FEBS Letters* 514, pp. 102-105, (2002).
Shaw, A.W., et al., "Phospholipid Phase Transitions in Homogenous Nanometer Scale Bilayer Discs.", *FEBS Letters* 556, pp. 260-264, (2004).
Tufteland, M., et al., "Peptide Stabilized Amphotericin B Nanodisks.", Peptides, vol. 28(4), pp. 741-746, (2007), 13 pages.
Wallin, E., et al., "Genome-Wide Analysis of Integral Membrane Proteins from Eubacterial, Archaean, and Eukaryotic Organisms.", Protein Science, vol. 7, pp. 1029-1038, (1998).
International Search Report for International Application No. PCT/US2016/051172 filed on Sep. 9, 2016 in the name of Lawrence Livermore National Security, LLC, dated Dec. 13, 2016. 6 pages.
Written Opinion for International Application No. PCT/US2016/051172 filed on Sep. 9, 2016 in the name of Lawrence Livermore National Security, LLC, dated Dec. 13, 2016. 7 pages.
Singh-Gasson S., et al., "Maskless Fabrication of Light-directed Oligonucleotide Microarrays Using a Digital Micromirror Array," *Nature Biotechnology*,Oct. 1999, vol. 17 (10), 5 pages.
Soboh B., et al., "A Multisubunit Membrane-Bound [NiFe] Hydrogenase and an NADH-Dependent Fe-only Hydrogenase in the Fermenting Bacterium Thermoanaerobacter tengcongenis," *Microbiology*,2004, vol. 150, 13 pages.
Sun X.L., et al., "Membrane-Mimetic Films of Asymmetric Phosphtidylcholine Lipid Bolaamphiphiles," *Langmuir*,Jan. 2006, vol. 22 (3), 8 pages.
Tercier-Waeber, et al., "Submersible Online Oxygen Removal System Coupled to an in Situ Voltammetric Probe for Trace Element Monitoring in Freshwater (Abstract only)", Environ. Sci. Technol., 2000, 34 (18), pp. 4018-4024, Publication Date (Web): Aug. 11, 2000. 4 pages.
Terpe K., et al., "Overview of Tag Protein Fusions: From Molecular and Biochemical Fundamentals to Commercial Systems," *Applied Microbiology and Biotechnology*,Jan. 2003, vol. 60 (5), 11 pages.
Ueda H., et al., "Induction of Tumor Necrosis Factor-Alpha in Solid Tumor Region by the Orally Administered Synthetic Muramyl Dipeptide Analogue, Romurtide," *International Immunopharmacology*, Jan. 2001, vol. 1 (1), 8 pages.
Uhlik O., et al., "DNA-Based Stable isotope Probing: A Link between Community Structure and Function," *Science of the Total Environment*,Jun. 2009, vol. 407 (12), 9 pages.
Ulmer J,B., et al., "Vaccine Manufacturing: Challenges and Solutions," *Nature Biotechnology*,Nov. 2006, vol. 24 (11), 7 pages.
Unger R., et al., "The Genetic Algorithm Approach to Protein Structure Prediction," *Structure and Bonding*,Feb. 2004, vol. 110, 24 pages.
VICI (Valco Instruments Co. Inc.) "Oxygen Removal System", https://www.vici.com/instr/deox.php, pp. 1-2, 2 pages, 2018.
Vignais P.M., et al., "Occurrence, Classification, and Biological Function of Hydrogenases: An Overview," *Chemical Reviews*,Oct. 2007, vol. 107 (10), 67 pages.
Vuorilehto K., et al., "Indirect Electrochemical Reduction of Nicotinamide Coenzymes," *Bioelectrochemistry*, Dec. 2004, vol. 65 (1), 7 pages.
Wacey A.I., et al., "Disentangling the Perturbational Effects of Amino Acid Substitutions in the DNA-binding Domain of p53," *Human Genetics*, Jan. 1999, vol. 10 4 (1), 8 pages.
Weeratna R.D., et al., "CpG DNA Induces Stronger Immune Responses with Less Toxicity than Other Adjuvants," *Vaccine*,Mar. 2000, vol. 18 (17), 8 pages.
White S.H., et al., "How Translocons Select Transmembrane Helices," Annual Review of Biophysics, 2008, vol. 37, 23-42. 20 pages.
Widman D.G., et al., "Construction and Characterization of a Second-Generation Pseudoinfectious West Nile Virus Vaccine Propagated Using a New Cultivation System," *Vaccine*,May 2008, vol. 26 (22), 10 pages.

Wikipedia, "5-HT Receptor," Wikipedia 2007, Retrieved from the Internet:[URL: http://web.archive.org/web/20071109235348/http://en.wikipedia.org/wiki/5-HT_receptor], 4 pages.
Wikipedia, Adrenergic Receptor, https://web.archive.org/web/20061230132111http//en.wikipedia.org/wiki/Adrenergic_Receptor, 2006, 4 pages.
Written Opinion for Application No. PCT/US2009/044722, dated Oct. 28, 2010., 8 pages.
Yoon J.C., et al., "Three-Dimensional Graphene Nano-Networks with High Quality and Mass Production Capability via Precursor-Assisted Chemical Vapor Deposition," *Scientific Reports*,2013, vol. 1788, 8 pages.
Zhou, H., et al., Noncovalent Attachment of NAD+ Cofactor onto Carbon Nanotubes for Preparation of Integrated Dehydrogenase-Based Electrochemical Biosensors,: 2010, Langmuir Article, 26(8) 6028-6032.
Zimmermann S, et al., "Immunostimulatory DNA as Adjuvant: Efficacy of Phosphodiester CPG Oligonucleotides is Enhanced by 3' Seguence Modifications," *Vaccine*,Feb. 2003, vol. 21 (9-10), 6 pages.
Adamczyk J., et al., "The Isotope Array, a New Tool That Employs Substrate-Mediated Labeling of rRNA for Determination of Microbial Community Structure and Function," *Applied and environmental microbiology*, Nov. 2003, vol. 69 (11), 13 pages.
Adams, M.W.W., et al., "Hydrogenase," 1981, Biochimica et Biophysica Acta 594, 105-176.
Addison S.L., et al., "Stable Isotope Probing: Technical Considerations When Resolving (15)N-labeled RNA in Gradients," *Journal of Microbiological Methods*, Jan. 2010, vol. 80(1), 6 pages.
Bayburt T.H., et al., "Self-Assembly of Discoidal Phospholipid Bilayer Nanoparticles with Membrane Scaffold Proteins," Nano Letters, 2002, vol. 2 (8), 4 pages.
Blanchette C.D., et al., "Atomic Force Microscopy Differentiates Discrete Size Distributions Between Membrane Protein Containing and Empty Nanolipoprotein Particles," Biochimica et Biophysica Acta, 2009, vol. 1788 (3), 724-731. 8 pages.
Boldog T., et al., "Using Nanodiscs to Create Water-soluble Transmembrane Chemoreceptors Inserted in Lipid Bilayer," *Methods in Enzymology*,2007, vol. 423, 317-335. 19 pages.
Burgdorf T., et al., "The Soluble NAD+-Reducing [NiFe]-Hydrogenase from Ralstonia eutropha H16 Consists of Six Subunits and can be Specifically Activated by NADPH," Journal of Bacteriology, May 2005, vol. 187 (9), 3122-3132. 11 pages.
Cappucchio J., et al., "Cell-free Co-expression of Functional Membrane Proteins and Apolipoprotein, Forming Soluble Nanolipoprotein Particles," Molecular and Cellular Proteomics, Nov. 2008, vol. 7 (11), 8 pages.
Casey P.J., et al., "Protein Prenyltransferases," *Journal of Biological Chemistry*, Mar. 1996, vol. 271 (10), 5289-5292. 5 pages.
Chefson A., et al., "Progress Towards the Easier Use of P450 Enzymes," *Molecular Biosystems*, Oct. 2006, vol. 2 (10), 462-469. 8 pages.
Choquet C.G., et al., "Stability of Pressure-extruded Liposomes Made From Archaeobacterial Ether Lipids," *Applied Microbiology and Biotechnology*, Nov. 1994, vol. 42 (2-3), 10 pages.
Cornish K., et al., "Characterization of Cis-Prenyl Transferase Activity Localised in a Buoyant Fraction of Rubber Particles From Ficus Elastica Latex," *Plant Physiology and Biochemistry*, May/Jun. 1996, vol. 34 (3), 377-384. 10 pages.
Cornish K., et al., "Natural Rubber biosynthesis in Plants: Rubber Transferase," Methods in Enzymology, 2012, vol. 515, 63-82. 20 pages.
Cornish K., et al., "Rubber Biosynthesis in Plants," American Oil Chemist Society, *The Lipid Library*, Nov. 2011, 10 pages.
Das D., et al., "Role of Fe-hydrogenase in Biological Hydrogen Production," Current Science, Jun. 2006, vol. 90 (12), 1627-1637. 11 pages.
Denisov, I.G., et al., "Cytochromes P450 in Nanodiscs," Biochimica et Biophysica Act, 2010, 7 pages.
Donninger C., et al., "An Improved Synthesis of Isopentenyl Pyrophosphate," The Biochemical Journal, Nov. 1967, vol. 105 (2), 545-547. 3 pages.

(56) References Cited

OTHER PUBLICATIONS

Dubey R., et al., "Microencapsulation Technology and Applications," Defence Science Journal, Jan. 2009, vol. 59 (1), 82-95. 14 pages.
Elgren T. E. et al., "Immobilization of Active Hydrogenases by Encapsulation in Polymeric Porous Gels," *Nano Letters*, Oct. 2005, vol. 5 (10), 2085-2087. 3 pages.
Final Office Action for U.S. Appl. No. 12/352,472, dated Jun. 7, 2012, 25 pages.
Final Office Action for U.S. Appl. No. 12/352,472, dated Jun. 29, 2015, 18 pages.
Final Office Action for U.S. Appl. No. 12/604,362, dated Dec. 4, 2012, 8 pages.
Friedrich T. et al., "The respiratory complex I of bacteria, archaea and eukarya and its module common with membrane-bound multisubunit hydrogenases." FEBS Lett. Aug. 2000 11;479(1-2):1-5.
Gan L., et al., "Role of NADPH-Cytochrome P450 Reductase and Cytochrome-b-5/NADH-b5 Reductase in Variability of CYP3A Activity in Human Liver Microsomes," *Drug Metabolism and Disposition*, Jan. 2009, vol. 37 (1), 90-96. 7 pages.
Gilbert L., "Insect Development: Morphognesis, molting and Metamorphosis," *Academic Press*, Sep. 18, 2009, 573-574. 2 pages.
Gorrod J.W., et al., "Some Observations on Type I and Type II Microsomal Binding Spectra," *Xenobiotica*, Jul.-Oct. 1971, vol. 1 (4), 521-522. 2 pages.
Greve, H-H., "Rubber, 2. Natural" in *Ullmann's Encyclopedia of Industrial Chemistry* vol. 31 (2012) 583-596. Wiley-VCH Verlag GmbH & Co. KGaA, Weinheim, 14 pages.
Grinkova, Y.V., et al., "Engineering extended membrane scaffold proteins for self-assembly of soluble nanoscale lipid bilayers," Protein Engineering, Design and Selection, 2010, vol. 23, No. 11, pp. 843-848.
Gronover C.S., et al., "Natural Rubber Biosynthesis and Physics-Chemical Studies on Plant Derived Latex," *Biotechnology of Biopolymers*, Jul. 2011, 75-88.15 pages.
Hallenbeck P.C. et al., "Biological Hydrogen Production: Fundamentals and Limiting Processes," *International Journal of Hydrogen Energy*, Nov. 2002, vol. 27 (11-12), 1185-1193. 9 pages.
Hasemann C.A., et al., "Structure and Function of Cytochromes P450: a Comparative Analysis of Three Crystal Structures," *Structure*, Jan. 1995, vol. 3 (1), 22 pages.
Hauger R.L., et al., "Corticotropin Releasing Factor (CRF) Receptor Signaling in the Central Nervous System: New Molecular Targets," *CNS & Neurological Disorders Drug Targets*, Aug. 2006, vol. 5 (4), 49 pages.
Hein C.D., et al., "Click Chemistry, A Powerful Tool for Pharmaceutical Sciences," *Pharmaceutical Research*, Oct. 2008, vol. 25 (10), 30 pages.
Hiraishi T., et al., "Enzyme-catalyzed Synthesis and Degradation of Biopolymers," *Mini-Reviews in Organic Chemistry, Bentham Science Publishers*, Feb. 2009, vol. 6 (1), 11 pages.
Ho D., et al., "Fabrication of Biomolecule-copolymer Hybrid Nanovesicles as Energy Conversion Systems," *Nanotechnology*, Nov. 2005, vol. 16 (12), 13 pages.
Katzen F., et al., "Insertion of Membrane Proteins Into Discoidal Membranes Using a Cell-free Protein Expression Approach," Journal of Proteome Research, Aug. 2008, vol. 7 (8), 8 pages.
Kurkin S., et al., "The Membrane-bound [NiFe]-hydrogenase (Ech) From Methanosarcina Barker!: Unusual Properties of the Iron-sulphur Clusters," *European Journal of Biochemistry*, Dec. 2002, vol. 269 (24), 6101-6111. 11 pages.
Lechene C., et al., "High-resolution Quantitative Imaging of Mammalian and Bacterial Cells Using Stable Isotope Mass Spectrometry," *Journal of Biology*, 2006, vol. 5 (6), article 20, 30 pages.
Long M., et al., "Characterization of a HoxEFUYH type of [NiFe] Hydrogenase from Allochromatium Vinosum and Some EPR and IR Properties of the Hydrogenase Module," *Journal of Biological Inorganic Chemistry*, Jan. 2007, vol. 12 (1), 18 pages.

McIntosh C.L., et al., "The [NIFe]-Hydrogenase of the *Cyanobacterium synechocystis* sp. PCC 6803 Works Bidirectionally with a Bias to H2 Production," *Journal of the American Chemical Society*, Jun. 2011, vol. 133 (29), 12 pages.
McTernan P.M., et al., "Intact Functional Fourteen-Subunit Respiratory Membrane-Bound [NiFe]-Hydrogenase Complex of the Hyperthermophilic Archaeon Pyrococcus Furiosus," *Journal of Biological Chemistry*, Jul. 2014, vol. 289 (28), 10 pages.
Meuer J., et al., "Purification and Catalytic Properties of Ech Hydrogenase From Methanosarcina Barkeri," *European Journal of Biochemistry*, Oct. 1999, vol. 265 (1), 11 pages.
Meyer J., "[Fe/Fe] Hydrogenases and Their Evolution: A Genomic Perspective," *Cellular and Molecular Life Sciences*, May 2007, vol. 64 (9), 1063-1084. 22 pages.
Non-Final Office Action for U.S. Appl. No. 12/352,472, dated Aug. 12, 2016, 31 pages.
Non-Final Office Action for U.S. Appl. No. 12/352,472, dated Dec. 26, 2014, 24 pages.
Non-Final Office Action for U.S. Appl. No. 12/352,472, dated Oct. 2, 2013, 19 pages.
Non-Final Office Action for U.S. Appl. No. 12/352,472, dated Sep. 22, 2011, 21 pages.
Non-Final Office Action for U.S. Appl. No. 12/352,548, dated Sep. 13, 2011, 19 pages.
Non-Final Office Action for U.S. Appl. No. 12/604,362, dated May 7, 2012, 12 pages.
Non-Final Office Action for U.S. Appl. No. 14/536,513, dated Mar. 24, 2016, 19 pages.
Notice of Allowance for U.S. Appl. No. 12/352,472, dated Mar. 17, 2017, 12 pages.
Notice of Allowance for U.S. Appl. No. 12/352,548, dated Apr. 25, 2014, 9 pages.
Notice of Allowance for U.S. Appl. No. 12/352,548, dated Aug. 5, 2014, 8 pages.
Notice of Allowance for U.S. Appl. No. 12/352,548, dated Mar. 12, 2012, 10 pages.
Notice of Allowance for U.S. Appl. No. 12/604,362, dated Jul. 30, 2014, 13 pages.
Notice of Allowance for U.S. Appl. No. 14/536,513, dated Jul. 14, 2016, 5 pages.
Ohya N., et al., "Biosynthesis of Natural Rubber and Other Natural Polyisoprenoids," Biopolymers Polyisoprenoids, Jan. 2005, 73-81. 9 pages.
Pan Z., et al., "The Major Protein of Guayule Rubber Particles is a Cytochrome P450: Characterization based on cDNA Cloning and Spectroscopic Analysis of the Solubilized Enzyme and Its Reaction Products," The Journal of Biological Chemistry, Apr. 1995, vol. 270 (15), 8487-8494. 8 pages.
Paterson-Jones J.C., et al., "The Biosynthesis of Natural Rubber," Journal of Plant Physiology, Jun. 1990, vol. 136 (3), 7 pages.
Persson B., et al., "Topology Prediction of Membrane Proteins," Protein Science, Feb. 1996, vol. 5 (2), 9 pages.
Ponciano G., et al., "Transcriptome and Gene Expression Analysis in Cold-Acclimated Guayule (*Parthenium argentum*) Rubber-Producing Tissue," Phytochemistry, Jul. 2012, vol. 79, 12 pages.
Rakhely G., et al., "Cyanobacterial-Type, Heteropentameric, NAD+-Reducing NiFe Hydrogenase in the Purple Sulfur Photosynthetic Bacterium Thiocapsa Roseopersicina," Applied and Environmental Microbiology, Feb. 2004, vol. 70 (2), 7 pages.
Rapp V. et al., "Predicting Fuel Performance for Future HCCI Engines" Combust. Sci. Technol., 185: 735-748, Apr. 20, 2013. 15 pages.
Restriction Requirement for U.S. Appl. No. 12/352,472, dated May 27, 2011, 8 pages.
Restriction Requirement for U.S. Appl. No. 12/352,548, dated Apr. 25, 2011, 6 pages.
Restriction Requirement for U.S. Appl. No. 12/604,362, dated Jan. 11, 2012, 8 pages.
Sabatini, D.D., et al., "Mechanisms for the Incorporation of Proteins in Membranes and Organelles," Jan. 1, 1982, The Journal of Cell Biology, vol. 92, 1-22.
Sanderson K., "Chemistry: The Photon Trap," Nature, Mar. 27, 2008, vol. 452(7186), 3 pages.

(56) References Cited

OTHER PUBLICATIONS

Sapra R., et al., "A Simple Energy-Conserving System: Proton Reduction Coupled to Proton Translocation," Proceedings of the National Academy of Sciences of the United States of America, Jun. 24, 2003, vol. 100(13), 6 pages.
Sapra R., et al., "Purification and Characterization of a Membrane-Bound Hydrogenase from the Hyperthermophilic Archaeon Pyrococcus Furiosus," Journal of Bacteriology, Jun. 2000, vol. 182(12), 6 pages.
Schmidt T., et al., "Characterization of Rubber Particles and Rubber Chain Elongation in Taraxacum Koksaghyz," BMC Biochemistry, Feb. 19, 2010, vol. 11, 11 pages.
Schmitz O., et al., "HoxE—A Subunit Specific for the Pentameric Bidirectional Hydrogenase Complex (HoxEFUYH) of Cyanobacteria," Biochimica et Biophysica Acta, Apr. 22, 2002, vol. 1554(1-2), 9 pages.
Siler D.J., et al., "Composition of Rubber Particles of Hevea Brasiliensis, Parthenium Argentatum, Ficus Elastics and Euphorbia Lactiflua Indicates Unconventional Surface Structure," Plant Physiology and Biochemistry, Jan. 1997, vol. 35 (11), 9 pages.
Silvius J.R., "Thermotropic Phase Transitions of Pure Lipids in Model Membranes and their Modification by Membrane Proteins," Lipid-Protein Interactions, 1982, vol. 2, pp. 239-281,43 pages.
Singer, S.J., et al., "The Fluid Mosaic Model of the Structure of Cell Membranes," Feb. 1972, Science, vol. 175, 720-731.
Singh A.P., et al., "The Micromorphology and Protein Characterization of Rubber Particles in Ficus Carica, Ficus Benghalensis and Hevea Brasiliensis," Journal of Experimental Botany, Mar. 2003, vol. 54 (384), 8 pages.
Smith D. et al., "Solubilisation of methane monooxygenase from *Methylococcus capsulatus* (Bath)" Eur. J. Biochem, 182, pp. 667-671, Jan. 17, 1989, 6 pages.
Soboh B., et al., "Purification and Catalytic Properties of a CO-Oxidizing: H2-Evolving Enzyme Complex from Carboxydothermus Hydrogenoformans," European Journal of Biochemistry, Nov. 2002, vol. 269 (22), 10 pages.
Stadermann F.J., et al., "Nanosims: The Next Generation Ion Probe for the Microanalysis of Extra Terrestrial Material," Meteoritics and Planetary Science, 36342, vol. 34 (4), 1999. 2 pages.
Stryer L., et al., "Oxygen Binds to a Heme Prosthetic Group: Biochemistry," 1995, 4th edition, 1 page.
Stryer., "Lipid Vesicles (Liposomes) and Planar Bilayer Membranes are Valuable Model Systems," Biochemistry, 1995, 1 page.
Vincent K. A., et al., "Electrocatalytic Hydrogen Oxidation by an Enzyme at High Carbon Monoxide or Oxygen Levels," *Proceedings of the National Academy of Sciences*, Nov. 2005, vol. 102 (47), 4 pages.
Vincent K. A., et al., "Investigating and Exploiting the Electrocatalytic Properties of Hydrogenases," *Chemical Reviews*, 2007, vol. 107 (10), 48 pages.
Whalen M., et al., "Development of Crops to Produce Industrially Useful Natural Rubber," *Isoprenoid Synthesis in Plants and Microorganisms*, Jan. 2013, vol. 23, 17 pages.
White, S., Membrane Protein Insertion: The Biology-Physics Nexus, Apr. 16, 2007, J. Gen. Physiol., vol. 129, No. 5, 363-369.
Wikipedia—Bacteriorhodopsin, 2 pages, (Downloaded from the internet on Jun. 22, 2015).
Wikipedia., Hydrogenase retrieved from en.wikipedia.org/wiki/Hydrogenase on Nov. 6, 2012, 4 pages.
Woodward J., et al., "Enzymatic Production of Biohydrogen," *Nature*, Jun. 2000, vol. 405 (6790), 2 pages.
Woodward J., et al., "In Vitro Hydrogen Production by Glucose Dehydrogenase and Hydrogenase," *Nature Biotechnology*, Jul. 1996, vol. 14 (7), 3 pages.
Wu, L., et al., "Membrane targeting and translocation of bacterial hydrogenases," 2000, Arch Microbiology, 173:319-324.
Xie W., et al., "Initiation of Rubber Biosynthesis: In Vitro Comparisons of Benzophenone-Modified Diphosphate Analogues in Three Rubber-Producing Species," *Phytochemistry*, Oct. 2008, vol. 69 (14), 7 pages.
Zhang Y.H., et al., "High-Yield Hydrogen Production from Starch and Water by a Synthetic Enzymatic Pathway," *PLoS One*, May 2007, vol. 2 (5), e456, 6 pages.
Zhanhua C., et al., "Protein Subunit Interfaces: Heterodimers versus Homodimers," *Bioinformation*, Aug. 2005, vol. 1 (2), 12 pages.
Advisory Action for U.S. Appl. No. 15/499,855, filed Apr. 27, 2017 on behalf of Lawrence Livermore National Security, LLC, dated Dec. 31, 2019. 3 pages.
Alpha Helix—Wikipedia, the free encyclopedia, Nov. 7, 2014. https://web.archive.org/web/20141107095336/https://en.wikipedia.org/wiki/Alpha_helix. 15 pages.
Amar M. et al., "A Novel Apolipoprotein C-II Mimetic Peptide That Activates Lipoprotein Lipase and Decreases Serum Triglycerides in Apolipoprotein E-Knockout Mice" *The Journal of Pharmacology And Experimental Therapeutics*, pp. 227-235, Feb. 2015.
Cysteine—Wikipedia, the free encyclopedia, Sep. 20, 2015. https://web.archive.org/web/20150920101331/https://en.wikipedia.org/wiki/Cysteine.
Donia M. et al., "Small Molecules from the Human Microbiota" *Science*, vol. 349, Jul. 24, 2015, pp. 1-25.
Final Office Action for U.S. Appl. No. 16/082,924, filed Sep. 6, 2018 on behalf of Lawrence Livermore National Security, LLC, dated May 21, 2020. 50 Pages.
He Y. et al., "Apolipoprotein A1 Forms 5/5 and 5/4 Antiparallel Dimers in Human High-density Lipoprotein" *Molecular & Cellular Proteomics*, pp. 854-864,Jul. 2019.
Li J. et al., "Synthesis of many different types of organic small molecules using one automated process" *Science Mag*, vol. 347 is. 6227,Mar. 13, 2015, pp. 1221-1226.
Non-Final Office Action for U.S. Appl. No. 15/755,018, filed Feb. 23, 2018 on behalf of Lawrence Livermore National Laboratory, dated Apr. 22, 2020. 57 Pages.
Non-Final Office Action for U.S. Appl. No. 16/082,924, filed Sep. 6, 2018 on behalf of Lawrence Livermore National Security, LLC, dated Jan. 31, 2020 25 pages.
Notice of Allowance for U.S. Appl. No. 15/499,855, filed Apr. 27, 2017 on behalf of Lawrence Livermore National Security, LLC, dated Mar. 5, 2020. 43 Pages.
Notice of Allowance for U.S. Appl. No. 15/499,855, filed Apr. 27, 2017 on behalf of Lawrence Livermore National Security, LLC, dated Jun. 25, 2020. 9 pages.
Reinau M. et al. "The Diversity of FtsY-Lipid Interactions" *Biopolymers*, vol. 3, No. 7,Jan. 2010, pp. 595-606. 12 pages.
Small molecule—Wikipedia, the free encyclopedia, May 12, 2015. https://web.archive.org/web/20150512235530/https://en.wikipedia.org/wiki/Small_molecule. 4 pages.
Final office Action for U.S. Appl. No. 15/755,018, filed Feb. 23, 2018 on behalf of Lawrence Livermore National Laboratory, dated Aug. 7, 2020. 14 Pages.
Small Molecules in Metabolomics: An Introduction. Retrieved from the web on Aug. 4, 2020. https://www.ebi.ac.uk/training-beta/online/courses/metabolomics-introduction/what-is/small-molecules/ 2 Pages.
Bloedon L.T. et al., "Safety, pharmacokinetics, and pharmacodynamics of oral apoA-I mimetic peptide D-4F in high-risk cardiovascular patients" Journal of Lipid Research, vol. 49, Mar. 2008, pp. 1344-1352.
Borhani D. W. et al., "Crystal structure of truncated human apolipoprotein A-I suggests a lipid-bound conformation" Proc. Natl. Acad. Sci. USA, vol. 94, Nov. 1997, p. 12291-12296.
Elson E. L. "Fluorescence Correlation Spectroscopy: Past, Present, Future" Biophysical Journal, vol. 101, Dec. 2011, pp. 2855-2870.
Gilmore S. F. et al., "Lipid composition dictates serum stability of reconstituted high-density lipoproteins: implications for in vivo applications" Royal Society of Chemistry, Nanoscale, Mar. 2018, 10, 7420-7430. 12 pages.
Gilmore S. F. et al., "Lipid cross-linking of nanolipoprotein particles substantially enhances serum stability and cellular uptake" Applied Materials and Interfaces, Jul. 2016, 8, 20549-20557. 9 pages.
Hafner, et al., "Development status and future prospects for a vaccine against Chlamydia trachomatis infection," Vaccine, 32, (2014), pp. 1563-1571. Published online: Aug. 22, 2013. 9 Pages.

(56) References Cited

OTHER PUBLICATIONS

Kuai R. et al., "Designer vaccine nanodiscs for personalized cancer immunotherapy" Nature Materials, Dec. 2016 10 pages. DOI:10.1038/NMAT4822.

Kuai R. et al., "Designer vaccine nanodiscs for personalized cancer immunotherapy (Supplementary Information)" Nature Materials, Dec. 2016 18 pages. DOI:10.1038/NMAT4822.

Leman L.J. et al., "Molecules that Mimic Apolipoprotein A-I: Potential Agents for Treating Atherosclerosis" J Med Chem, 57(6), Mar. 2014, 56 pages.

Li L. et al., "Double Belt Structure of Discoidal High Density Lipoproteins: Molecular Basis for Size Heterogeneity" J. Mol. Biol, vol. 343, 2004, pp. 1293-1311.

Liposome—Wikipedia, the free encyclopedia. Dated: Jul. 5, 2016, 7 pages, https://en.wikipedia.org/wiki/Liposome.

Mendez A.J. "Synthetic Amphipathic Helical Peptides That Mimic Apolipoprotein A-I in Clearing Cellular Cholesterol" J Clin. Invest, vol. 94, Oct. 1994, pp. 1698-1705.

Micelle—Wikipedia, the free encyclopedia, Dated: Dec. 1, 2020, 7 pages https://en.wikipedia.org/wiki/Micelle.

Nanodisc—Wikipedia, the free encyclopedia. Dated: Jul. 5, 2016, 3 pages, https://en.wikipedia.org/wiki/Nanodisc.

Nanodisc Inc. Company Profile—ZoomInfo.com, Dated: May 25, 2015, 2 pages, https://www.zoominfo.eom/c/nanodisc/65701329.

Non-Final Office Action for U.S. Appl. No. 16/609,420, filed Oct. 29, 2019 on behalf of Lawrence Livermore National Laboratory, dated Dec. 28, 2020. 53 Pages.

Notice of Allowance for U.S. Appl. No. 15/499,855, filed Apr. 27, 2017 on behalf of Lawrence Livermore National Laboratory, dated Oct. 15, 2020. 9 pages.

Notice of Allowance for U.S. Appl. No. 15/499,855, filed Apr. 27, 2017 on behalf of Lawrence Livermore National Security LLC dated Jan. 25, 2021 9 pages.

Plotkin, et al., Vaccines, WB Saunders Company, p. 571. Year: 1988. 2 Pages.

Popot J.L. "Alternatives to Detergents for Handling Membrane Proteins in Aqueous Solutions" Membrane Proteins in Aqueous Solutions, Jun. 2018, pp. 97-149.

Popovic K. et al., "Structure of saposin A lipoprotein discs" PNAS, vol. 109 No. 8, Feb. 2012, pp. 2908-2912.

Restriction Requirement for U.S. Appl. No. 16/159,189, filed Oct. 12, 2018 on behalf of Lawrence Livermore National Security, LLC, dated Jan. 29, 2021. 6 Pages.

Segrest J. P. "Amphipathic Helix Motif: Classes and Properties" Proteins: Structure, Function, and Genetics, vol. 8, 1990, pp. 103-117.

Segrest J.P. et al., "Pathogenesis of atherosclerosis" Current Opinion in Cardiology, vol. 9,1994, pp. 404-410.

Spuhler P. et al., "Binding of Apolipoprotein A-I Model Peptides to Lipid Bilayers" The Journal of Biological Chemistry, vol. 269 No. 39, Sep. 1994, p. 23904-23910.

Swainsbury D.J.K. et al., "The effectiveness of styrene-maleic acid (SMA) copolymers for solubilization of integral membrane proteins from SMA-accessible and SMA-resistant membranes" BBA-Biomembranes, Jul. 2017, pp. 2133-2143.

Troutt J.S. et al., "An apolipoprotein A-I mimetic dose-dependently increases the formation of preB1 HDL in human plasma" Journal of Lipid Research, vol. 49, Mar. 2008, pp. 581-587.

Watson C.E. et al., "Treatment of patients with cardiovascular disease with L-4F, an apo-A1 mimetic, did not improve select biomarkers of HDLK function" Journal of Lipid Research, vol. 52, Feb. 2011, pp. 361-373.

Wool G.D. "Apolipoprotein A-I mimetic peptide helix number and helix linker influence potentially anti-atherogenic properties" Journal of Lipid Research, vol. 48, 2008, pp. 1268-1283.

Zhao Y. et al., "Self-Assembling Cyclic D,L-a-Peptides as Modulators of Plasma HDL Function. A Supramolecular Approach toward Antiatherosclerotic Agents" ACS Central Science, vol. 3, Jun. 2017, pp. 639-646.

Bezrukov S. M. "Functional conseguences of lipid packing stress" Current Opinion in Colloid & Interface Science 5, Jan. 2000, pp. 237-243.

Denisov I. G. "Thermotropic Phase Transition in Soluble Nanoscale Lipid Bilayers" J Phys Chem B., Aug. 18, 2005, 109(32), 23 pages.

"Drug" Wikipedia, the free encyclopedia. Downloaded through the Wayback Machine for Dec. 8, 2011. 5 pages.

Klevens H. B. "Structure and Aggregation in Dilute Solutions of Surface Active Agents" The Journal of the American Oil Chemists Society, Feb. 1953, 7 pages.

Marsh D. "Equation of State for Phospholipid Self-Assembly" Biophysical Journal, vol. 110, Jan. 2016, pp. 188-196.

Martinez D et al., "Lipid Internal Dynamics Probed in Nanodiscs" ChemPhysChem, Jan. 2017, 18, pp. 2651-2657.

Non-Final Office Action for U.S. Appl. No. 15/755,018, filed Feb. 23, 2018, on behalf of Lawrence Livermore National Laboratory, dated Jul. 16, 2021. 22 Pages.

Non-Final Office Action for U.S. Appl. No. 16/082,924, filed Sep. 6, 2018 on behalf of Lawrence Livermore National Security, LLC dated May 25, 2021 25 pages.

Non-Final Office Action for U.S. Appl. No. 16/159,189, filed Oct. 12, 2018 on behalf of Lawrence Livermore National Security, LLC, dated Jun. 24, 2021. 32 Pages.

Notice of Allowance for U.S. Appl. No. 15/499,855, filed Apr. 27, 2017 on behalf of Lawrence Livermore National Security, LLC, dated May 14, 2021. 10 Pages.

Notice of Allowance for U.S. Appl. No. 16/609,420, filed Oct. 29, 2019 on behalf of Lawrence Livermore National Laboratory, dated Jul. 28, 2021. 7 Pages.

Notice of Allowance for U.S. Appl. No. 16/609,420, filed Oct. 29, 2019 on behalf of Lawrence Livermore National Laboratory, dated May 6, 2021. 10 Pages.

Pollock, N.L. et al., "Structure and function of membrane proteins encapsulated in a polymer-bound lipid bilayer", Biochimica etBiophysica Acta (BBA)—Biomembranes (2017), 9 pages; Internet: dx.doi.org/10.1016/j.bbamem.2017.08.012.

Schachter T. et al., "Confinement in Nanodiscs Anisotropically Modifies Lipid Bilayer Elastic Properties" J. Phys. Chem. B, Jul. 2020, vol. 124, pp. 7166-7175.

Shelby M. et al., "Cell-Free Co-Translational Approaches for Producing Mammalian Receptors: Expanding the Cell-Free Expression Toolbox Using Nanolipoproteins" Frontiers in Pharmacology, vol. 10 No. 744, Jul. 2019, pp. 1-12.

Stepien P. et al., "Comparative EPR studies on lipid bilayer properties in nanodiscs and liposomes" Biochimica et Biophysica Acta, Oct. 2014, pp. 60-66.

Tanaka, M. et al. "Preparation and Characterization of Reconstituted Lipid-Synthetic Polymer Discoidal Particles" Langmuir, (2015),vol. 31, Issue 46, 12719-12726. 8 pages. Internet: doi.10.1021/acs.langmuir.5b03438.

* cited by examiner

Helix #1 residues 24-52 kveqavetep epelrqqtew qsg|qrwelal grfwdylrwv qtseqvqee ll|s|sqvtqel|

Helix #2 residues 54-82    Helix #3 residues 86-126

|ralmdetmke lkaykselee ql|tpv|aeetr arlskelqaa qarlgadmed vrgrlvqyrg|

Helix #4 residues 129-165

|evqamlg|q|st|eelrvrlash lrklrkrllr daddlqkrla vyqag|

*FIG. 3*

SEQUENCE LISTING

<160> NUMBER OF SEQ ID NOS: 11

<210> SEQ ID NO 1
<211> LENGTH: 29
<212> TYPE: PRT
<213> ORGANISM: Homo sapiens

<400> SEQUENCE: 1

Gln Arg Trp Glu Leu Ala Leu Gly Arg Phe Trp Asp Tyr Leu Arg Trp
1               5                   10                  15

Val Gln Thr Leu Ser Glu Gln Val Gln Glu Glu Leu Leu
            20                  25

<210> SEQ ID NO 2
<211> LENGTH: 29
<212> TYPE: PRT
<213> ORGANISM: Homo sapiens

<400> SEQUENCE: 2

Ser Gln Val Thr Gln Glu Leu Arg Ala Leu Met Asp Glu Thr Met Lys
1               5                   10                  15

Glu Leu Lys Ala Tyr Lys Ser Glu Leu Glu Glu Gln Leu
            20                  25

<210> SEQ ID NO 3
<211> LENGTH: 42
<212> TYPE: PRT
<213> ORGANISM: Homo sapiens

<400> SEQUENCE: 3

Ala Glu Glu Thr Arg Ala Arg Leu Ser Lys Glu Leu Gln Ala Ala Gln
1               5                   10                  15

Ala Arg Leu Gly Ala Asp Met Glu Asp Val Arg Gly Arg Leu Val Gln
            20                  25                  30

Tyr Arg Gly Glu Val Gln Ala Met Leu Gly
        35                  40

<210> SEQ ID NO 4
<211> LENGTH: 37
<212> TYPE: PRT
<213> ORGANISM: Homo sapiens

<400> SEQUENCE: 4

Ser Thr Glu Glu Leu Arg Val Arg Leu Ala Ser His Leu Arg Lys Leu
1               5                   10                  15

Arg Lys Arg Leu Leu Arg Asp Ala Asp Asp Leu Gln Lys Arg Leu Ala
            20                  25                  30

Val Tyr Gln Ala Gly
        35

<210> SEQ ID NO 5
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Xaa is 2-Aminoisobutyric acid
<220> FEATURE:
<221> NAME/KEY: MISC_FEATURE
<222> LOCATION: (12)..(12)
<223> OTHER INFORMATION: Xaa is 2-Aminoisobutyric acid
<220> FEATURE:
<221> NAME/KEY: MISC_FEATURE
<222> LOCATION: (17)..(17)
<223> OTHER INFORMATION: Xaa is 2-Aminoisobutyric acid
<220> FEATURE:
<221> NAME/KEY: MISC_FEATURE
<222> LOCATION: (22)..(22)
<223> OTHER INFORMATION: Xaa is 2-Aminoisobutyric acid
<220> FEATURE:
<221> NAME/KEY: MISC_FEATURE
<222> LOCATION: (26)..(26)
<223> OTHER INFORMATION: Xaa is 2-Aminoisobutyric acid

<400> SEQUENCE: 5

Gln Arg Trp Glu Leu Xaa Leu Gly Arg Phe Trp Xaa Tyr Leu Arg Trp
1               5                   10                  15

Xaa Gln Thr Leu Ser Xaa Gln Val Gln Xaa Glu Leu Leu
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa is 2-Aminoisobutyric acid
<220> FEATURE:
<221> NAME/KEY: MISC_FEATURE
<222> LOCATION: (9)..(9)
<223> OTHER INFORMATION: Xaa is 2-Aminoisobutyric acid
<220> FEATURE:
<221> NAME/KEY: MISC_FEATURE
<222> LOCATION: (14)..(14)
<223> OTHER INFORMATION: Xaa is 2-Aminoisobutyric acid
<220> FEATURE:
<221> NAME/KEY: MISC_FEATURE
<222> LOCATION: (20)..(20)
<223> OTHER INFORMATION: Xaa is 2-Aminoisobutyric acid
<220> FEATURE:
<221> NAME/KEY: MISC_FEATURE
<222> LOCATION: (25)..(25)
<223> OTHER INFORMATION: Xaa is 2-Aminoisobutyric acid

<400> SEQUENCE: 6

Ser Gln Xaa Thr Gln Glu Leu Arg Xaa Leu Met Asp Glu Xaa Met Lys
1               5                   10                  15

Glu Leu Lys Xaa Tyr Lys Ser Glu Xaa Glu Glu Gln Leu
            20                  25

<210> SEQ ID NO 7
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (6)..(6)
<223> OTHER INFORMATION: Xaa is 2-Aminoisobutyric acid
<220> FEATURE:
<221> NAME/KEY: MISC_FEATURE
<222> LOCATION: (14)..(14)
<223> OTHER INFORMATION: Xaa is 2-Aminoisobutyric acid
<220> FEATURE:
<221> NAME/KEY: MISC_FEATURE
<222> LOCATION: (21)..(21)
<223> OTHER INFORMATION: Xaa is 2-Aminoisobutyric acid
<220> FEATURE:
<221> NAME/KEY: MISC_FEATURE
<222> LOCATION: (26)..(26)
<223> OTHER INFORMATION: Xaa is 2-Aminoisobutyric acid
<220> FEATURE:
<221> NAME/KEY: MISC_FEATURE
<222> LOCATION: (35)..(35)
<223> OTHER INFORMATION: Xaa is 2-Aminoisobutyric acid

<400> SEQUENCE: 7

Ala Glu Glu Thr Arg Xaa Arg Leu Ser Lys Glu Leu Gln Xaa Ala Gln
1               5                   10                  15

Ala Arg Leu Gly Xaa Asp Met Glu Asp Xaa Arg Gly Arg Leu Val Gln

```
                 20                  25                  30

Tyr Arg Xaa Glu Val Gln Ala Met Leu Gly
         35                  40

<210> SEQ ID NO 8
<211> LENGTH: 37
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: Xaa is 2-Aminoisobutyric acid
<220> FEATURE:
<221> NAME/KEY: MISC_FEATURE
<222> LOCATION: (10)..(10)
<223> OTHER INFORMATION: Xaa is 2-Aminoisobutyric acid
<220> FEATURE:
<221> NAME/KEY: MISC_FEATURE
<222> LOCATION: (24)..(24)
<223> OTHER INFORMATION: Xaa is 2-Aminoisobutyric acid
<220> FEATURE:
<221> NAME/KEY: MISC_FEATURE
<222> LOCATION: (32)..(32)
<223> OTHER INFORMATION: Xaa is 2-Aminoisobutyric acid

<400> SEQUENCE: 8

Ser Thr Glu Glu Xaa Arg Val Arg Leu Xaa Ser His Leu Arg Lys Leu
1               5                   10                  15

Arg Lys Arg Leu Leu Arg Asp Xaa Asp Asp Leu Gln Lys Arg Leu Xaa
                 20                  25                  30

Val Tyr Gln Ala Gly
         35

<210> SEQ ID NO 9
<211> LENGTH: 43
<212> TYPE: PRT
<213> ORGANISM: Bombyx mori

<400> SEQUENCE: 9

Lys Val Ser Ser Asn Val Gln Glu Thr Asn Glu Lys Leu Ala Pro Lys
1               5                   10                  15

Ile Lys Ala Ala Tyr Asp Asp Phe Ala Lys Asn Thr Gln Glu Val Ile
                 20                  25                  30

Lys Lys Ile Gln Glu Ala Ala Asn Ala Lys Gln
         35                  40

<210> SEQ ID NO 10
<211> LENGTH: 44
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (11)..(11)
<223> OTHER INFORMATION: Xaa is 2-Aminoisobutyric acid
<220> FEATURE:
<221> NAME/KEY: MISC_FEATURE
<222> LOCATION: (21)..(21)
<223> OTHER INFORMATION: Xaa is 2-Aminoisobutyric acid
<220> FEATURE:
<221> NAME/KEY: MISC_FEATURE
<222> LOCATION: (31)..(31)
<223> OTHER INFORMATION: Xaa is 2-Aminoisobutyric acid
<220> FEATURE:
<221> NAME/KEY: MISC_FEATURE
<222> LOCATION: (39)..(39)
```

```
<223> OTHER INFORMATION: Xaa is 2-Aminoisobutyric acid

<400> SEQUENCE: 10

Lys Val Ser Ser Asn Val Gln Glu Thr Asn Xaa Lys Leu Ala Pro Lys
1               5                   10                  15

Lys Ile Lys Ala Xaa Tyr Asp Asp Phe Ala Lys Asn Thr Gln Xaa Val
            20                  25                  30

Ile Lys Lys Ile Gln Glu Xaa Ala Asn Ala Lys Gln
        35                  40

<210> SEQ ID NO 11
<211> LENGTH: 164
<212> TYPE: PRT
<213> ORGANISM: Homo sapiens

<400> SEQUENCE: 11

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Ser Glu Gln Val Gln Glu
            35                  40                  45

Glu Leu Leu Ser Ser Gln Val Thr Gln Glu Leu Arg Ala Leu Met Asp
50                  55                  60

Glu Thr Met Lys Glu Leu Lys Ala Tyr Lys Ser Glu Leu Glu Glu Gln
65                  70                  75                  80

Leu Thr Pro Val Ala Glu Glu Thr Arg Ala Arg Leu Ser Lys Glu Leu
                85                  90                  95

Gln Ala Ala Gln Ala Arg Leu Gly Ala Asp Met Glu Asp Val Arg Gly
            100                 105                 110

Arg Leu Val Gln Tyr Arg Gly Glu Val Gln Ala Met Leu Gly Gln Ser
            115                 120                 125

Thr Glu Glu Leu Arg Val Arg Leu Ala Ser His Leu Arg Lys Leu Arg
        130                 135                 140

Lys Arg Leu Leu Arg Asp Ala Asp Asp Leu Gln Lys Arg Leu Ala Val
145                 150                 155                 160

Tyr Gln Ala Gly
```

SYNTHETIC APOLIPOPROTEINS, AND RELATED COMPOSITIONS METHODS AND SYSTEMS FOR NANOLIPOPROTEIN PARTICLES FORMATION

CROSS REFERENCE TO RELATED APPLICATIONS

The present application is the U.S. National Stage of International Patent Application No. PCT/US2016/051172 filed on Sep. 9, 2016 which claims priority to U.S. Provisional Application No. 62/217,316, entitled "Synthetic Apolipoproteins, and related Compositions Methods and Systems for Nanolipoprotein Particles Formation" filed on Sep. 11, 2015, the content of which is incorporated herein by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

FIELD

The present disclosure relates to nanolipoprotein particles (NLPs) and, in particular, to synthetic apolipoproteins and related methods and systems for nanolipoprotein particles formation.

BACKGROUND

Nanolipoprotein particles are nanometer-sized particles usually comprised of an amphipathic lipid bilayer and an apolipoprotein. NLPs assembled with human apolipoproteins have been used for various biotechnology applications, such as membrane protein stabilization/solubilization, drug delivery, and diagnostic imaging.

In some instances, NLPs can self-assemble under appropriate conditions into nano-scale amphipathic apolipoproteins-stabilized lipid bilayer particles possibly comprising additional molecules, such as one or more integral membrane proteins or other proteins and molecules attached to the amphipathic component of the NLP. The self-assembled particles are typically formed by an apolipoprotein encircling a nanometer scale lipid bilayer defining a nanolipoprotein particle.

Despite the advancement of this technology, providing NLPs including desired functionalities and/or with a desired stability can be challenging.

SUMMARY

Provided herein, are synthetic apolipoproteins, membrane forming lipids and related NLP fabrication/formation, methods and systems. In particular, in some embodiments the methods and systems herein disclosed allow the chemical synthesis of apolipoproteins and combining with lipids to form NLPs.

According to a first aspect, a synthetic apolipoprotein is provided. The synthetic apolipoprotein comprises a plurality of helical segments each having a primary structure configured to form an alpha helix secondary structure wherein at least one helical segment of the plurality of helical segments comprises a plurality of hydrophobic amino acids and a plurality of hydrophilic amino acids positioned in the primary structure to provide an amphipathic alpha helix secondary structure wherein the plurality of hydrophobic amino acids form an hydrophobic helix face and the plurality of hydrophilic amino acids form an opposing hydrophilic helix face and wherein at least one helical segment comprises one or more non-natural α,α'-dialkyl amino acids within the hydrophobic helical face.

According to a second aspect, a synthetic apolipoprotein is provided. The synthetic apolipoprotein comprises a plurality of helical segments each having a primary structure configured to form an alpha helix secondary structure wherein at least one helical segment of the plurality of helical segment comprises a plurality of hydrophobic amino acids and a plurality of hydrophilic amino acids, the plurality of hydrophobic amino acids comprising at least one α,α'-dialkyl amino acid, the plurality of hydrophobic amino acids positioned in the primary structure with a periodicity $i_o + x_o$ where $i_o$ is a recurring position of a hydrophobic amino acid of plurality of hydrophobic amino acids in the primary structure and $x_o$ is a number of amino acids in the helical segment between a first occurrence and a second occurrence of the recurring position $i_o$, the plurality of hydrophilic amino acids positioned in the primary structure with a periodicity $i_i + x_i$ where $i_i$ is a recurring position of a hydrophilic amino acid of the plurality of hydrophilic amino acids in the primary structure and $x_i$ is a number of amino acids in the helical segment between a first occurrence and a second occurrence of the recurring position $i_i$ and wherein $x_o$ and $x_i$ are independently an integer from 3 to 9.

According to a third aspect, a nanolipoprotein particle (NLP) is described, comprising a membrane forming lipid, and a scaffold protein, wherein the scaffold protein is a synthetic apolipoprotein herein described.

According to a fourth aspect, a method and system to provide a synthetic apolipoprotein is described. The method comprises synthesizing a plurality of helical segments, each helical segment comprising a plurality of hydrophobic amino acid and a plurality of hydrophilic amino acid, each helical segment having a primary structure configured to form an amphipathic alpha helical secondary structure in which the plurality of hydrophobic amino acids form a hydrophobic cluster or helical face and the plurality of hydrophilic amino acid form a hydrophilic cluster or helical face. Each helical segment has an N-terminal end and a C-terminal end. The method further comprises, ligating the plurality of alpha-helical segments through the N-terminal end or the C-terminal end to form a synthetic apolipoprotein via at least one synthetic chemical linkage. In the method at least one helical segment of the plurality of helical segment comprises one or more α,α'-dialkyl amino acids within the hydrophobic cluster or helical face. The system comprises at least two of a plurality of hydrophobic amino acid comprising one or more α,α'-dialkyl amino acids, a plurality of hydrophilic amino acid and optionally additional reagents for simultaneous combined or sequential use in the method herein described.

According to a fifth aspect, a method and system to form nanolipoprotein particles (NLPs) are provided. The method comprises synthesizing a synthetic apolipoprotein according to a method herein described. The method also comprises, combining the synthetic apolipoprotein with membrane forming lipids to form a nanolipoprotein particle. The system comprises at least two of one or more synthetic apolipoproteins herein described, membrane forming lipids and optionally one or more target proteins or additional reagents for simultaneous combined or sequential use in the method herein described.

Synthetic apolipoproteins herein described can provide in several embodiments apolipoproteins with amphipathicity and conformational/helical stability, which can be used in several embodiments to provide stable and/or high size nanolipoprotein particles (NLPs).

Synthetic apolipoproteins, nanolipoprotein particles and related methods and systems herein described can be used in some embodiments in connection with various applications wherein control of the NLP size is desired, for example to accommodate and facilitate isolation of functional biosynthetic enzyme complexes ranging from biopolymer synthesis [e.g., polysaccharides (cellulose), polyesters, polyamides, polyisoprenes and additional enzymes identifiable by a skilled person] to photon capture [PS II].

Synthetic apolipoproteins, nanolipoproteinparticles (NLPs) and related methods and systems herein described can be used in some embodiments in connection with NLP configured to isolate, stabilize and/or solubilize membrane proteins.

Synthetic apolipoproteins, nanolipoprotein particles (NLPs) and related methods and systems herein described can be used in some embodiments in connection with NLP configured as a vehicle for delivery of compounds such as therapeutics to a specific target destination and facilitating crossing or passage through the blood-brain barrier (BBB).

Synthetic apolipoproteins, nanolipoprotein particles (NLPs) and related methods and systems herein described can be used in some embodiments in connection with NLP configured as a platform for vaccine development and use.

Synthetic apolipoproteins, nanolipoprotein particles (NLPs) and related methods and systems herein described can be used in some embodiments in connection with NLP configured as a platform for immnostimulating agents.

Synthetic apolipoproteins, nanolipoprotein particles (NLPs) and related methods and systems herein described can be used in some embodiments in connection with NLP configured as a vehicle for scavenging molecular entities.

Synthetic apolipoproteins, nanolipoprotein particles (NLPs) and related methods and systems herein described can be used in some embodiments in connection with NLP comprising synthetic apolipoproteins designed to dimerize or multimerise, e.g., to augment their flexibility in terms of defining various particles' sizes.

Synthetic apolipoproteins, nanolipoprotein particles (NLPs) and related methods and systems herein described can be used in some embodiments in connection with NLP comprising synthetic apolipoproteins designed to contain cell-targeting moieties.

Synthetic apolipoproteins, nanolipoprotein particles (NLPs) and related methods and systems herein described can be used in some embodiments in connection with chemical synthesis of apolipoproteins allowing for realistic scale-up and manufacturing complete with documentation needed to satisfy regulatory considerations and compliance issues prior to possible FDA filing.

Synthetic apolipoproteins, nanolipoprotein particles (NLPs) and related methods and systems herein described can be applied in several fields including basic biology research, applied biology, bio-engineering, bio-energy, medical research, medical diagnostics, therapeutics, biofuels, and in additional fields where NLPs may be used.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 1 shows a cartoon illustration of six putative helix positions a, b, c, d, e, f, and g, on a helical wheel representation.

FIG. 3 provides an example of the amino acid sequences of the four helical segments of Apolipoprotein E4, 22 k fragment (SEQ ID NO: 11), which is capable of forming NLP structures.

FIG. 11 provides models of NLPs with and without an integral membrane protein. In particular

DETAILED DESCRIPTION

Figure 1:
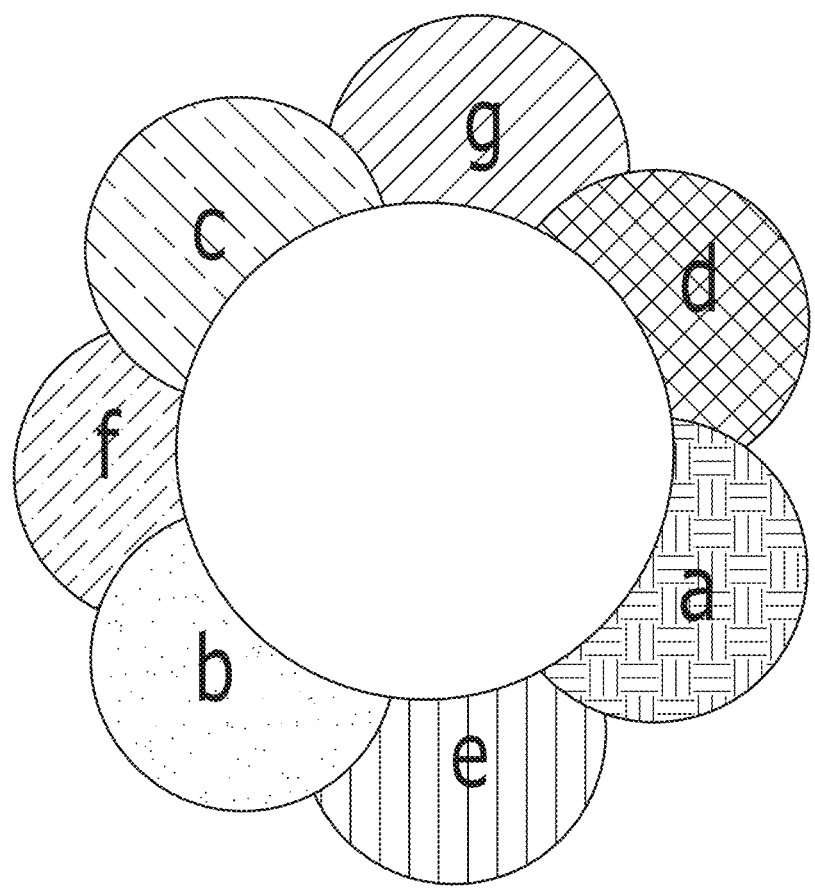
FIG. 1 shows a generic helical wheel representation of aprotein alpha helix structure according to embodiments herein described. In particular

Provided herein are synthetic apolipoproteins designed to be used in formation of nanolipoprotein particles (NLP) and related NLPs, methods and systems to form NLPs.

The term "synthetic" as used herein indicates any product and/or process which cannot be found in nature. In particular, the term synthetic indicates any product and/or process that involves practices common to synthetic organic chemistry and encompass any chemical bond forming process, e.g., amide bond formation, and related products. Accordingly, synthetic molecules comprise molecules that can include chemical moieties not present in the naturally occurring molecules and molecules comprising portions that are naturally occurring and portions that chemically synthesized.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise, a molecule having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immuno precipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can surround the lipids, creating the lipoprotein particle that is itself water-soluble, and can thus be carried through water-based circulation (e.g., blood, lymph in vivo or in vitro).

Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo C-II, and apo C-IV), Apolipoproteins D, Apolipoproteins E, and Apolipoproteins H. For example apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

In embodiments herein described, synthetic apolipoproteins are provided which are apolipoproteins that comprise at least one non-natural amino acid and/or amino acid residues linked together by a series of peptide or amide bonds. The latter will be formed using established chemical synthetic methods which are identifiable by a skilled person.

As used herein the term "amino acid", "amino acidic monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

The term "non-natural amino acids" or "artificial amino acids" indicate not naturally encoded or found in the genetic code of any organisms and typically comprise non-proteinogenic amino acids that either occur naturally or are chemically synthesized. Accordingly, non-natural amino acids comprise molecules that can be coupled together using standard amino acid coupling chemistry, and that have molecular structures that do not resemble the naturally occurring amino acids. Exemplary non-natural amino acids comprise e.g., α,α'-dialkyl-amino acids such as amino isobutyric acid (Aib) or cyclopentyl glycine and analogs of naturally occurring amino acids. The term "amino acid analog" refers to an amino acid in which one or more individual atoms have been replaced, either with a different atom, isotope, or with a different functional group but is otherwise identical to original amino acid from which the analog is derived. (Lam, K. S. et al., 1997. Anticancer Drug Des. 1997 Apr. 12(3): 145-67).

A synthetic "covalent linkage" as used herein indicates a stable chemical bond that involves the sharing of electron pairs between atoms. In particular, covalent linkage between natural and non natural amino acid in polypeptide described herein is typically defined as an amide bond. The latter involves specific chemical activation of the —COOH group utilizing a variety of activating groups and directed condensation with an amino group; the elimination of water (condensation reaction) results in a stable amide bond. In the context of polypeptide or protein synthesis the amide bond is referred to as a peptide bond.

Accordingly, synthetic apolipoproteins can be provided by using process such as conventional solid-phase peptide chemistry (SPPS) or Merrifield peptide synthesis and additional methods that allow chemical conjugation and ligation of amino acids as will be understood by a skilled person. This approach and detailed method descriptions have been documented thoroughly in the scientific literature (Solid Phase Peptide Synthesis, J M Stewart & J D Young, Pierce Chemical Company, 1984).

In some embodiments, a synthetic apolipoprotein can comprise a plurality of helical peptide segments each having a primary structure configured to form an alpha helix secondary structure.

The term "segment" or "domain" as related to the protein indicates any continuous part of a protein sequence from single amino acid up to the full protein associated to an identifiable structure within the protein. An "identifiable structure" in the sense of the disclosure indicates a spatial arrangement of the primary structure or portions thereof which can be detected by techniques such as crystallography, hydrophobicity analysis or additional techniques known by a skilled person. In some instances, a protein segment can comprise one or more secondary structures of the protein.

The "secondary structure" of a protein refers to local sub-structures with a repeating geometry identifiable within crystal structure of the protein, circular dichroism or by additional techniques identifiable by a skilled person. In some instances, a secondary structure of a protein can be identified by the patterns of hydrogen bonds between backbone amino and carboxyl groups. Secondary structures can also be defined based on a regular, repeating, geometry, being constrained to approximate values of the dihedral angles ψ and φ of the amino acids in the secondary structure unit on the Ramachandran plot. Two main types of secondary structure are the alpha helix and the beta strand or beta sheets as will be identifiable by a skilled person. Both the alpha helix and the beta sheet represent a way of establishing non-covalent hydrogen bonds between constituents of the peptide backbone, thus forming secondary structural features. Secondary structure formation can be promoted by formation of hydrogen bonds between backbone atoms. Amino acids that can minimize formation of a secondary structure by destabilizing the structure of the hydrogen bonding interactions are referred to as secondary structure breakers. Amino acids that can promote formation of a secondary structure by stabilizing formation of hydrogen bonding interactions are referred to as structure makers.

The term "alpha helix" or "α-helix" indicates a right-hand-coiled or spiral conformation (helix) of a polypeptide in which every backbone N—H group donates a hydrogen bond to the backbone C═O group of the amino acid four residues earlier facilitating hydrogen bonding. The alpha helix is a common secondary structure of proteins and is also sometimes called a classic Pauling-Corey-Branson alpha helix. The name $3.6_{13}$-helix is also used for this type of helix, denoting the number of residues per helical turn, and 13 atoms being involved in the ring formed by the hydrogen bond.

In some embodiments, the natural and/or non-natural amino acids are positioned in a primary structure of the synthetic apolipoprotein to provide and facilitate amphipathic alpha helix formation.

The "amphipathic helix" indicates an alpha helix characterized by a spatial segregation of hydrophobic and hydrophilic amino acid residues in hydrophobic and hydrophilic regions typically located on opposite faces of the helix which renders the alpha helix amphipathic. The clustered nonpolar residues can then stabilize and encourage lipid molecules to form lipoprotein complexes and stabilize lipid bilayer conformations underpinning the NLP nanoconstruct.

Hydrophilic amino acids are amino acid that are considered to be soluble in water and have polar side chains, e.g. comprising —COOH, —OH, —$NH_3$, groups and other groups identifiable by a skilled person. Exemplary hydrophilic amino acid comprise polar or charged amino acid (e.g. polar naturally occurring amino acid serine (Ser), threonine (Thr), asparagine (Asn), glutamine (Gln), and tyrosine (Tyr); and charged naturally occurring amino acid such as lysine (Lys) (+), arginine (Arg) (+), aspartate (Asp) (−) and glutamate (Glu) (−). Hydrophobic amino acids are amino acids that have aliphatic or saturated hydrocarbon side chains (e.g natural occurring glycine (Gly), alanine (Ala), valine (Val), leucine (Leu), isoleucine (Ile), proline (Pro), phenylalanine (Phe), methionine (Met), and tryptophan (Trp). Polar amino acid can also be involved in hydrogen bond.

In particular, in embodiments herein described, one or more non-natural amino acid can be included in at least one helical segment of the synthetic apolipoprotein. In particular, in some embodiments at least one and possibly a plurality of α,α'-dialkyl-amino acids such as amino isobutyric acid (Aib) or cyclopentyl glycine or derivative thereof can be comprised in at least one helical segment of the apolipoprotein herein described.

"α,α'-dialkyl-amino acids" indicate non-natural amino acids wherein the alpha carbon of the amino acid is substitute by two alkyl groups, which can be substituted or unsubstituted C1-C6 linear or branched hydrocarbon chains In particular, exemplary alkyl chains comprise methyl, ethyl, propyl and the like but also benzyl, 2-phenylethyl, fluoromethyl, chloromethyl, methoxymethyl, 2-methoxyethyl, ethoxymethyl, and additional alkyl chains identifiable by a skilled person.

Derivatives of α,α'-disubstituted amino acids include α,α'-dialkyl-amino acids modified to include additional groups or moieties while preserving the biological and chemical activities associated to the dialkyl groups presented on the alpha carbon of the disubstituted amino acid.

Exemplary derivatives of α,α'-disubstituted amino acid comprise Cyclic Quaternary α-Amino Acids such as: Boc-2-aminoisobutyric acid, Fmoc-2-aminoisobutyric acid, Fmoc-αMe-D-Asp(OtBu)-OH, (R)-Fmoc-2-amino-2-methyl-succinic acid-4-tert-butyl ester, Fmoc-aMe-L-Asp (OtBu)-OH, (S)-Fmoc-2-amino-2-methyl-succinic acid-4-tert-butyl ester, Boc-α-methyl-L-phenylalanine, Fmoc-α-methyl-L-phenylalanine, Boc-α-methyl-D-4-bromophenylalanine, Fmoc-α-methyl-D-4-bromophenylalanine, Boc-α-methyl-L-4-bromophenylalanine, Fmoc-α-methyl-L-4-bromophenylalanine, Boc-1-amino-cyclopropane carboxylic acid, Fmoc-1-amino-cyclopropane carboxylic acid, Boc-1-amino-cyclobutane carboxylic acid, Fmoc-1-amino-cyclobutane carboxylic acid, Boc-1-amino-cyclopentane carboxylic acid, Fmoc-1-amino-cyclopentane carboxylic acid, Boc-1-amino-cyclohexane carboxylic acid, Fmoc-1-amino-cyclohexane carboxylic acid, Boc-1-amino-cycloheptane carboxylic acid, Fmoc-1-amino-cycloheptane carboxylic acid, Boc-1-amino-cyclooctane carboxylic acid, Fmoc-1-amino-cyclooctane carboxylic acid, Fmoc-8-amino-1,4-dioxa-spiro[4,5]decane-8-carboxylic acid, Fmoc-1-amino-4-oxo-cyclohexane carboxylic acid, Boc-cis-1-amino-4-phenyl-cyclohexane carboxylic acid, Fmoc-cis-1-amino-4-phenyl-cyclohexane carboxylic acid, Fmoc-4-amino-tetrahydropyran-4-carboxylic acid, Fmoc-4-amino-tetrahydrothiopyran-4-carboxylic acid, (R,S)-Boc-1-aminoindane-1-carboxylic acid, (R,S)-Fmoc-1-aminoindane-1-carboxylic acid, Boc-2-aminoindane-2-carboxylic acid, Fmoc-2-aminoindane-2-carboxylic acid, (R,S)-Boc-2-aminotetraline-2-carboxylic acid, (R,S)-Fmoc-2-aminotetraline-2-carboxylic acid, (R,S)-3-Boc-amino-9-Boc-1,2,3,4-tetrahydro-carbazole-3-carboxylic acid, (R,S)-3-Fmoc-amino-9-Boc-1,2,3,4-tetrahydro-carbazole-3-carboxylic acid, Boc-4-amino-1-Z-piperidine-4-carboxylic acid, Fmoc-4-amino-1-Boc-piperidine-4-carboxylic acid, and Z-4-amino-1-Boc-piperidine-4-carboxylic acid. Aliphatic α-Amino Acid Derivatives includes but is not limited to: Boc-D-allylglycine-DCHA, Fmoc-D-allylglycine, Boc-L-allylglycine.DCHA, Fmoc-L-allylglycine, Fmoc-D-propargylglycine, Fmoc-L-propargylglycine, Boc-L-alpha-t-butylglycine, Fmoc-L-alpha-t-butylglycine, Boc-D-alpha-t-amylglycine, Fmoc-D-alpha-t-amylglycine, Boc-L-alpha-t-amylglycine, Fmoc-L-alpha-t-amylglycine, (S)-Boc-1-adamantyl-glycine, (S)-Fmoc-1-adamantyl-glycine, Boc-D-cyclopropylglycine, Fmoc-D-cyclopropylglycine, Boc-L-cyclopropylglycine, Fmoc-L-cyclopropylglycine, Boc-D-cyclopentyl-glycine, Fmoc-D-cyclopentyl-glycine, Boc-L-cyclopentyl-glycine, Fmoc-L-cyclopentyl-glycine, Boc-L-beta-t-butylalanine, Fmoc-L-beta-t-butylalanine, Boc-beta-cyclopropyl-D-alanine.DCHA, Fmoc-beta-cyclopropyl-D-alanine, Boc-beta-cyclopropyl-L-alanine.DCHA, Fmoc-beta-cyclopropyl-L-alanine, Fmoc-beta-cyclobutyl-D-alanine, Fmoc-beta-cyclobutyl-L-alanine, Boc-beta-cyclohexyl-D-alanine monohydrate, Fmoc-beta-cyclohexyl-D-alanine, Boc-beta-cyclohexyl-L-alanine monohydrate, Fmoc-beta-cyclohexyl-L-alanine, Boc-D-2-aminobutyric acid.DCHA, Fmoc-D-2-aminobutyric acid, Boc-L-2-aminobutyric acid, Fmoc-L-2-aminobutyric acid, (R,S)-Boc-2-amino-4,4-difluoro-butyric acid, (R,S)-Fmoc-2-amino-4,4-difluoro-butyric acid, (R,S)-Boc-2-amino-4,4,4-trifluoro-butyric acid, (R,S)-Fmoc-2-amino-4,4,4-trifluoro-butyric acid, (S)-Boc-2-amino-4,4,4-trifluoro-butyric acid, (S)-Fmoc-2-amino-4,4,4-trifluoro-butyric acid, H-D-norvaline, Boc-D-norvaline, Fmoc-D-norvaline, H-L-norvaline, Boc-L-norvaline, Fmoc-L-norvaline, H-D-norleucine, Boc-D-norleucine, Fmoc-D-norleucine, H-L-norleucine, Boc-L-norleucine, Fmoc-L-norleucine, Boc-4,5-dehydro-D-leucine.DCHA, Fmoc-4,5-dehydro-D-leucine, Boc-4,5-dehydro-L-leucine.DCHA, Fmoc-4,5-dehydro-L-leucine, (R)-Boc-2-amino-3,3-dimethyl-pent-4-enoic acid, (R)-Fmoc-2-amino-3,3-dimethyl-pent-4-enoic acid, (S)-Boc-2-amino-3,3-dimethyl-pent-4-enoic acid, (S)-Fmoc-2-amino-3,3-dimethyl-pent-4-enoic acid, (R)-Boc-2-amino-3-ethyl-pentanoic acid, (R)-Fmoc-2-amino-3-ethyl-pentanoic acid, (S)-Boc-2-amino-3-ethyl-pentanoic acid, (S)-Fmoc-2-amino-3-ethyl-pentanoic acid, (R,S)-Boc-2-amino-tetradecanoic acid, (R,S)-Fmoc-2-amino-tetradecanoic acid, Fmoc-D-homo-Cha, Fmoc-L-homo-Cha, Fmoc-L-homoleucine, and Fmoc-D-homoleucine.

In some embodiments herein described, an α-helical peptide is provided by interposing during chemical synthesis an α,α'-dialkyl-amino acids every 3-4 residues in a linear polypeptide sequence. Peptide bond formation can be typically performed by a double coupling SPPS approach which refers to an additional peptide bond forming reaction (see Example 4).

For helix stabilization, simple N-protected α,α'-dialkyl amino acids spaced every 3-4 residues are preferred to minimize conformational interference abrogating α-helix formation; preferred side chains for α' are expected to be: methyl, —$CH_3$, ethyl —$CH_2CH_3$ and propyl, —$CH_2CH_2CH_3$; isobutyric and C1-C4 branched alkyl side chains.

In some embodiments, the at least one α,α'-dialkyl-amino acids in positions of the primary structure that facilitate helix formation (see "The Structure and Action of Proteins", R. E. Dickerson & I. Geis; W. A. Benjamin, New York; 1969; "Conformational effects of chiral alpha,alpha-dialkyl amino acids. I. C-terminal tetrapeptides of emerimicin containing alpha-ethylalanine." (1988).

Reference is made to the schematic illustration of FIG. 1, where the amino acids residues forming a secondary alpha helix are plotted on a helical wheel, a representation that illustrates the orientations of the constituent amino acids. Helical Wheel plots a peptide sequence as a helical wheel to help recognize amphiphilic and amphiphobic regions. Helical Wheel plots a helical wheel representation of a peptide sequence. Each residue is offset from the preceding one by 100 degrees, the typical angle of rotation for an alpha-helix. Thus, projecting a peptide in α-helical form onto a plane along the helix axis allows for the circular distribution of the amino acid side chain direction away from the center. Helices observed in proteins can range from four to over forty residues long, but a typical helix contains about ten amino acids (about three turns). Thus, an alpha helix can have multiple faces of similarly grouped polar and non-polar amino acids that can be targets for non-natural amino acids. In amphipathic alpha helices, the distribution of hydrophobic residues follows the loose rule that every 3rd and/or 4th residue is hydrophobic in nature. Computer programs useful to identify and classify amphipathic a helical domains include, but not limited to HELICALWHEEL[+], EMBOSS pepwheel, DrawCoil, heliQuest, and the like. Secondary-structure prediction methods useful to identify protein secondary structures, including alpha helices include but not limited to: EVA, Psipred, SAM, PORTER, PROF and SABLE (Mount DM (2004). Bioinformatics: Sequence and Genome Analysis (2ed.). Cold Spring Harbor, N.Y.: Cold Spring Harbor Laboratory Press. ISBN 0-87969-712-1. Martin K Jones, G. M. Anantharamaiah, and Jere P. Segrest; Journal of Lipid Research Volume 33, page 287-296, 1992).

In particular, referring to FIG. 1, an amphipathic alpha helix exhibits two faces or sides—one containing predominantly hydrophobic amino acids oriented toward the interior of the protein, in the hydrophobic core, and one containing predominantly polar amino acids oriented toward the solvent-exposed surface of the protein. In the secondary structure the hydrophobic amino acids and hydrophilic amino acids so positioned forms clusters on the helix as will be understood by a skilled person. Helices observed in proteins can range from four to over forty residues long, but a typical helix contains about ten amino acids (about three turns). Thus, an alpha helix has multiple faces of similarly grouped polar and non-polar amino acids that may be targets for non-natural amino acids which may provide unseen benefits in the apolipoprotein.

Referring to FIG. 1 the figure provides a schematic helical wheel representation of a 15 amino acid long alpha-helix. Projecting a peptide in alpha-helical form onto a plane along the helix axis allows for the circular distribution of the amino acid side chain direction away from the center. If the first amino acid is hydrophobic, and then amino acid at positions 4, 5, 8, 11, 12 and 15 are hydrophobic and the rest hydrophilic, the helix obtains an amphipathic character, with the upper half of the helix being hydrophobic and the lower half being hydrophilic. The distribution of hydrophobic residues is typically performed every 3rd and/or 4th residue is hydrophobic in nature. Referring to FIG. 1, at least one non-natural amino acid can have hydrophobic qualities and positioned in at least one or more positions of 1, 4, 5, 8, 9, 11, 12, and 15, and/or at least one amino acid can have hydrophilic qualities and positioned in at least one or more positions of 2, 3, 6, 7, 9, 10, 13, and 14. "Hydrophilic qualities" includes Polar/hydrophilic amino acids and their analogs of N, Q, S, T, K, R, H, D, E, and Y. Side chains which have various functional groups such as acids, amides, alcohols, and amines will impart a more polar character to the amino acid, hence encouraging water solubility. The ranking of polarity will depend on the relative ranking of polarity for various functional groups as determined in functional groups. In addition, the number of carbon-hydrogens in the alkane or aromatic portion of the side chain is considered along with the functional group. "Hydrophobic qualities" includes Non-polar/hydrophobic amino acids and their analogs G, A, V, L, I, P, Y, F, W, M, and C. "Hydrophobic qualities" includes non-polar side chains, such as but not limited to pure hydrocarbon alkyl groups (alkane branches), aromatic (benzene rings), and derivatives thereof. The number of alkyl groups also influences the polarity. The more alkyl groups present, the more non-polar the amino acid will be and hence, less soluble in water.

Referring to FIG. 1, a helical wheel representation can identify "sub-hydrophobic regions" or "sub-hydrophilic regions" which non-natural amino acids may be positioned having a desired relative hydrophobicity index. For example, amino acids number 1 (a) and number 4 (d) are within the hydrophobic face. Also, position of amino acid 1 and 4 are within a "sub-hydrophobic region" since they are positioned proximal to other hydrophobic amino acids. In contrast, amino acids position 11 is proximal to a hydrophobic amino acid 4 (d) and hydrophilic amino acid 7 (g). In one aspect, a sub-hydrophobic region includes amino acids at positions 1, 4, 5, 8, 11, and 15 and includes at least one non-natural amino acid having a relative hydrophobicity index of 100 to 64. In another aspect, the relative hydrophobicity index of that at least one non-natural amino acid(s) in the sub-hydrophobic region is higher than the amino acids within the hydrophobic not within the sub-hydrophobic region. In one aspect, a sub-hydrophilic region includes amino acids at positions 3, 6, 10, 13, and 14 having a relative hydrophobicity index of −14 to at least −55. In another aspect, the relative hydrophobicity index of that at least one non-natural amino acid in the sub-hydrophilic region is lower than at least one the amino acid(s) within the hydrophilic face not within the sub-hydrophilic region. In another aspect, an amino acid which borders a boundary between the hydrophobic and hydrophilic face (such as amino acid numbers 9 and 2) can be selected as non-natural amino acids having either hydrophilic or hydrophobic qualities, such as the relative hydrophobic index. The "hydrophobicity index" is a measure of the relative hydrophobicity, or how soluble an amino acid is in water at different pHs. For example, at pH 7, the relative hydrophobicity of Phe is 100, Ile is 99, and Glu −31, and Asp is −55. Thus, the higher the relative hydrophobicity index, the more hydrophobic the amino acids and conversely, the more negative the relative hydrophobicity index, the more hydrophilic the amino acid. At a pH of 7, very hydrophobic amino acids are in the range of 100 to 74, moderate hydrophobic amino acids are in the range 63 to 41, neutral amino acids are in the range 13 to −10, and hydrophilic amino acids are in the range of −14 to at least −55. Hydrophobicity scales, including relative hydrophobic index, can be determined through, but not limited to: Log P determination, Wimley-White whole residue hydrophobicity scales, Kyte-Doolittle Hydropathy Scale, as well as in silico computer modeling methods.

In some embodiments, at least one hydrophobic α,α'-dialkyl-amino acids can be positioned in the primary structure of the synthetic apolipoprotein possibly in combination with other hydrophobic amino acid with a periodicity $i_o+x_o$ where $i_o$ is a recurring position of an hydrophobic amino acid of plurality of hydrophobic amino acids in the primary structure and $x_o$ is a number of amino acids in the helical segment between a first occurrence and a second occurrence of the recurring position $i_o$ with wherein $x_o$ is 3 or 4. In particular in some embodiments, the placement of hydrophobic amino acids spaced with a linear periodicity of $i_o$ to $i_o+x_o$ can create a first side of hydrophobic amino acids and a second face of amino acids which are not hydrophobic in the alpha helix secondary structure of the synthetic apolipoprotein. For example, if i is the first position in the helical segment of 49 or more base pairs, than an $i_o+3$ periodicity can identify one or more residues for incorporation of a non-natural amino acid at positions 1, 4, 7, 10, 13, 16, 19, 22, 25, 28, 31, 34, 37, 40, 43, 46, and 49. In another aspect, if the periodicity is $i_o+4$ and i is the first position in the helical segment of 49 or more base pairs, than an i+4 periodicity can identify one or more residues for incorporation of a non-natural amino acid at positions: 1, 5, 9, 13, 17, 21, 25, 29, 33, 37, 41, 45, and 49. Note that the i+3 and the i+4 periodicities can identify placement of non-natural amino acids in any length of segment upstream or downstream the position i. In some embodiments, the hydrophobic amino acids within the helical segment can be comprised with a periodicity is not the same and therefore where $x_o$ can be any integer number from 3 to 9, preferably 3 and/or 4 and possibly up to 8 or 9 at the different turns within a same helical segment.

In some embodiments, at least one hydrophilic α,α'-dialkyl-amino acids can be positioned in the primary structure of the synthetic apolipoprotein possibly in combination with other natural hydrophilic amino acids with a periodicity $i_t+x_t$ where $i_t$ is a recurring position of an hydrophilic amino acid of the plurality of hydrophilic amino acids in the primary structure and $x_t$ is a number of amino acids in the helical segment between a first occurrence and a second occurrence of the recurring position $i_t$ and with $x_t$ being an integer from 3 to 9, preferably 3 or 4 and possibly up to 8 or 9. In embodiments wherein optimization of SPPS is desired, simple α,α'-dialkyl-amino acids are preferred, e.g., where the α' side chain is methyl, ethyl and propyl.

In some embodiments, at least one helical segment comprises hydrophobic non-natural amino acids together with hydrophilic amino acids. In some of those embodiments the $i_t+3$ or $i_t+4$ periodicity alternates with the $i_o+x_o$ position in the helical segment. For example, if $i_o$ is position 2 from the start of the helical segment $i_t+3$ or $i_t+4$ position can be positioned at position 5 or 6 from the start of the same helical segment. The positioning of $i_t$ and $i_0$ can cause a shift of a hydrophobic and hydrophilic sides in the secondary alpha helical structure of the segment.

In some embodiments, the α-helical segment can comprise additional substituted or unsubstituted non-natural amino acids, e.g., glycine derivatives, ring-substituted phenylalanine and tyrosine derivatives, N-methyl amino acids, e.g., N-methylvaline, 6-N-methyllysine, and the like. In certain embodiments one or more of the "natural" amino acids of the peptides described herein, can be substituted with the corresponding non-natural amino acid.

Substitution of natural and non-natural amino acids within the α-helical segment can affect the manner in which the amphipathic α-helices fold to form a bundle and three-dimensional structure of the bundle. Substitution of different amino acids within the α-helical segment can also affect the lipid binding properties. Computer programs to identify and classify amphipathic helical domains are known to those of skill in the art and many have been described by Jones et al. (1992) J. Lipid Res. 33: 287-296). Such programs include, but are not limited to the helical wheel program (WHEEL or WHEEL/SNORKEL), helical net program (HELNET, HELNET/SNORKEL, HELNET/Angle), program for addition of helical wheels (COMBO or COMBO/SNORKEL), program for addition of helical nets (COMNET, COMNET/SNORKEL, COMBO/SELECT, COMBO/NET), consensus wheel program (CONSENSUS, CONSENSUS/SNORKEL), and the like In some embodiments, synthetic apolipoprotein herein described comprise peptide helices having a length of 6, 7, 10, 11, 13, 14, 17, 18, 21, 22, 24, 25, 28, 29 or 31 amino acid residues In some embodiments, alpha helical segments comprise helices with non-polar side-chains starting 1 to 3 position upstream from the C-terminal position coinciding with the beginning of the alpha helical secondary structure.

In some embodiments, the number of alpha-helical peptide segments that form an apolipoprotein range from three to twelve alpha-helical segments. In some embodiments, the number of alpha-helical peptide segments range from four to eight alpha-helical segments. In some embodiments, the number of α-helical peptide segments that form the apolipoprotein is at least four α-helical peptide segments. In some embodiments, each α-helical peptide segment comprises from 15 to 100 amino acids. In another embodiment, each α-helical peptide segment comprises 20 to 50 amino acids.

In embodiments herein described, synthetic apolipoproteins can comprise a plurality of amphipathic α-helical peptide segments covalently linked together using well-known and established fragment conjugation or ligation chemistries described by Dawson and Kent in their comprehensive review—"Synthesis of Native Proteins by Chemical Ligation" 2000, Ann Rev Biochem 69:923-60.

In some embodiments ligation of the helices and the linker segments can be performed—as described in "Synthesis of Native Proteins by Chemical Ligation" 2000, Ann Rev Biochem 69:923-60.

Typically, α-helical peptides are separated by a short "linker sequence" which can be provided by a sequence of natural or non-natural amino acids. The linker sequence can form an amino acid loop. However, "linker sequences" may or may not be present between adjacent alpha-helical peptides. In this embodiment, the C-terminus of a first α-helix is directly adjoined to the N-terminus of the subsequent, second alpha-helix. Linker sequences may comprise as few as one amino acid to over 30 amino acids. More preferably, the linker sequence comprises 1 to 15 amino acids, even more preferably 1 to 10 L-amino acids.

In some embodiments, inter-helical linkers can be provided by peptides of 3-6 glycine residues or other residues. The most commonly used is glycine or other amino acids, e.g. 3-amino glycine (beta glycine). In some embodiments, the linkers between helical segments can also comprise non-natural amino acids.

In some embodiments, at least one α-helical peptide segment is derived from a different apolipoprotein to form a chimeric apolipoprotein.

In embodiments herein described the helical segment of a synthetic apolipoprotein are expected to interact with the lipids to form a supersecondary unit that combines with the lipids and forms a tertiary structure that will favor formation of an NLP.

A "supersecondary unit" or "structural motif" indicates a segment of the protein that forms an identifiable three-dimensional structure formed by adjacent secondary structure elements optionally linked by unstructured protein regions. In structural motifs the secondary structures are typically comprised with a same orientation one with respect to another. In particular some structural motifs (e.g., four-helix bundle) are conserved in different proteins as will be understood by a skilled person.

The "tertiary structure" of a protein refers to the three-dimensional structure of a protein, stabilized by non-covalent interactions among non-adjacent segments of the protein and optionally by one or more additional compounds or ions interacting through covalent or non-covalent interactions with one or more segments of the proteins. Exemplary non-covalent interactions stabilizing the three dimensional structure of the proteins comprise non-specific hydrophobic interactions, burial of hydrophobic residues from water, specific tertiary interactions, such as salt bridges, hydrogen bonds, the tight packing of side chains, chelation and disulfide bonds and additional interactions identifiable by a skilled person. Exemplary covalent interactions among compounds or ions and segments of the protein comprise N-linked glycosylation, cytochrome C haem attachment and additional interaction identifiable by a skilled person. In some instances, multiple proteins can form a protein complex, also called a multimer, with one or more identifiable three dimensional structures stabilized by non-transitory interactions between the multiple proteins. The three-dimensional structure of the protein complex is also called "quaternary structure" of the complex. Accordingly, the quaternary structure can be stabilized by some of the same types of non-covalent and covalent interactions as the tertiary structure as will be understood by a skilled person. Multimers made up of identical subunits are referred to with a prefix of "homo-" (e.g. a homotetramer) and those made up of different subunits are referred to with a prefix of "hetero-", for example, a heterotetramer, such as the two alpha and two beta chains of hemoglobin. "Non-transitory interactions" as used herein indicates interactions between proteins or related segments that are detectable by laboratory techniques such as immunoprecipitation, crosslinking and Forster Resonance Energy Transfer (FRET) measurements, crystallography, Nuclear Magnetic Resonance (NMR) and additional techniques identifiable by a skilled person.

Some embodiments herein described, involve interaction of apolipoproteins and phospholipids results in formation of lipoprotein particles with nanometer-sized particles, referred as nanolipoprotein particles or NLPs. The term "nanolipoprotein particle" 'nanodisc" "rHDL" or "NLP" as used herein indicates a supramolecular complex formed by a membrane forming lipid and a scaffold protein, that following assembly in presence of a target protein also include the target protein. The scaffold protein and target protein constitute protein components of the NLP. The membrane forming lipid constitutes a lipid component of the NLP. The term "membrane forming lipid" or "amphipathic lipid" as used herein indicates a lipid possessing both hydrophilic and hydrophobic properties that in an aqueous environment assemble in a lipid bilayer structure that consists of two opposing layers of amphipathic molecules know as polar lipids. Each polar lipid has a hydrophilic moiety, i.e. a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols, alkylphosphocholines and the like. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). In a preferred embodiment, the lipid is dimyristoylphosphatidylcholine (DMPC).

The term "scaffold protein" as used herein indicates any amphipathic protein that is capable of self-assembly with an amphipathic lipid in an aqueous environment, organizing the amphipathic lipid into a bilayer, and include but are not limited to apolipoproteins, lipophorins, derivatives thereof (such as truncated and tandemly arrayed sequences) and fragments thereof (e.g. peptides), such as apolipoprotein E4, 22K fragment, lipophorin III, apolipoprotein A-1 and the like. In particular, in some embodiments rationally designed amphipathic peptides and synthetic apolipoproteins can serve as a scaffold protein of the NLP.

Predominately discoidal in shape, nanolipoprotein particles typically have diameters between 10 to 20 nm, share uniform heights between 4.5 to 5 nm and can be produced in yields ranging between 30 to 90%. The particular lipoprotein, the lipid to lipoprotein ratio, and the assembly parameters determine the size and homogeneity of nanolipoprotein particles.

In some embodiments herein described the scaffold protein is provided by total chemical synthesis yielding a synthetic apolipoprotein, the latter is capable encircling a nanometer scale lipid bilayer creating a nanolipoprotein particle (NLP). In some embodiments, the synthetic apolipoprotein can be customized by varying the length of the amphipathic helical part of the protein. Each apolipoprotein used for membrane sequestering can have an optimized protein to lipid ratio in order to ensure self-assembly of the nanolipoprotein particles (NLPs).

In some embodiments, the length of the synthetic apolipoprotein herein described is selected to customize the average size of the particles from 5 to 70 nm (+/−20%) and a height from 3 to 15 nm (+/−20%). In a preferred embodiment, the size of the NLP particles range from 5 to 10 nm (+/−3%) and a height in the range of 4.5 to 6 nm (+/−3%). (Peters-Libeu, C. A., Newhouse, Y., Hatters, D. M., and Weisgraber, K. H. (2006) Model of biologically active apolipoprotein E bound to dipalmitoylphosphatidylcholine *J Biol Chem* 281, 1073-9. 29. Whorton, M. R., Bokoch, M. P., Rasmussen, S. G., Huang, B., Zare, R. N., Kobilka, B., and Sunahara, R. K. (2007); A monomeric G protein-coupled receptor isolated in a high-density lipoprotein particle efficiently activates its G protein *Proc Natl Acad Sci USA* 104, 7682-7. Tufteland, M., Pesavento, J. B., Bermingham, R. L., Hoeprich, P. D., Jr., and Ryan, R. O. (2007); Peptide stabilized amphotericin B nanodisks *Pepides* 28, 741-6. Cruz, F., and Edmondson, D. E. (2007) Kinetic properties of recombinant MAO-A on incorporation into phospholipid nanodisks *J Neural Transm* 114, 699-702.

In some embodiments, the number of α-helices in a synthetic apolipoprotein forming a scaffold protein around the lipids can be in the range of 1 to 10. In another aspect, the total number of a helices forming a belt around the lipids is in the rage of 3 to 10. In some embodiments, the number of α-helices in the synthetic apolipoprotein can be in the range of 4 to 10. In general, increasing the total number of helices can increase the discoidal size of particle through having a larger circumference.

In particular, in some embodiments the NLP components can be contacted to form an admixture that is then preferably subjected to a temperature transition cycle in presence of a detergent. In the temperature cycle, the temperature of the admixture is raised above and below the gel crystalline transition temperature of the membrane forming lipids. Exemplary procedures are illustrated in Example 5 of the present application. A further description of this method can also be found in the U.S. patent application entitled "Nanolipoprotein Particles and Related Methods and Systems for Protein Capture Solubilization and/or Purification" Ser. No. 12/352,548 filed on Jan. 12, 2009 and incorporated herein by reference in its entirety.

In some embodiments, the nanolipoprotein particles formed with the synthetic apolipoprotein herein described can further comprise one or more membrane proteins. The term "membrane protein" as used herein indicates any protein having a structure that is suitable for attachment to or association with a biological membrane or biomembrane (i.e. an enclosing or separating amphipathic layer that acts as a barrier within or around a cell). In particular, membrane proteins include proteins that contain large regions or structural domains that are hydrophobic (the regions that are embedded in or bound to the membrane); those proteins can be difficult to work with in aqueous systems, since when removed from their normal lipid bilayer environment those proteins tend to aggregate and become insoluble.

Exemplary methods to provide nanolipoprotein particles which are expected to be applicable to provide one or more NLPs presenting one or membrane proteins, comprise the methods described in U.S. Patent Publication No. 2009/0192299 related to methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystallization transition temperature of the membrane forming lipid of the nanolipoprotein particle. In some embodiments, verification of inclusion of amembrane proteins can be performed using the methods and systems for monitoring production of a target protein in a nanolipoprotein particle described in U.S. Patent Publication No. 2009/0136937 filed on May 9, 2008 with Ser. No. 12/118,530 which is incorporated by reference in its entirety.

An example of a detergent commonly used to prepared apolipoprotein-lipid complexes is sodium cholate. Preferred lipids are phospholipids, most preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoyl-phosphatidylethanolamine, distearoyl-phosphatidylethanolamine, di-myrstoyl-phosphatidylserine, and dioleyl-phosphatidylcholine. Non-phosphorus containing lipids may also be used, including stearylamine, docecylamine, acetyl palmitate, and fatty acid amides. Additional lipids suitable for use are well known to persons of skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference.

In some embodiments, the methods and systems herein described are performed at predefined lipid protein ratio, assembly conditions and/or with the use of preselected protein component and amphipathic lipid so to increase the yield, control the size of the resulting NLP and/or provide an NLP of pre-determined dimensions so to include a predetermined target protein. In one aspect, the molar ratio of lipid to apolipoprotein is 6:1, 5:1, 4:1, 3:1, 2:1, 1:1, 1:6, 1:5, 1:4, 1:3, and 1:2. However, the lipid to protein ratio can be determined on a case by case basis in view of the experimental design.

In another embodiment, the phospholipid can be functionalized or replaced. The use of functionalized phospholipids enables attachment various peptides or other biologics to the surfaces of the lipid of the NPL that allows some desired target features to be obtained, such as stability, affinity for a target molecule, and the like. A "functional group" is a group of atoms of a particular arrangement that gives the entire molecule certain characteristics. Non-limiting examples of functional groups include: chelated Ni atoms, azide, anhydride, halogens, carboxy, amino, hydroxyl, and phosphate groups, and the like. Each functional group has an electronic effect, a solubility effect, and a steric effect that needs to be considered when evaluating the overall effect on the apolipoprotein and NLP formation. First of all, the addition of a single functional group to a lipid will affect the overall electronics, solubility, and steric dimensions of that molecule. The electronic effect of a functional group is measured by its ability to either donate its electrons to adjacent atoms or functional groups or to pull or withdraw electrons away from adjacent atoms or functional groups. There are two main components that comprise the overall electronic effect of a functional group, its ability to participate in resonance and its intrinsic inductive effects. The two major properties that contribute to the water solubility of a functional group are its ability to ionize and/or its ability to form hydrogen bonds. Acidic and basic functional groups are capable of ionization and can become negatively or positively charged, respectively. Functional groups that enhance the lipid solubility are referred to as hydrophobic or lipophilic functional groups. Functional groups that lack the ability to either ionize or form hydrogen bonds tend to impart a measure of lipid solubility to a drug molecule. The functional group can be attached to the lipid polar head through covalent or ionic bonds and "weak bonds" such as dipole-dipole interactions, the London dispersion force and hydrogen bonding, preferably covalent. Moreover, functionalization of the lipid may involve hydrophobic quantum dots embedded into the lipid bilayer. The following article is incorporated by reference in its entirety: R. A. Sperling, and W. J. Parak. "Surface modification, functionalization and bioconjugation of colloidal inorganic nanoparticles". Phil. Trans. R. Soc. A 28 Mar. 2010 vol. 368 no. 1915 1333-1383.

Taken together, the production of the synthetic apolipoprotein constructs herein described that comprise at least one hydrophobic $\alpha,\alpha'$-dialkyl-amino acids allows assembly of various types of NLPs as will be understood by a skilled person.

In some embodiments, the synthetic apolipoproteins, synthetic amino acid or NLPs herein described can be provided as a part of systems in accordance to various embodiments herein described.

In some embodiments, the systems herein described can be provided in the form of kits of parts. In a kit of parts, synthetic apolipoproteins, synthetic aminoacid or NLPs can be provided in various combinations one with another and with, one or more membrane forming lipids, one or more membrane protein, and/or scaffold proteins or fragments thereof. In the kits of parts the components can be comprised in the kit independently possibly included in a composition together with suitable vehicle carrier or auxiliary agents.

Additional components can also be included and comprise microfluidic chip, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (i.e. wash buffers and the like).

Nanolipoprotein particles formed with synthetic NLPs herein described and related methods and systems herein described can be used in connection with various applications wherein control of the NLP size is desired, for example to accommodate and facilitate isolation of functional biosynthetic enzyme complexes ranging from biopolymer synthesis [e.g., polysaccharides (cellulose), polyesters, polyamides, polyisoprenes and additional enzymes identifiable by a skilled person] to photon capture [PS II]. such as the embodiments described in U.S. Pat. No. 9,303,273, the content of which is incorporated by reference in its entirety.

Further details concerning the identification of the suitable carrier agent or auxiliary agent of the compositions, and generally manufacturing and packaging of the kit, can be identified by the person skilled in the art upon reading of the present disclosure.

EXAMPLES

The following examples illustrate various embodiments. Those skilled in the art will recognize many variations that are within the spirit of the various embodiments and scope of the claims. The methods and system herein disclosed are further illustrated in the following examples, which are provided by way of illustration and are not intended to be limiting.

Example 1: Exemplary Synthetic Apolinoprotein Structure and Configuration

Figure 2:
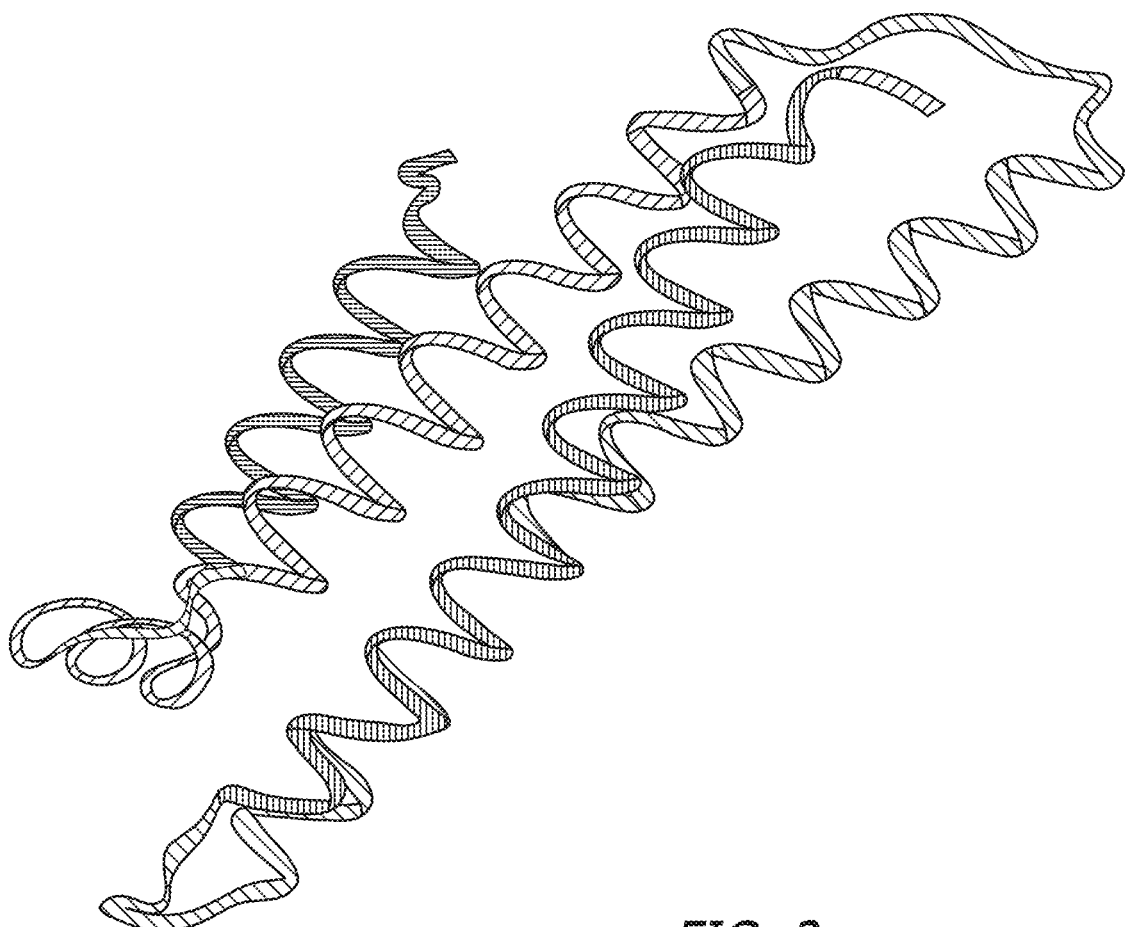
FIG. 2 provides a cartoon representation of helical bundles of Apolipoprotein E4, 22 k fragment structure derived from the published protein crystal structure. The four different helical segments are shown in different markings.

Exemplary synthetic apolipoprotein herein described herein have can have a typical structure formed by helical segments linked together by linkers schematically shown in the illustration of FIGS. 2 and 3 which provides a representation of the exemplary apolipoprotein E4, 22K fragment.

In particular, the illustration of FIG. 2 shows helical segments of Apolipoprotein E4, 22K fragment structure. As shown in FIG. 2, there are four helices, which can have varying length and chemical characteristics.

The sequences of each of the helical fragments of naturally occurring apolipoprotein E4, 22K fragment are shown in the illustration of FIG. 3 and also reported in Table 1A below.

Example 2: Exemplary Synthetic Apolipoprotein—Designed Sequence

A sequence of an apolipoprotein can be designed to in view of the desired interactions between the α-helices and the lipids of the nanolipoprotein particles and the structure of the α-helices that is desired Predicting α-helical structures can be made through a helical wheel visual representation. A helical wheel is a type of plot or visual representation used to illustrate the properties of alpha helices in proteins. The sequence of amino acids that make up a helical region of the protein's secondary structure are plotted in a rotating manner where the angle of rotation between consecutive amino acids is 100°, so that the final representation looks down the helical axis. The plot reveals whether hydrophobic amino acids are concentrated on one side of the helix, usually with polar or hydrophilic amino acids on the other.

Referring to FIGS. 5-8, helical wheel representations are shown for Helixes 1-4 for the apolipoprotein E4 fragment.

TABLE 1A

| Apolipoprotein | Residues | Amino acid sequence | SEQ ID NO |
|---|---|---|---|
| Apolipoprotein E4, Helix 1 | 24-52 | QRWELALGRFWDYLRWVQTLSEQVQEELL | 1 |
| Apolipoprotein E4, Helix 2 | 54-82 | SQVMELRALAIDETMKELKAYKSELEEQL | 2 |
| Apolipoprotein E4, Helix 3 | 86-126 | AEETRARLSKELQAAQARLGADMEDVRGRLVQYRGEVQAMLG | 3 |
| Apolipoprotein E4, Helix 4 | 129-165 | STEELRVRLASHLRKLRKRLLRDADDLQKRLAVYQAG | 4 |

In synthetic apolipoprotein herein described, one or more of the amino acids of at least one segment can be replaced by an α,α'-dialkyl amino acids. Table 1B shows an exemplary modification of the apolipoprotein E4 helices that is modified to include α,α'-dialkyl amino acids and is expected to have an increased stability and/or amphipathicity with respect to the apolipoprotein E4.

Example 3: Synthetic Apolipoprotein and Related Designed Sequence

An additional example of synthetic apolipoprotein is shown in Table 2 wherein the C-terminal portion of a lipophorin protein from *B. mori*. The proteins form NLPs readily and in high yield, the projected helical region at the

TABLE 1B

| Apolipoprotein | Residues | Amino acid sequence | SEQ ID NO |
|---|---|---|---|
| Modified Apolipoprotein E4, Helix 1 synthetic | 24-52 | QRWELAibGRFWAibYLRWAibQTLSAibQVQAibELL | 5 |
| Modified Apolipoprotein E4, Helix 2 | 54-82 | SQAibTQELRAibLMDEAibMKELKAibYKSEAibEEQL | 6 |
| Modified Apolipoprotein E4, Helix 3 | 86-126 | ALETRAibRLSKELQAibAQARLGAibDMEDAibRGRLVQYRAibEVQAMLG | 7 |
| Modified Apolipoprotein E4, Helix 4 | 129-165 | STEEAibRVRLAibSHLRKLRKRLLRDAibDDLQKRLAibVYQAG | 8 |

C-terminus is expected to be modifiable to include helix forming Aib residues as indicated; the periodicity is every 6-9 residues.

TABLE 2

C-terminal region of lipophorin protein-B. mori

| | | SEQ ID NO |
|---|---|---|
| Naturally occurring | KVSSNVQETNEKLAPKIKAAYDDFAKNTQE VIKKIQEAANAKQ | 9 |
| Synthetic | KVSSNVQETNAibKLAPKKIKAAibYDDFAK NTQAibVIKKIQEAibANAKQ | 10 |

Example 4: Chemical Synthesis of a Synthetic Apolipoprotein

It is possible to synthesize each helical segment using SPPS and then ligate them together to create an entire 4-helix bundle protein. Ligation chemistry will be that described by Dawson and Kent "Synthesis of Native Proteins by Chemical Ligation" 2000, Ann Rev Biochem 69:923-60, and outlined below with reference to FIG. 4.

In particular, each helical segment will be synthesized using automated Solid Phase Peptide Synthesis (SPPS), ABI 433A peptide synthesizer. Appropriate starting resins will be purchased and Fmoc-protected amino acids will be added sequentially in an automated manner in accordance with the sequence specified in the target peptide. Amide bond formation is accomplished using uronium-based coupling chemistry as implemented by ABI instrumentation.

This coupling chemistry can be applied to appropriately protect non-natural amino acids, e.g. amino isobutryic acid (AIB) for helix enhancement and stabilization. Additionally, modified amino acids containing fluorophores or $^{14}C$ labels can be included in an overall peptide synthesis regimen. Ligation of helical segments involves the native chemical ligation method as described by Dawson and Kent B "Synthesis of Native Proteins by Chemical Ligation" 2000, Ann Rev Biochem 69:923-60.

Figure 4:
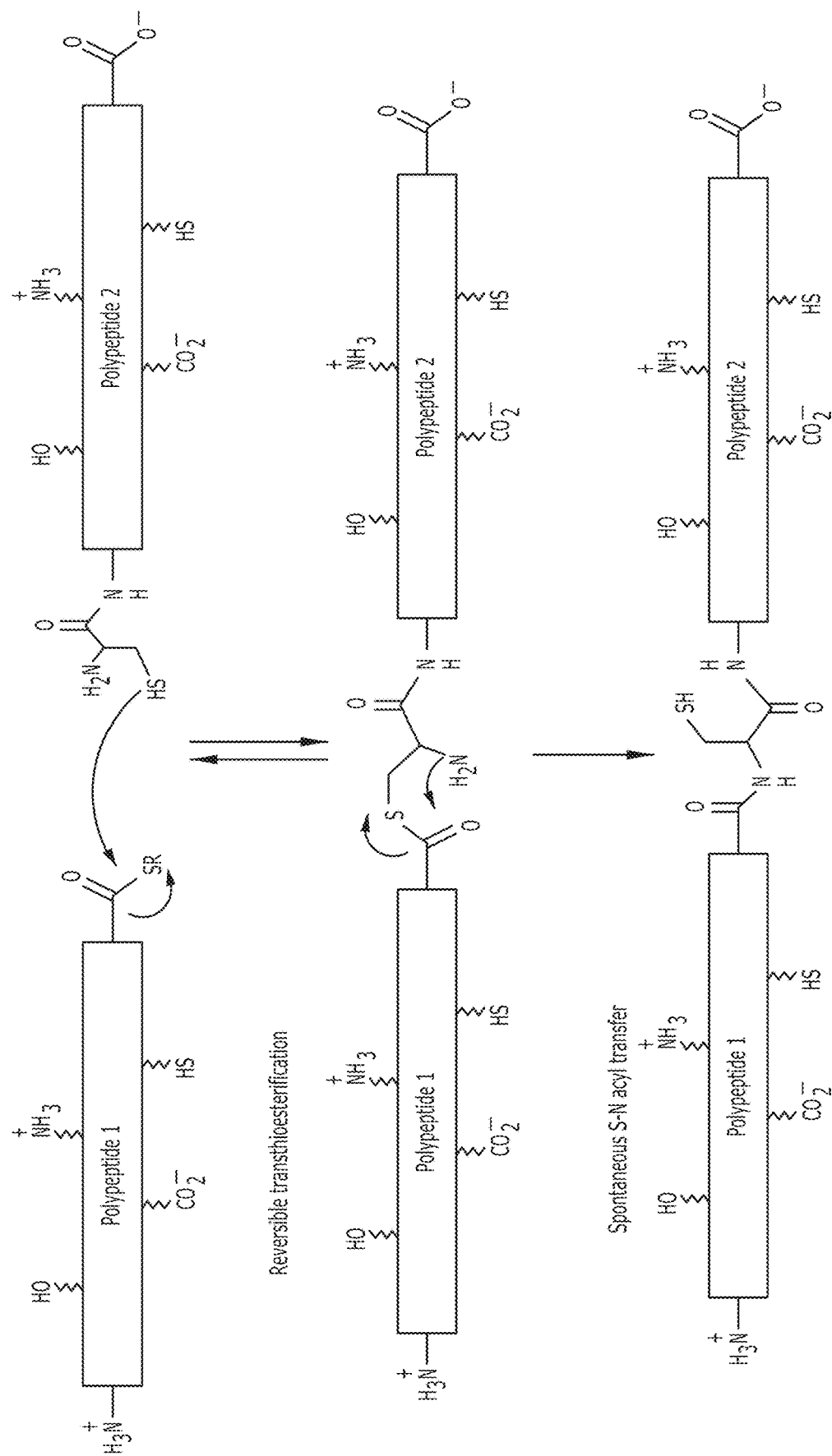
FIG. 4 provides a schematic illustration of a chemical ligation method to ligate helical segments together to create a helical bundle protein.
Figure 5:
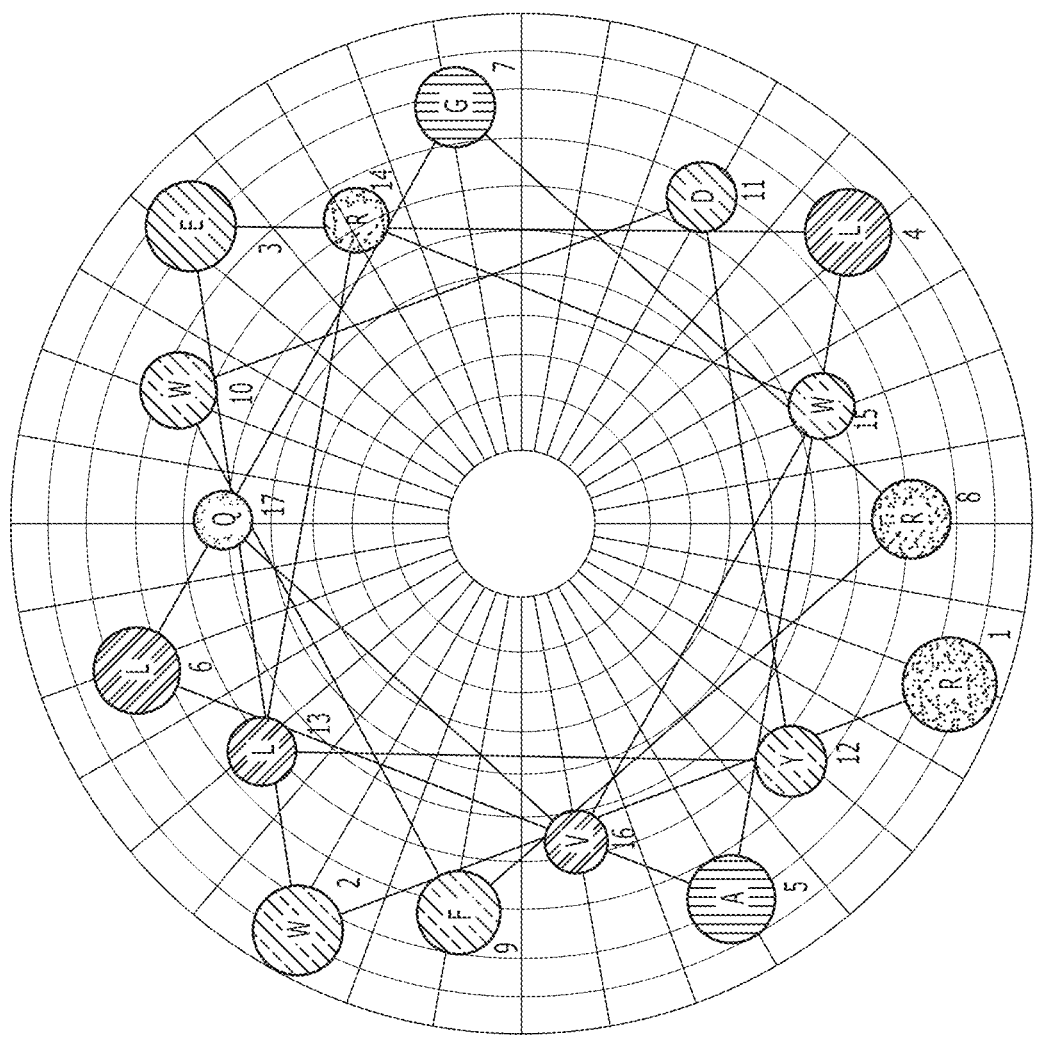
FIG. 5 provides a helical wheel representation of Helix #1, residues 24-52, of Apolipoprotein E4, 22 k fragment. Amino acids with a similar degree of hydrophobicity and side chain dimensions are indicated with a same marking.
Figure 6:
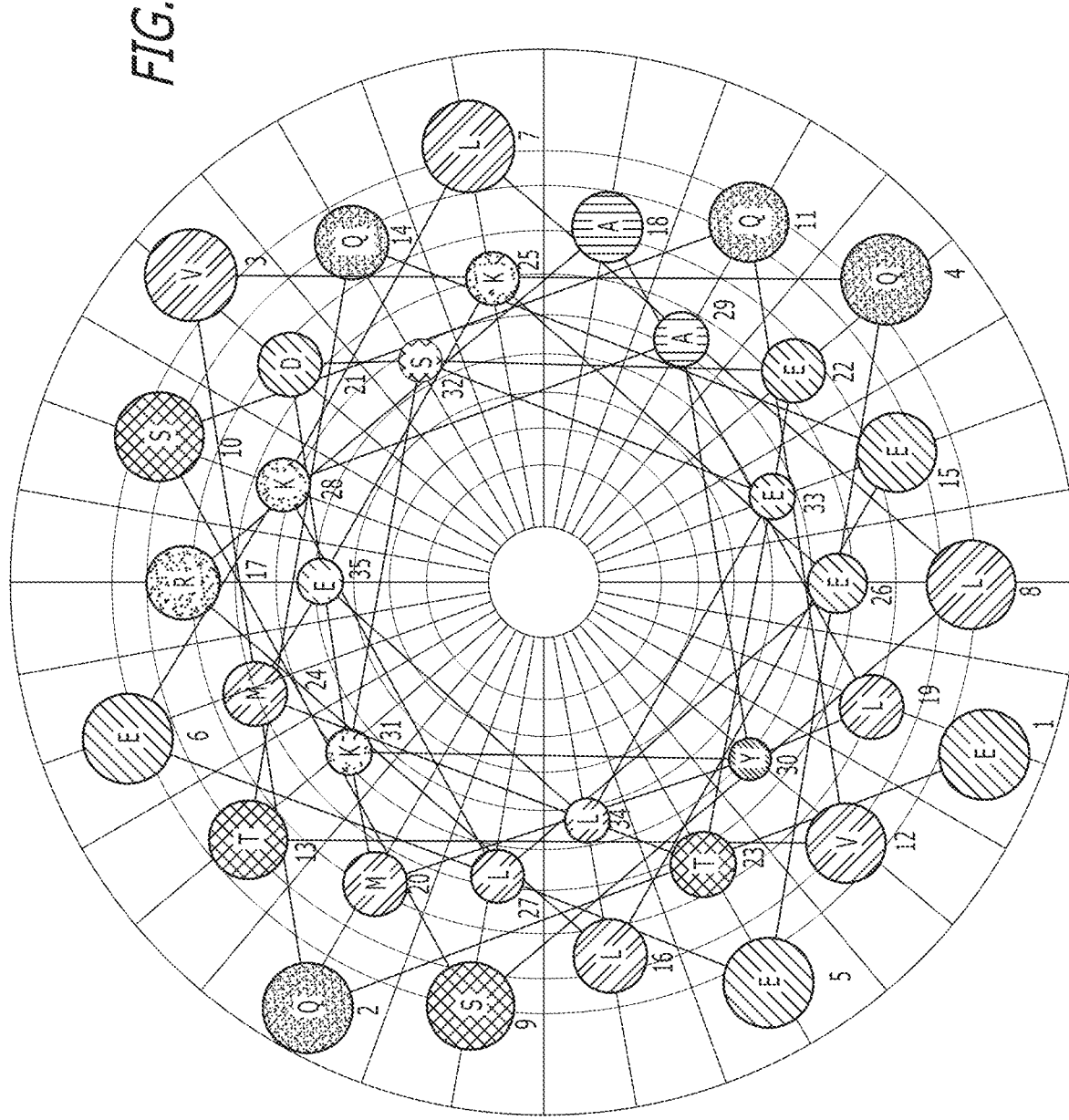
FIG. 6 provides a helical wheel representation of Helix #2, residues 54-82, of Apolipoprotein E4, 22 k fragment. Amino acids with a similar degree of hydrophobicity and side chain dimensions are indicated with a same marking.
Figure 7:
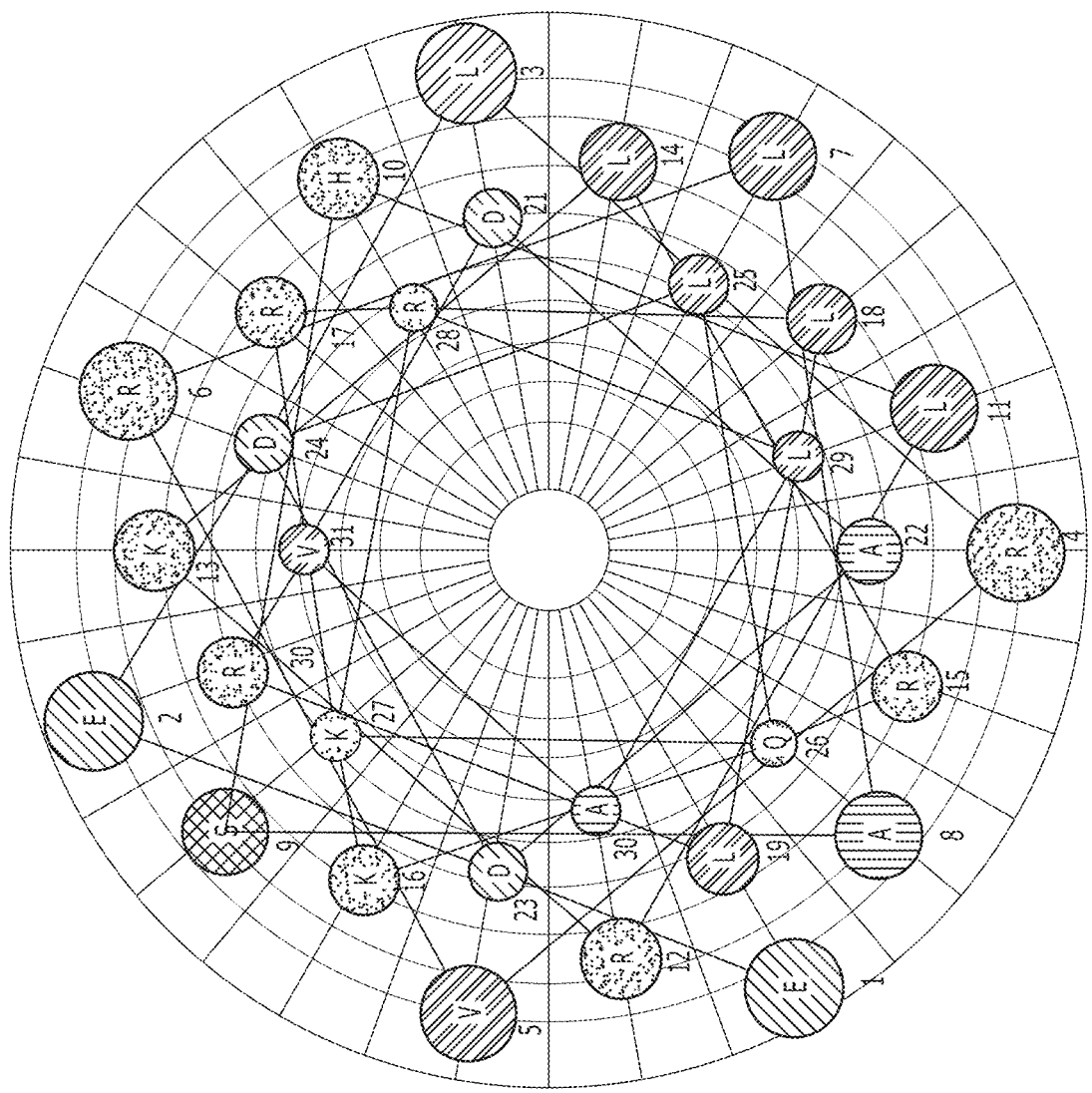
FIG. 7 provides a helical wheel representation of Helix #3, residues 86-126, of Apolipoprotein E4, 22 k fragment. Amino acids with a similar degree of hydrophobicity and side chain dimensions are indicated with a same marking.
Figure 8:
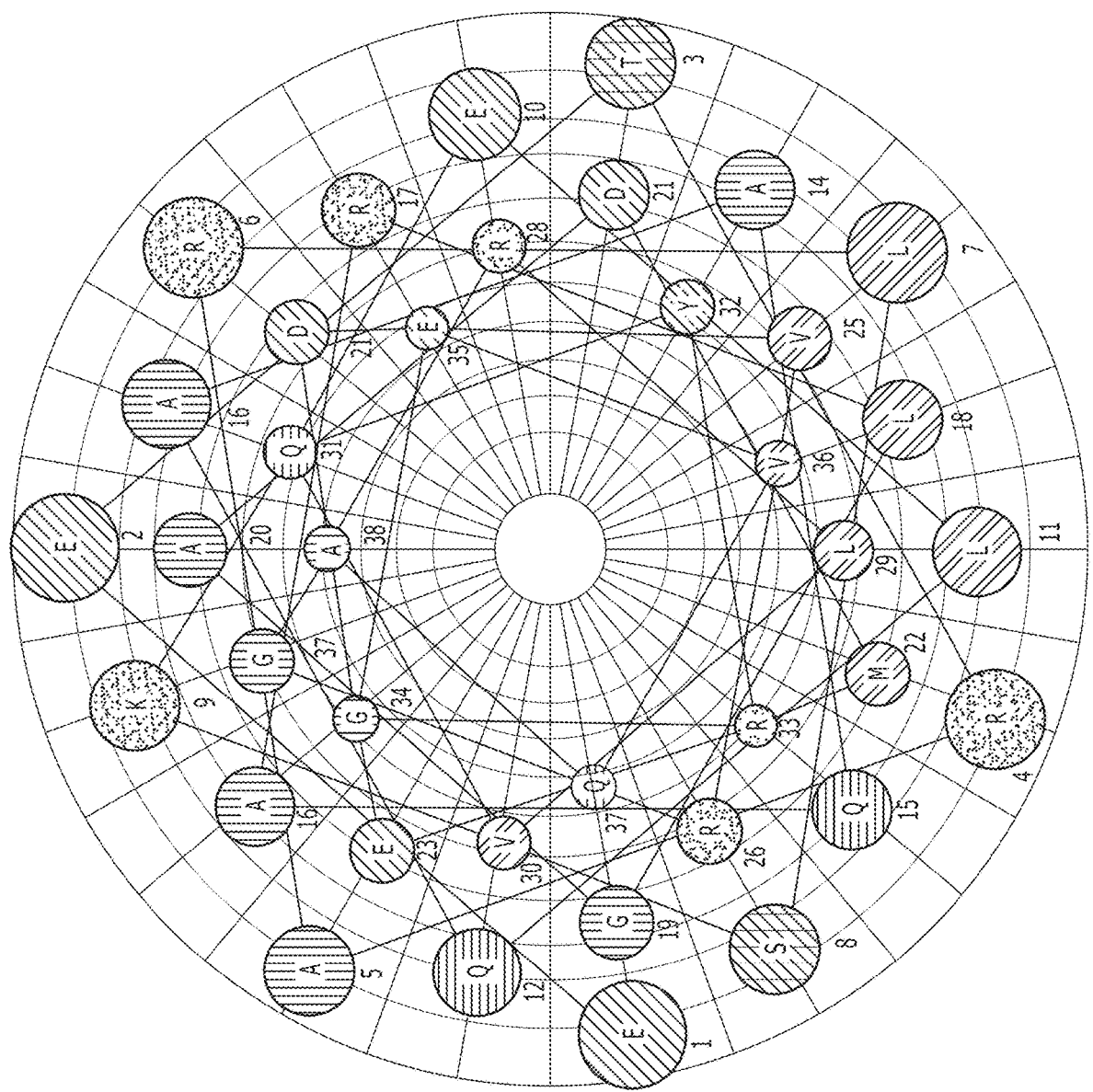
FIG. 8 provides a helical wheel representation of Helix #4, residues 129-165, of Apolipoprotein E4, 22 k fragment. Amino acids with a similar degree of hydrophobicity and side chain dimensions are indicated with a same marking.

In particular, referring to FIG. 4, C-terminal thioester reacts with an N-terminal cysteine thiol group to form a transient thioester, the latter immediately collapses to regenerate cys-thiol and an amide bond joining two polypeptides.

In particular SPPS can be carried out with fresh coupling reagents e.g. 1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin-1-yl-methylene]-N-methylmethanaminium hexafluorophosphate N-oxide (HATU) and hydroxybenzotriazole (HOBT) and protected amino acid. Reaction time for each HATU/HOBT coupling is extended to a few hours and repeated 1× or 2× with fresh reagent(s) vs. the normal 20-30 minute coupling time

Example 5: Nanolipoprotein Particles

Figure 9:
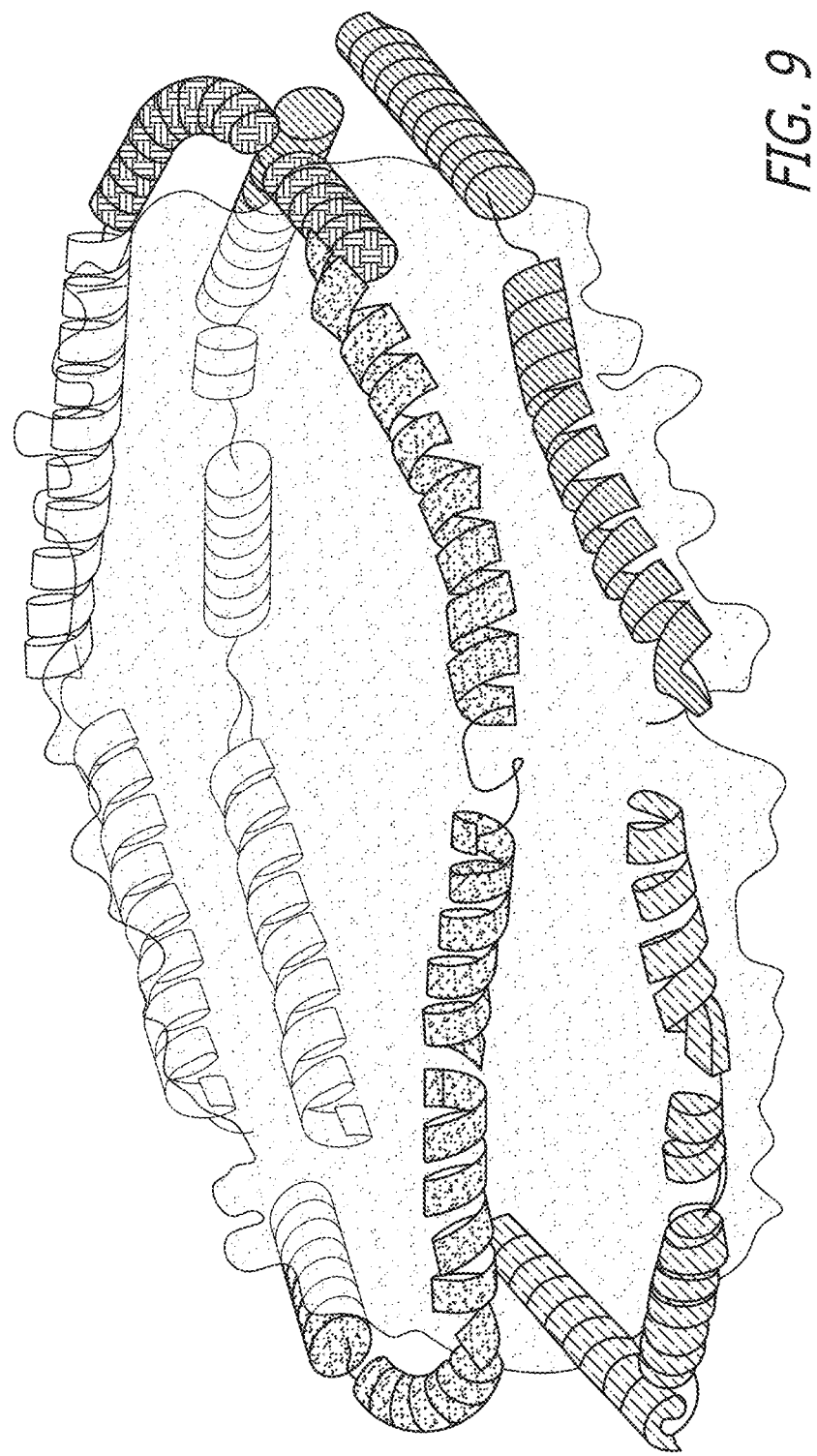
FIG. 9 provides a cartoon representation of a nanolipoprotein particle (NLP) showing helical strands/segments of apolipoprotein with different segments shown with different markings, surrounding a population of phospholipids shown as a dotted area.

Exemplary nanolipoprotein particles including a synthetic apolipoprotein herein described can be made from purified, naturally occurring and/or recombinant apolipoproteins and lipids. A schematic illustration of the nanolipoprotein particle or NLP showing helical strands of apolipoprotein surrounding a population of phospholipids is shown in FIG. 9.

Exemplary procedures that are expected to be applicable to NLPs comprising a synthetic apolipoprotein herein described and in particular to the synthetic apolipoprotein of Examples 1 to 3.

Apolipoproteins and amphipathic lipids when mixed in aqueous solutions spontaneously assemble into nano-sized discoidal particles ranging in diameter from 8 to 50 nm. When the assembly process occurs in the presence of a detergent solubilized membrane protein (MP), the latter is incorporated into the NLP and retains its biological function.

When the NLP assembly process occurs in the presence of a small molecule therapeutic agent like a lipophilic drug molecule, e.g. amphotericin B, with the drug preferentially contained within the NLP. Other targets can be included as well as would be understood by a skilled person.

Typically, 1 ug apolipoprotein with 4 ug lipid in 300-500 ul in TBS, pH=7.4, 20 mM cholate, dialyze preparation overnight can spontaneously form NLPs. Cholate is dialyzed away. In the presence of tetraether lipids, a TBS buffer is preferred.

Reaction of each protein with DMPC yields NLPs with unique overall structural/shape characteristics. In general, particles produced are expected to be found to be discoidal in shape with diameters ranging from 10 to 20 nm dependent on the apolipoprotein or derivative used in assembly; a height of ~5 nm can be determined for all NLP preparations, consistent with a membrane bilayer formed by DMPC. The apolipoprotein is the primary determinant of NLP size. Moreover, measured sizes and shapes did not differ appreciably when formed in the presence of cholate and when using fluorophore labeled reactants.

Lipid Preparation—

Small unilamellar vesicles of DMPC (liposomes) can be prepared by probe sonicating a 68 mg/mL aqueous solution of DMPC until optical clarity is achieved; typically 15 min on ice is sufficient. A 2 min. centrifugation step at 13700 RCF can be used to remove any metal contamination from the probe tip.

Conventional Assembly of "Empty"—NLPs and Integral Membrane Protein-NLPs—

For "empty"-NLPs ApoE4 can be combined with DMPC liposomes in a ratio of 1:4 by mass in TBS buffer. The mixture can be then incubated at room temp. for 2 hours. The NLPs can be then purified by size exclusion chromatography.

Assembly of integral membrane protein, for example, bR-NLPs: apoE4 can be mixed with DMPC in a ratio of 1:4 by mass in TBS buffer. Sodium cholate solution can be then added to a final concentration of 20 mM. Purple membrane bacteriorhodopsin can be then added in a 0.67 mass ratio to the ApoE4 apolipoprotein. Incubation is expected to proceed as described above, followed by dialysis in TBS for detergent removal. The NLPs can be then purified by size exclusion chromatography.

Nanolipoprotein Particle (NLP) Formation and Purification—

Nanolipoprotein particles (NLPs) form in a self-assembling process in the correct mass ratio of apolipoprotein to lipid. This ratio can be be optimized for each different apolipoprotein. The ratio described below is for ApoE422k. Other ratios can be found in the literature (17, 24, 25). Start water bath incubators. Temperatures at 30° C. and 20° C. Probe sonicate 34 mg of DMPC into 1 mL of TBS at 6 amps for approximately 15 minutes or until optical clarity is achieved. Centrifuge DMPC solution at 13700 RCF for 2.5 min to remove residual metal from probe sonicator. Transfer supernatant into new tube. Combine Apo E422K with DMPC in a ratio of 1:4 by mass in TBS buffer in a 1.5 mL Eppendorf tube. Typically batches are of the 250 µL size. Transition temperature procedure: Immerse tube in water bath for 10 minutes each 30° C. (above DMPC transition temp.) followed by 20° C. (below DMPC transition temp.). Repeat the procedure three times then incubate at 23.8° C. overnight. Filter preparation through a 0.45 µm spin filter at 13700 RCF for 1 min. Purify NLPs using size exclusion chromatography. Use a Shimadzu SCL-10A FPLC, equipped with a Superdex 200 10/300 GL column with TBS buffer, a 200 µL sample injection volume, and a flow rate of 0.5 mL/min. Collect 0.5 mL fractions. Concentrate fractions using a Vivaspin 2 ultrafiltration device with a 50 k MWCO. The following articles are incorporated by reference in their entireties: Chromy, B. A., et al. (2007) Different Apolipoproteins Impact Nanolipoprotein Particle Formation *J. Am Chem Soc*; Bayburt, T. H., Carlson, J. W., and Sligar, S. G. (1998) Reconstitution and imaging of a membrane protein in a nanometer-size phospholipid bilayer *J Struct Biol* 123, 37-44; Gursky, O., Ranjana, and Gantz, D. L. (2002) Complex of human apolipoprotein C-1 with phospholipid: thermodynamic or kinetic stability? *Biochemistry* 41, 7373-84. Jayaraman, S., Gantz, D., and Gursky, O. (2005) Structural basis for thermal stability of human low-density lipoprotein *Biochemistry* 44, 3965-71. DMPC: 1,2-Dimyristoyl-sn-Glycero-3-Phosphocholine (Avanti Polar Lipids). Purified apolipoprotein protein or truncation (ApoE422k). TBS Buffer: 10 mM Tris-HCl; 0.15 M NaCl; 0.25 mM EDTA; 0.005% $NaN_3$ (sodium azide); adjust to pH 7.4. 30° C. and 20° C. water baths. Probe or bath sonicator. Spin filter, 0.45 µm Concentrator 50 kD MWCO, Vivaspin 2 (Sartorius Inc.). FPLC Instrument (Shimadzu SCL-10A), size exclusion column (Superdex 200 10/300 GL (GE Healthcare Life Sciences).

Membrane Protein Incorporation into Nanolipoprotein Particles (NLPs)

Start water bath incubators. Temperatures at 30° C. and 20° C. Probe sonicate 34 mg of DMPC into 1 mL of TBS at 6 amps for approximately 15 minutes or until optical clarity is achieved. Alternatively, sonicate in bath sonicator to optical clarity. Centrifuge the solution at 13K for 2 minutes to remove residual metal sloughed off from probe sonicator. For a 250 µL batch in a 1.5 mL Eppendorf tube. Combine Apo E422K with DMPC in a ratio of 1:4 by mass in TBS buffer. Sodium cholate solution is then added to a final concentration of 20 mM. Biotinylated bacteriorhodopsin (bR) membrane protein is added in a 0.67 mass ratio to the Apo E422k apoliprotein. Transition temperature procedure: Immerse tube in water bath for 10 minutes each 30° C. (above DMPC transition temp.) followed by 20° C. (below DMPC transition temp.). Repeat the procedure three times then incubate at 23.8° C. overnight. To remove the cholate detergent and allow for self-assembly of MP-NLPs (bR-NLPs) the sample is loaded into a pre-soaked D-Tube Dialyzers, mini (Novagen). The sample is then dialyzed against 3 changes each of 1 L TBS buffer over a 2-3 day period at room temperature. Concentrate using an ultrafiltration device, Vivaspin 2 (Sartorius) MWCO 50K to 200 µL. Transfer supernatant into new tube Size exclusion chromatography is performed using a Shimadzu SCL-10A FPLC, equipped with a Superdex 200 10/300 GL column (GE Healthcare Life Sciences). The buffer is TBS with a 200 µL sample injection volume, a 0.5 mL/min flow rate and 0.5 mL-1.0 mL fraction size. Concentrate the fractions of interest using an ultrafiltration device, Vivaspin 2 (Sartorius) MWCO 50K for NLP peaks.

DMPC [1,2-Dimyristoyl-sn-Glycero-3-Phosphocholine] (Avanti Polar Lipids). Purified apolipoprotein or truncation (ApoE4 22 kD). TBS Buffer: 10 mM Tris-HCl; 0.15 M NaCl; 0.25 mM EDTA; 0.005% $NaN_3$ (sodium azide); adjust to pH 7.4. Sodium Cholate (Sigma) 500 mM solution in TBS. Biotinylated Bacteriorhodopsin (bR) (Sigma). 30° C. and 20° C. and 23.8° C. water baths. Probe Sonicator. Dialysis cups 10,000 MWCO (Pierce) or D-Tube Dialyzers, mini (Novagen). Spin filter, 0.45 µm. FPLC Instrument (Shimadzu SCL-10A), size exclusion column (Superdex 200 10/300 GL (GE Healthcare Life Sciences). Concentrator 50 kD MWCO, Vivaspin 2 (Sartorius Inc.)

Size Exclusion Chromatography—

The NLPs made with and without incorporated membrane protein can be purified from 'free protein' and 'free lipid' by HPLC (Shimadzu) using a Superdex 200 10/300 GL column (GE Healthcare), with TBS at a flow rate of 0.5 ml/min. The column can be calibrated with four protein standards HMW Gel filtration calibration kit (GE Healthcare), of known molecular weight and Stokes diameter that span the separation range of the column and the NLP samples. The void volume can be established with blue dextran. The NLP fraction can be concentrated about 10-fold to approximately 1.0 mg/ml using molecular weight sieve filters (Vivascience) having molecular weight cutoffs of 50 kDa. Protein concentration can be determined using the ADV01 protein concentration kit (Cytoskeleton), which is based on Coomassie dye binding.

SDS Page—

A 1 µL aliquot of the total (T) cell-free reaction, soluble (S) fraction and resuspended pellet (P) can be diluted with 1×SDS Sample buffer with reducing agents (Invitrogen), heat denatured and loaded on to a 4-12% gradient pre-made Bis-Tris gel (Invitrogen) along with the molecular weight standard SeeBlue plus2 (Invitrogen). The running buffer can be 1λ MES-SDS (Invitrogen). Samples can be electrophoresed for 38 minutes at 200V. Gels can be stained with Coomassie brilliant blue.

Native PAGE—

Equal amounts of NLP samples (0.5-1.0 µg) can be diluted with 2× native gel sample buffer (Invitrogen) and loaded onto 4-20% gradient pre-made Tris—glycine gels (Invitrogen). Samples can be electrophoresed for 2 hrs. at a constant 125 V. After electrophoresis, gels can be incubated with SYPRO Ruby protein gel stain (Bio-Rad) for 2 hours and then de-stained using 10% MeOH, 7% Acetic acid. Following a brief wash with dd$H_2O$, gels can be imaged using the green laser (532 nm) of a Typhoon 9410 (GE Healthcare) with a 610 nm bandpass 30 filter. Molecular weights can be determined by comparing migration vs. log molecular weight of standard proteins found in the Native-Mark standard (Invitrogen).

AFM—

NLPs can be imaged using and Asylum MFP-3D-CF atomic force microscope. Images can be captured in tapping mode with minimal contact force and scan rates of 1 Hz. Asylum software can be used for cross-sectional analysis to measure NLP height and diameter.

The following article is incorporated by reference in its entirety: Bayburt, T. H., Carlson, J. W., and Sligar, S. G. (1998) Reconstitution and imaging of a membrane protein in a nanometer-size phospholipid bilayer. *J Struct Biol* 123.

Labeling the NLPs with Alexa Fluor Dyes

NLPs can be labeled with either AF647 (stability experiments) or AF750 (bio distribution experiments) by incubating the NLPs with the respective reactive dye for at least 2 hrs (5:1 dye:NLP molar ratio). The reaction can be performed in PBS buffer containing 5 mM sodium bicarbonate, pH 8.2. After completion of the reaction, 10 mM Tris pH 8.0 can be added to quench any unreacted dye and incubated for 30 minutes. The samples can be then run on SEC (Superdex 200 PC 3.2/30 column, GE Healthcare, Piscataway, N.J.) to purify out the labeled NLP from unreacted dye (0.15 mL/min flow rate). The SEC fractions corresponding to the NLP can be then pooled and concentrated using 50 kDa MWCO spin concentrators. The apoE422k concentration can be determined using the Advanced Protein Assay Reagent (Cytoskeleton Inc., Denver, Colo.), where BSA can be used as the standard. The concentrated NLP samples can be then stored at 4° C. until further use. The following article, which is incorporated by reference in its entirety: Fischer N O, et al. (2014) Evaluation of Nanolipoprotein Particles (NLPs) as an In Vivo Delivery Platform. PLoS ONE 9(3): e93342.

Analysis of Conjugation of Biological Molecules to the NLP

Due to the significant size difference between the NLPs and free protein, SEC can be used as a quantitative tool to assess conjugation of biological molecules to the NLP. NLP samples can be analyzed by SEC (Superdex 200 PC 3.2/30 column, GE Healthcare) in PBS buffer. A flow rate of 0.15 ml/min can be used to ensure no overlap in the elution of unbound protein and NLP. The samples can be monitored and detected at an absorbance wavelength of 280 nm. For the protein conjugation experiments, purified NLP fractions can be analyzed by SDS-PAGE, using SYPRO Ruby protein gel stain for visualization. Densitometry can be used to quantify conjugated protein, using appropriate 0841 and apoE422k protein standards. Previously, computational modeling of apoE422k containing NLPs indicated that NLPs that can be 23.5 nm in diameter have 6 apoE422k per NLP. Therefore, in these experiments, the NLP concentration can be calculated based on the apoE422k concentration by assuming that each NLP contained 6 apoE422k scaffold proteins.

NLP Cross-Linking

For cross-linking experiments, NLP populations isolated by SEC can be incubated with Bis-N-succinimidyl-(pentaethylene glycol) ester (henceforth abbreviated as $PEO_5$). NLPs (ca. 25 ng apoLp-III per µL) in HEPES buffer (10 mM HEPES, 75 mM NaCl, pH 7.4) can be incubated with 0, 0.5 and 5 mM $PEO_5$ for four hours at room temperature. Reactions can be quenched with 50 mM Tris-HCl (pH 7.4) for 30 minutes at room temperature. Samples can be analyzed by NDGGE (4-20% Tris-glycine) and SDS PAGE (4-12% Bis-Tris with MES running buffer or 3-8% Trisacetate with tricine running buffer). For denaturing gels, the Mark 12 protein standard can be used (Invitrogen).

Validating Protein Association Native Gel Electrophoresis:

Validating NLP formation by native gel electrophoresis and confirmation of membrane protein association and functionality with NLPs by protein microarray and UV-visible spectroscopy. Native polyacrylamide gel electrophoresis is used to validate the association of proteins of interest (apolipoprotein and/or membrane protein) with NLP fractions eluted from the size exclusion column protein identification is confirmed with mass spectrometry. We use contact microarray spotting technology to attach NLPs to an amino-silane coated glass slide in an array format for streptavidin binding studies. Biotinylated bacteriorhodopsin (bR) is used to validate the incorporation of bR into nanolipoprotein particle fractions eluted from size exclusion chromatography. Cyanine-5-Strepavidin is used for fluorescence detection of biotinylated bacteriorhodopsin. UV-visible spectroscopy of light and dark adapted bacteriorhodopsin can be used to determine the functionality of the protein and relates information regarding the conformation of the protein.

In-depth physical characterization of these particles is used to demonstrate functional protein insertion/association. Combined with the biochemical evidence methods such as Atomic force microscopy (AFM) and Electron microscopy (EM) addresses whether the end product of self-assembly/ association can be successful by determining physical parameters to identify insertion and localization of membrane proteins. Atomic force microscopy (AFM), and Electron microscopy although not fully described here, but are used to image the prepared discs and determine diameter and height measurements as well as sample heterogeneity.

Native Gel Electrophoresis

Native-PAGE gels, 4-20% Tris-glycine with 0.75 µg total loaded protein estimated by $A_{280}$ absorbance. Load 10 µL of molecular weight standards, Native mark (Invitrogen) diluted 20× in native sample buffer. The gel is run at 125V for approximately 2 hours. Stain gels with ~150 mL of SyproRuby protein stain (Bio-Rad) following the microwave staining method: 30 sec. microwave, 30 sec. mixing on shaker table, 30 sec microwave, 5 min. shake, 30 sec. microwave, finally 23 min. on shaker table at room temperature. Destain gels for 1.5 hours on a shaker table at room temperature. Image the gel using a Typhoon Imager with appropriate filters selected for the SyproRuby fluorescence.

Traditionally, size exclusion chromatography (SEC) (15, 16), non-denaturing gradient gel electrophoresis (GGE) (6, 21), small angle X-ray scattering (SAXS) (22, 23) and transmission electron microscopy (TEM) (8, 9, 13) have been used to characterize particle size. Because SEC, GGE and SAXS all determine particle size derived from averages of ensembles of particles, none can provide biophysical data capturing subtle differences in particle size from multiple heterogeneous populations. Single particle sizing techniques, such as transmission electron microscopy (TEM), atomic force microscopy (AFM) and ion mobility spectroscopy (IMS) enable quantification of the size of individual NLPs allowing the population size distribution to be examined. Such information has the potential to provide insights into the relationship between NLP size and structural composition and may prove valuable for biotechnology applications of NLPs as model membrane systems for membrane protein solubilization. For example, understanding the size distribution of different NLP assemblies may be essential for accommodating different sized membrane proteins. Materials: Phospholipids 1,2-Dimyristoyl-sn-Glycero-3-Phosphocholine (DMPC) and 1,2-Dioleoyl-sn-Glycero-3-Phosphocholine (DOPC) can be purchased from Avanti Polar.

Lipids, Inc. (Alabaster, Ala.). Full-length apoA-I, Nanodisc™ particles can be purchased from Nanodisc, Inc., (Urbana, Ill.); apoE422k protein, can be prepared "in-house", has a 6His-tag to facilitate purification. Dried DMPC can be dissolved in 10 mM Tris pH 7.4, 0.15 M sodium chloride, 0.25 mM EDTA, 0.005% sodium azide (TBS) buffer at a concentration of 20 mg/ml followed by probe sonication to clarity. This resulting liposome suspension can be spun at 13000 g for 2.5 minutes to remove any residual titanium from the probe sonicator and un-solubilized lipid. ApoE422k (200-250 µg) can be added to the TBS/DMPC solution at a mass ratio of 4:1. The particle formation process can be started with 3 repeated sets of transition temperature incubations, above (10 minutes at 30° C.) and below the transition temperature of DMPC (23.8° C.) followed by incubation at 23.8° C. overnight. The NLPs can be purified by size-exclusion chromatography using a Superdex 200 HR 10/300 column (GE Healthcare), in TBS at a flow rate of 0.5 ml/min. The NLP fractions can be concentrated to approximately 0.1 mg/ml using molecular weight sieve filters (Vivascience) with molecular weight cutoffs of 50 kDa. Protein concentration can be determined using the ADV01 protein concentration kit (Cytoskeleton, Inc.).

Atomic force microscopy (AFM): Atomically flat Muscovite mica disks can be glued to metal substrates to secure them to the scanner of a stand-alone MFP-3D AFM (Asylum Research, Santa Barbara, Calif.). Two uL of solution at 1.0 µg/mL concentration can be incubated for two minutes on the mica surface in imaging buffer (10 mM $MgCl_2$, 10 mM Tris-HCl, and 0.1 M NaCl, adjusted to pH 8.0) then lightly rinsed. The AFM has a closed loop in the x, y, and z axes. Topographical images can be obtained with silicon nitride cantilever probes (MSCT, Veeco, Santa Barbara, Calif.) with a spring constant of 0.05 N/m. Images can be taken in alternate contact (AC) mode in liquid, with amplitudes below 20 nm and an amplitude setpoint at 50% tapping amplitude. Scan rates can be below 1.5 Hz. Height, amplitude, and phase images can be recorded. Diameters of particles in images can be determined by the full width half maximum (FWHM) analysis of contiguous particles in the slow scan direction, using IgorPro Wavemetrics software routines. Heights of particles can be determined from histogram analysis. Experiments can be carried out in a temperature controlled room at 23+/−1° C. Alternate contact mode or tapping mode can be used in AFM imaging to ensure minimal structural perturbation from tip-sample contact force. It is widely known that imaging nano-scale particles with AFM results in laterally broadening particle size due to tip convolution effects, but there exists a second broadening effect due to the finite response of imaging feedback in the fast scan direction (25). This latter effect can result in the NLPs shape appearing elongated in the fast scan direction. To limit tip convolution effects, only tips revealing sharp imaging can be used for analysis. To limit the broadening from slow imaging response, FWHM from a cross-section perpendicular to the fast scan direction can be used to determine particle diameter. To determine the reproducibility of the procedure for measuring NLP diameters, randomly selected particles can be repeatedly imaged to verify consistent diameter measurements.

NLP Modeling and Molecular Dynamics:

An idealized 35 $nm_2$ bilayer slab of DMPC lipids (a 740,000 atom system) can be created and equilibrated to give a lipid cross-sectional area of 52 $Å^2$ per lipid (15). Circular discs can be cut out of this slab at 0.5 nm diameter increments, in a range of 11 to 30 nm. The apoE422k crystal structure, PDB:1GS9 can be used as the basis for the protein modeling. Refolded E422k proteins can be modeled and tested in three different forms: fully extended, doubled-back/ "hairpin", and semi-extended/"double-hairpin" folds. Initial modeling of the NLPs can be based on a fully extended E422k assuming E422k NLPs would be similar to the "double belt" model reported for A-I NLPs (29-32) and previously suggested for E322K NLPs (33). This gave rise to a fold for E422k, with full hydrophobic association for the lipid, that is fully extended—as previously suggested for this portion of E4(10). However, at least two other folds are possible for E422k consistent with water exclusion of the hydrophobic acyl chains. The soluble folded-E422k contains three hairpin turns linking four helices (34). Forming a hairpin in the extended fold so that the E4 doubles back on itself creates a model with a self-contained double-belt This so-called "hairpin" model for lipoproteins has been previously suggested (35). For this fold to form, the loop between helices 2 and 3 of folded E422k would have to undergo a 180° rotation. A more energetically favorable rearrangement of E422k would involve only the opening of the 2-3 loop to produce a semi-extended "double-hairpin" model—that is, one containing two of the bends from the folded-E422k and involving a simple opening of the hydrophobic core of the folded-E422k to pack against the hydrophobic face of the lipid). Proteins can be aligned along the equator of the lipid disc and packed against the lipid discs of different sizes with the aim of fully enclosing the hydrophobic face of the lipids but not allowing the proteins to overlap each other. A 1 nanosecond (ns) equilibration molecular dynamics (MD) run can be then used to optimize the packing of the lipid against the protein. NLPs without gaps between lipid and protein can be then entered into a 40 ns MD simulation to determine the stability of the model. All MD simulations can be run using the CHARMM forcefield (36) in NAMD (37) with many of the settings and set-up details taken from previous simulations (38, 39). Simulations can be conducted on 1024 processors of Thunder, a 23 teraflop, 4096 Intel Itanium2 processor machine at the Livermore Computing Center. System set-up, analysis and image preparation can be done using, Gromacs (40), Pymol and VMD (41) with additional "in house" tcl/tk, perl and C++ scripts.

Verification of NLPs Modeling and Molecular Dynamics Through Simulations of E422k DAMPC NLPs To determine if the discrete NLP diameters observed by AFM, TEM and IMS could be related to the number of E422k proteins in an NLP, NLP assembly can be computationally modeled using MD simulations. Computer modeling of E422k/DMPC NLPs can be used to reveal whether the multiple sizes are stable, where all the hydrophobic faces of the lipid bilayer disc structure can be matched by the protein numbers, sizes and stoichiometry. A double-belt model can be assumed; this criterion can be satisfied by three protein conformations; extended, hairpin, or double-hairpin. NLPs containing an odd number of E422k, the 19 nm (5 scaffold) and 28 nm (7 scaffold) NLPs, can be stable if at least one E422k adopted either the hairpin or double-hairpin motif.

Figure 10:
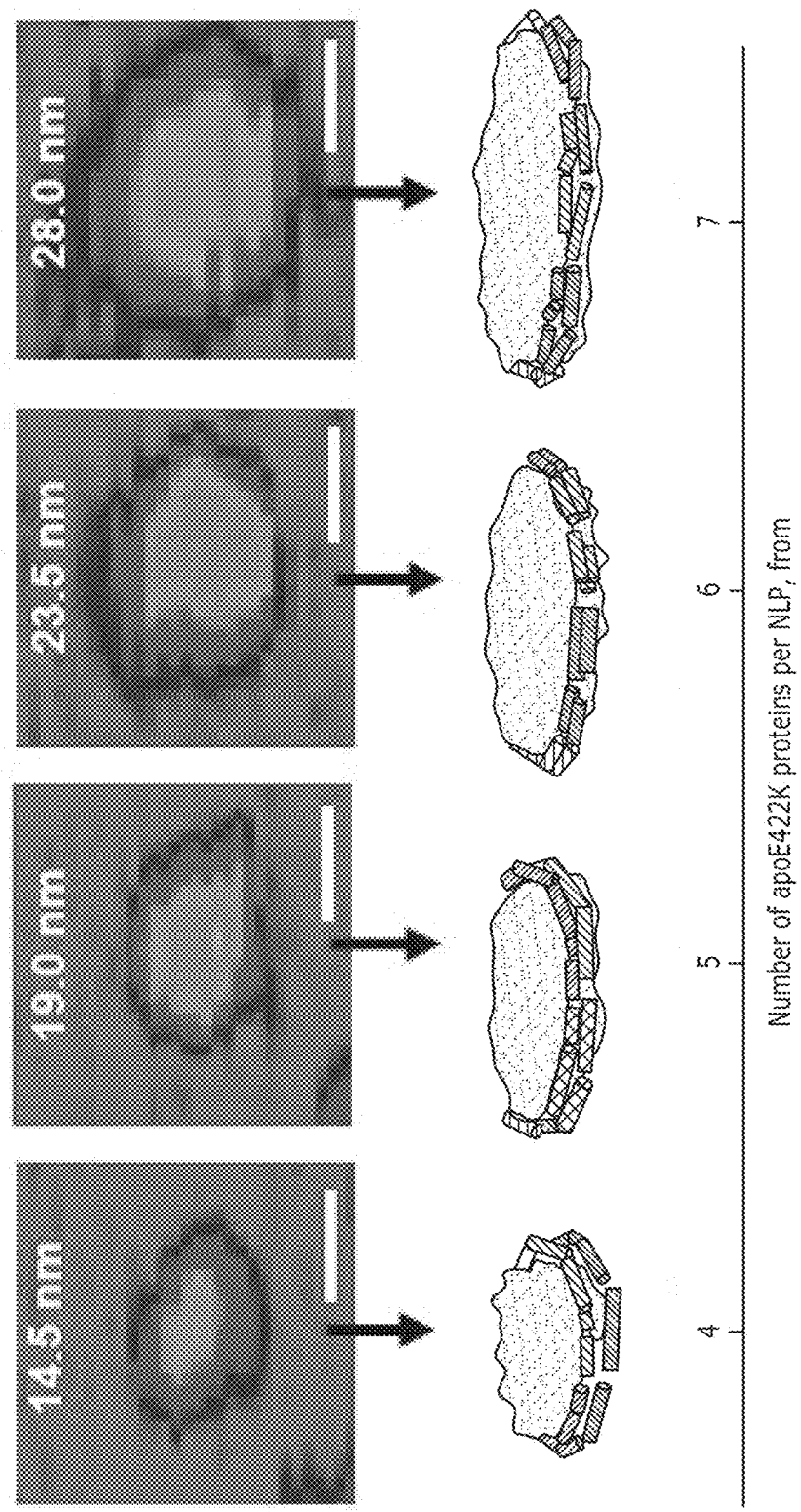
FIG. 10 shows modeling and molecular dynamics computer simulations of apolipoprotein/DMPC NLPs sizes; the apolipoproteins are helical motifs in the simulated image; realistic and/or putative structures are realizable for particles between 14.5 nm and 28 nm scale bar from AFM imaging—10 nm. In the cartoon representation on the bottom of the figure different helical segment of the apolipoprotein are indicated with different markings.

Modeling of NLPs using fully extended double-belted E422k proteins could produce NLPs of diameter 14.5 and 23.5 nm respectively containing 4 and 6 copies of the E422k protein (FIG. 10). The extended conformation of the E4 protein implies that the protein are added in pairs to produce a double-belt and fully satisfy the hydrophobic matching required to stabilize the disc of lipid. Modeling could therefore not reproduce NLPs with diameters of 19 nm and 28 nm using fully extended double-belted E422k proteins.

Interestingly, MD simulations revealed that stable NLPs with diameters of 14.5, 19, 23.5 and 28 nm could all be formed using the hairpin and double-hairpin models of E422k. Furthermore, simulations revealed that the 19 nm and 28 nm NLPs respectively contain 5 and 7 E422k proteins with at least one of the proteins, if not more, forming a hairpin or double-hairpin. In addition, MD simulations revealed NLPs formed from either hairpin, double-hairpin and extended models of E422k have similar stability, with full hydrophobic matching at satisfactory lipid:protein ratios as the most important factor for stability. This suggests the possibility that any one NLP can contain E422k proteins in any one or more of the three different folded forms. The only constraint is that the 19 nm and 28 nm NLP are unlikely to be formed from E422k apolipoprotein that is only in the extended conformation. Simulations can be able to verify the experimental size data yielding the following size:

protein number:lipid number ratios:14.5 nm:4:433, 19 nm:5: 783, 23.5 nm:6:1270, and 28 nm:7:1780.

Figure 11A:
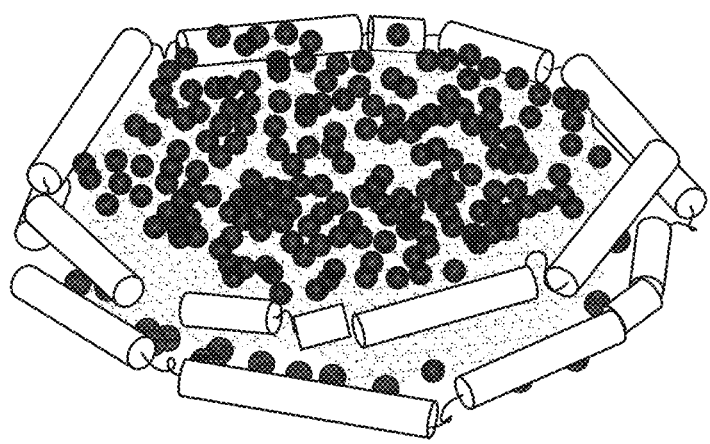
FIG. 11A shows a model of a Nanolipoprotein particle (NLP) with a lipid bilayer and apolipoproteins white cylinders encircling the hydrophobic portion of the lipids (black circles and dotted area)
Figure 11B:
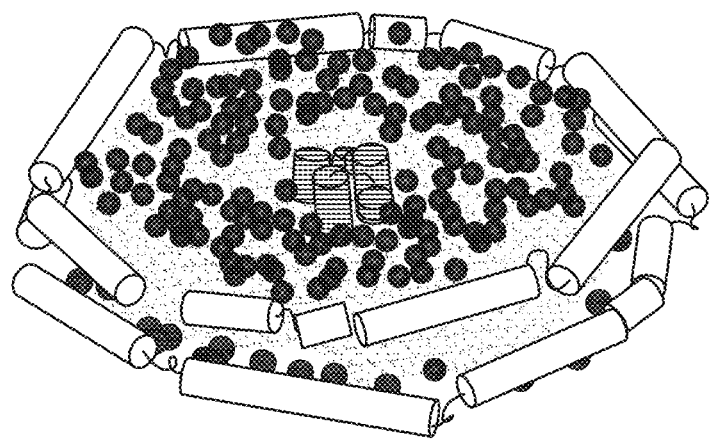
FIG. 11B shows a NLP modeled with an integral membrane protein monomer (cylinders marked with horizontal lines) inserted in the hydrophobic lipid core (black circles and dotted area).
Figure 11C:
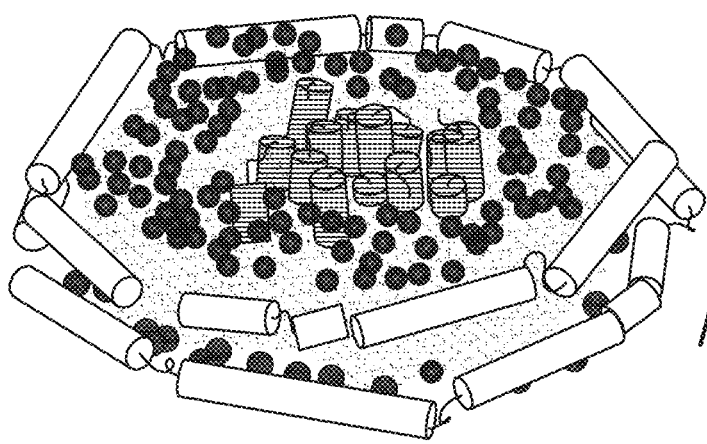
FIG. 11C A NLP modeled with an integral membrane protein trimer (cylinders marked with horizontal lines) inserted in the hydrophobic lipid core (black circles).

Additional models are illustrated in FIG. 11. In particular in panel FIG. 11A, a model of a Nanolipoprotein particle (NLP) is shown with a lipid bilayer in the middle and apolipoproteins encircling the hydrophobic portion of the lipids. In FIG. 11B, an NLP modeled with a bacteriorhodopsin monomer inserted in the hydrophobic lipid core is shown. In FIG. 11C, an NLP modeled with a bacteriorhodopsin trimer inserted in the hydrophobic lipid core is shown.

The computer modeling and molecular dynamics (MD) simulations indicate that these NLPs sizes can be related to a quantized number of the E422k lipoproteins surrounding the NLPs. Discrete sizes can be also observed in NLPs self-assembled from E422k/1,2-Dioleoyl-sn-Glycero-3-Phosphocholine (DOPC), A-I/DMPC, and commercially obtained NLPs purchased from Nanodisc, Inc. indicating this is likely a general and physically relevant phenomenon.

In summary, described herein are synthetic apolipoproteins based on native/naturally occurring homolog proteins that can be prepared using solid-phase peptide synthesis approaches combined with native chemical ligation methods to create analogs of full length apolipoproteins. The chemical synthesis is expected to allow introduction of non-natural amino acids, e.g., α,α'-dialkyl amino acids, with a periodicity that encourages both helix formation and amphipathicity. Such apolipoprotein analogs are expected to encourage, in some embodiments, facile and more complete NLP formation, enabling consideration of full spectrum of nanoparticle-based biotechnology applications ranging from therapeutic sequestration and delivery to energy/biofuel production to biopolymer production.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file IL-12402-PCT-Sequence-Listing_ST25 created on Sep. 8, 2016 and filed concurrently herewith is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Wallin, E., and von Heijne, G. (1998) Genome-wide analysis of integral membrane proteins from eubacterial, archaean, and eukaryotic organisms *Protein Sci* 7, 1029-38.
2. Klammt, C., Schwarz, D., Eifler, N., Engel, A., Piehler, J., Haase, W., Hahn, S., Dotsch, V., and Bernhard, F. (2007) Cell-free production of G protein-coupled receptors for functional and structural studies *J Struct Biol*.
3. Sawasaki, T., Hasegawa, Y., Tsuchimochi, M., Kamura, N., Ogasawara, T., Kuroita, T., and Endo, Y. (2002) A bilayer cell-free protein synthesis system for high-throughput screening of gene products *FEBS Lett* 514, 102-5.

4. Frydman, J., and Hartl, F. U. (1996) Principles of chaperone-assisted protein folding: differences between in vitro and in vivo mechanisms *Science* 272, 1497-502.
5. Klammt, C., Lohr, F., Schafer, B., Haase, W., Dotsch, V., Ruterjans, H., Glaubitz, C., and Bernhard, F. (2004) High level cell-free expression and specific labeling of integral membrane proteins *Eur J Biochem* 271, 568-80.
6. Ishihara, G., Goto, M., Saeki, M., Ito, K., Hori, T., Kigawa, T., Shirouzu, M., and Yokoyama, S. (2005) Expression of G protein coupled receptors in a cell-free translational system using detergents and thioredoxin-fusion vectors *Protein Expr Purif* 41, 27-37.
7 Klammt, C., Schwarz, D., Fendler, K., Haase, W., Dotsch, V., and Bernhard, F. (2005) Evaluation of detergents for the soluble expression of alpha-helical and beta-barrel-type integral membrane proteins by a preparative scale individual cell-free expression system *Febs J* 272, 6024-38.
8. Bayburt, T. H., Carlson, J. W., and Sligar, S. G. (1998) Reconstitution and imaging of a membrane protein in a nanometer-size phospholipid bilayer. *J Struct Biol* 123, 37-44.
9. Bayburt, T. H., and Sligar, S. G. (2002) Single-molecule height measurements on microsomal cytochrome P450 in nanometer-scale phospholipid bilayer disks *Proc Natl Acad Sci USA* 99, 6725-30.
10. Bayburt, T. H., and Sligar, S. G. (2003) Self-assembly of single integral membrane proteins into soluble nanoscale phospholipid bilayers *Protein Sci* 12, 2476-81.
11. Civjan, N. R., Bayburt, T. H., Schuler, M. A., and Sligar, S. G. (2003) Direct solubilization of heterologously expressed membrane proteins by incorporation into nanoscale lipid bilayers *Biotechniques* 35, 556-60, 62-3.
12. Chromy, B. A., Arroyo, E., Blanchette, C. D., Bench, G., Benner, H., Cappuccio, J. A., Coleman, M. A., Henderson, P. T., Hinz, A. K., Kuhn, E. A., Pesavento, J. B., Segelke, B. W., Sulchek, T. A., Tarasow, T., Walsworth, V. L., and Hoeprich, P. D. (2007) Different Apolipoproteins Impact Nanolipoprotein Particle Formation *J Am Chem Soc*.
13. Bayburt, T. H., Grinkova, Y. V., and Sligar, S. G. (2006) Assembly of single bacteriorhodopsin trimers in bilayer nanodiscs *Arch Biochem Biophys* 450, 215-22.
14. Shaw, A. W., McLean, M. A., and Sligar, S. G. (2004) Phospholipid phase transitions in homogeneous nanometer scale bilayer discs *FEBS Lett* 556, 260-4.
15. Gursky, O., Ranjana, and Gantz, D. L. (2002) Complex of human apolipoprotein C-1 with phospholipid: thermodynamic or kinetic stability? *Biochemistry* 41, 7373-84.
16. Jayaraman, S., Gantz, D., and Gursky, 0. (2005) Structural basis for thermal stability of human low-density lipoprotein *Biochemistry* 44, 3965-71.
17. Jonas, A. (1986) Reconstitution of high-density lipoproteins *Methods Enzymol* 128, 553-82.
18. Jonas, A., Kezdy, K. E., and Wald, J. H. (1989) Defined apolipoprotein A-I conformations in reconstituted high density lipoprotein discs *J Biol Chem* 264, 4818-24.
19. Peters-Libeu, C. A., Newhouse, Y., Hatters, D. M., and Weisgraber, K. H. (2006) Model of biologically active apolipoprotein E bound to dipalmitoylphosphatidylcholine *J Biol Chem* 281, 1073-9.
20. 30. Tufteland, M., Pesavento, J. B., Bermingham, R. L., Hoeprich, P. D., Jr., and Ryan, R. O. (2007) Peptide stabilized amphotericin B nanodisks *Peptides* 28, 741-6.
21. Cruz, F., and Edmondson, D. E. (2007) Kinetic properties of recombinant MAO-A on incorporation into phospholipid nanodisks *J Neural Transm* 114, 699-702.
22. Boldog, T., Grimme, S., Li, M., Sligar, S. G., and Hazelbauer, G. L. (2006) Nanodiscs separate chemoreceptor oligomeric states and reveal their signaling properties *Proc Natl Acad Sci USA* 103, 11509-14.
23. Forstner, M., Peters-Libeu, C., Contreras-Forrest, E., Newhouse, Y., Knapp, M., Rupp, B., and Weisgraber, K. H. (1999) Carboxyl-terminal domain of human apolipoprotein E: expression, purification, and crystallization *Protein Expr Purif* 17, 267-72.
24. Morrow, J. A., Arnold, K. S., and Weisgraber, K. H. (1999) Functional characterization of apolipoprotein E isoforms overexpressed in Escherichia coli *Protein Expr Purif* 16, 224-30.
25. Camarero, J. A., Kwon, Y., and Coleman, M. A. (2004) Chemoselective attachment of biologically active proteins to surfaces by expressed protein ligation and its application for "protein chip" fabrication *J Am Chem Soc* 126, 14730-1.
26. Rao, R. S., Visuri, S. R., McBride, M. T., Albala, J. S., Matthews, D. L., and Coleman, M. A. (2004) Comparison of multiplexed techniques for detection of bacterial and viral proteins *J Proteome Res* 3, 736-42.
27. 43. Bayburt, T. H., Leitz, A. J., Xie, G., Oprian, D. D., and Sligar, S. G. (2007) Transducin activation by nanoscale lipid bilayers containing one and two rhodopsins *J Biol Chem* 282, 14875-81.
28. Baas, B. J., Denisov, I. G., and Sligar, S. G. (2004) Homotropic cooperativity of monomeric cytochrome P450 3A4 in a nanoscale native bilayer environment *Arch Biochem Biophys* 430, 218-28.
29. Leitz, A. J., Bayburt, T. H., Barnakov, A. N., Springer, B. A., and Sligar, S. G. (2006) Functional reconstitution of Beta2-adrenergic receptors utilizing self-assembling Nanodisc technology *Biotechniques* 40, 601-2, 04, 06, passim.
30. Nath, A., Atkins, W. M., and Sligar, S. G. (2007) Applications of Phospholipid Bilayer Nanodiscs in the Study of Membranes and Membrane Proteins *Biochemistry*.

The invention claimed is:

1. A synthetic apolipoprotein configured to bind lipids to form lipoproteins comprising:

a plurality of helical segments each having a primary structure configured to form an alpha helix secondary structure, wherein at least one helical segment of the plurality of helical segments comprises a plurality of hydrophobic amino acids and a plurality of hydrophilic amino acids positioned in the primary structure to provide an amphipathic alpha helix secondary structure, wherein the plurality of hydrophobic amino acids form an hydrophobic amino acid cluster and the plurality hydrophilic amino acids form an hydrophilic amino acid cluster, and wherein the at least one helical segment comprises one or more non-natural α,α'-dialkyl amino acids within the hydrophobic amino acid cluster, the plurality of hydrophobic amino acids is positioned in the primary structure with a periodicity $i_o+x_o$ where $i_o$ is a recurring position of a hydrophobic amino acid of plurality of hydrophobic amino acids in the primary structure and $x_o$ is a number of amino acids in the helical segment between a first occurrence and a second occurrence of the recurring position $i_o$, and the plurality of hydrophilic amino acids is positioned in the primary structure with a periodicity $i_i+x_i$ where $i_i$ is a recurring position of a hydrophilic amino acid of the plurality of hydrophilic amino acids in the primary structure and $x_i$ is a number of amino acids in the helical segment between a first occurrence and a second occurrence of the recurring position $i_i$ and wherein $x_o$ and $x_i$ are independently any integer number from 3 to 9.

2. The synthetic apolipoprotein of claim 1, wherein a C1-C4 linear or branched alkyl side chain is independently presented in a' position of the one or more of the one or more non-natural α,α'-dialkyl amino acids.

3. The synthetic apolipoprotein of claim 1, wherein a methyl, ethyl propyl, or an isobutyric side chain is independently presented in α' position of one or more of the one or more non-natural α,α'-dialkyl amino acids.

4. The synthetic apolipoprotein of claim 1, wherein the synthetic apolipoprotein comprises one or more helical segments having a length of 6, 7, 10, 11, 13, 14, 17, 18, 21, 22, 24, 25, 28, 29 or 31 amino acid residues.

5. The synthetic apolipoprotein of claim 1, wherein at least one helical segment comprises from 15 to 100 amino acids.

6. The synthetic apolipoprotein of claim 1, wherein at least one helical segment comprises 20 to 50 amino acids.

7. The synthetic apolipoprotein of claim 1, wherein $x_o$ and $x_i$ are independently 3 and/or 4.

8. The synthetic apolipoprotein of claim 1, wherein the first occurrence $i_o$ is at position 1 of the alpha helical segment and the additional occurrence are at positions 4, 5, 8, 9, 11, 12, and 15.

9. The synthetic apolipoprotein of claim 1, wherein the first occurrence $i_o$ is at position 1 of the alpha helical segment and the additional occurrence are at positions 4, 7, 10, 13, 16, 19, 22, 25, 28, 31, 34, 37, 40, 43, 46, and 49 of the alpha helical segment.

10. The synthetic apolipoprotein of claim 1, wherein the first occurrence $i_i$ is at position 2 of the alpha helical segment and the additional occurrence are at positions 3, 6, 7, 9, 10, 13, and 14 of the alpha helical segment.

11. The synthetic apolipoprotein of claim 1, wherein the plurality of helical segments is connected by a linker comprising 1 to 15 amino acids.

12. The synthetic apolipoprotein of claim 1, wherein the plurality of helical segments is connected by a linker comprising 1 to 10 L-amino acids.

13. The synthetic apolipoprotein of claim 1, wherein the number of helical segments ranges between three and twelve.

14. A nanolipoprotein particle (NLP), comprising a membrane forming lipid, and a scaffold protein, wherein the scaffold protein is the synthetic apolipoprotein of claim 1.

15. A method to provide the synthetic apolipoprotein of claim 1, the method comprising
synthesizing a plurality of helical segments
each helical segment comprising a plurality of hydrophobic amino acid and a plurality of hydrophilic amino acid,
each helical segment having a primary structure configured to form an amphipathic alpha helical secondary structure in which the plurality of hydrophobic amino acid form a hydrophobic cluster and the plurality of hydrophilic amino acid form a hydrophilic cluster,
each helical segment having an N-terminal end and a C-terminal end; and
ligating the plurality of alpha-helical segments through the N-terminal end or the C-terminal end to form a synthetic apolipoprotein via at least one synthetic chemical linkage,
wherein at least one helical segment of the plurality of helical segment comprises one or more $\alpha,\alpha'$-dialkyl amino acids within the hydrophobic and/or the hydrophilic cluster.

16. A method to form nanolipoprotein particles (NLPs) comprising
synthesizing a synthetic apolipoprotein according to the method of claim 15; and
combining the synthetic apolipoprotein with membrane forming lipids to form a nanolipoprotein particle.

* * * * *